(12) United States Patent
Altman et al.

(10) Patent No.: US 9,969,749 B2
(45) Date of Patent: May 15, 2018

(54) INHIBITORS OF IRAK4 ACTIVITY

(71) Applicant: MERCK SHARP & DOHME CORP., Rahway, NJ (US)

(72) Inventors: Michael D. Altman, Needham, MA (US); Brian M. Andresen, Sharon, MA (US); Jason D. Brubaker, Cambridge, MA (US); Matthew L. Childers, Medfield, MA (US); Anthony Donofrio, Cambridge, MA (US); Thierry Fischmann, Scotch Plains, NJ (US); Craig R. Gibeau, Holliston, MA (US); Solomon D. Kattar, Wakefield, MA (US); Charles A. Lesburg, Newtown, MA (US); Jongwon Lim, Lexington, MA (US); John K. F. MacLean, Kilmarnock Ayrshire, Scotland (GB); Umar F. Mansoor, Hopkinton, MA (US); Alan B. Northrup, Reading, MA (US); John M. Sanders, Hatfield, PA (US); Luis Torres, Norwood, MA (US)

(73) Assignee: Merck Sharp & Dohme Corp., Rahway, NJ (US)

( * ) Notice: Subject to any disclaimer, the term of this patent is extended or adjusted under 35 U.S.C. 154(b) by 0 days. days.

(21) Appl. No.: 15/515,383

(22) PCT Filed: Sep. 25, 2015

(86) PCT No.: PCT/US2015/052111
§ 371 (c)(1),
(2) Date: Mar. 29, 2017

(87) PCT Pub. No.: WO2016/053771
PCT Pub. Date: Apr. 7, 2016

(65) Prior Publication Data
US 2017/0275297 A1    Sep. 28, 2017

Related U.S. Application Data

(60) Provisional application No. 62/057,692, filed on Sep. 30, 2014.

(51) Int. Cl.
| | | |
|---|---|---|
| *C07D 498/04* | (2006.01) |
| *A61K 45/06* | (2006.01) |
| *A61K 31/517* | (2006.01) |
| *C07D 403/04* | (2006.01) |
| *C07D 239/94* | (2006.01) |
| *C07D 401/04* | (2006.01) |
| *A61K 31/5377* | (2006.01) |
| *C07D 405/14* | (2006.01) |
| *C07D 401/14* | (2006.01) |
| *C07D 413/04* | (2006.01) |
| *C07D 405/04* | (2006.01) |
| *C07D 471/04* | (2006.01) |
| *A61K 31/5383* | (2006.01) |
| *C07D 491/048* | (2006.01) |
| *C07D 417/04* | (2006.01) |
| *C07D 409/04* | (2006.01) |

(52) U.S. Cl.
CPC .......... *C07D 498/04* (2013.01); *A61K 31/517* (2013.01); *A61K 31/5377* (2013.01); *A61K 31/5383* (2013.01); *A61K 45/06* (2013.01); *C07D 239/94* (2013.01); *C07D 401/04* (2013.01); *C07D 401/14* (2013.01); *C07D 403/04* (2013.01); *C07D 405/04* (2013.01); *C07D 405/14* (2013.01); *C07D 409/04* (2013.01); *C07D 413/04* (2013.01); *C07D 417/04* (2013.01); *C07D 471/04* (2013.01); *C07D 491/048* (2013.01)

(58) Field of Classification Search
CPC .................................................... C07D 498/04
See application file for complete search history.

(56) References Cited

U.S. PATENT DOCUMENTS

| | | |
|---|---|---|
| 2005/0119273 A1 | 6/2005 | Lipford et al. |
| 2011/0021513 A1 | 1/2011 | Durand-Reville et al. |
| 2011/0166168 A1 | 7/2011 | Buchmann et al. |
| 2013/0274241 A1 | 10/2013 | Jorand-Lebrun et al. |

FOREIGN PATENT DOCUMENTS

| | | |
|---|---|---|
| WO | WO2012097013 | 7/2012 |
| WO | WO2014058685 | 4/2014 |
| WO | WO2015164374 A1 | 10/2015 |
| WO | WO2016053769 | 4/2016 |
| WO | WO2016053772 | 4/2016 |
| WO | WO2016053770 | 7/2016 |
| WO | WO2016053771 | 4/2017 |

OTHER PUBLICATIONS

McMahon et al. (2000).*
Pinedo et al. (2000).*

* cited by examiner

*Primary Examiner* — Paul V Ward
(74) *Attorney, Agent, or Firm* — Gloria M. Fuentes; Matthew A. Leff

(57) ABSTRACT

The present invention relates to inhibitors of IRAK4 of Formula (I) and provides compositions comprising such inhibitors, as well as methods therewith for treating IRAK4-mediated or -associated conditions or diseases.

4 Claims, No Drawings

INHIBITORS OF IRAK4 ACTIVITY

BACKGROUND OF THE INVENTION

The present invention is directed to compounds which modulate interleukin-1 (IL-1) receptor-associated kinase 4 (IRAK4) and are useful in the prevention or treatment of inflammatory, cell proliferative and immune-related conditions and diseases.

The recruitment of immune cells to sites of injury involves the concerted interactions of a large number of soluble mediators. Several cyctokines appear to play key roles in these processes, particularly IL-1 and TNF. Both cytokines are derived from mononuclear cells and macrophages, along with other cell types. Physiologically, they produce many of the same proinflammatory responses, including fever, sleep and anorexia, mobilization and activation of polymorphonuclear leukocytes, induction of cyclooxygenase and lipoxygenase enzymes, increase in adhesion molecule expression, activation of B-cells, T-cells and natural killer cells, and stimulation of production of other cytokines. Other actions include a contribution to the tissue degeneration observed in chronic inflammatory conditions, such as stimulation of fibroblast proliferation, induction of collagenase, etc. They have also been implicated in the process of bone resorption and adipose tissue regulation. Thus, these cytokines play key roles in a large number of pathological conditions, including rheumatoid arthritis, inflammatory bowel disease, multiple sclerosis, diabetes, obesity, cancer, sepsis, etc.

The importance of IL-1 in inflammation has been demonstrated by the ability of the highly specific IL-1 receptor antagonist protein (IL-1Ra or IRAP) to relieve inflammatory conditions. See, e.g., Dinarello, Cytokine Growth Factor Rev., 1997, 8:253-265.

IL-1 treatment of cells induces the formation of a complex consisting of the two IL-1 receptor chains, IL-1R1 and IL-1RAcP, and the resulting heterodimer recruits an adaptor molecule designated as MyD88. See e.g., Wesche et al., J. Biol. Chem., 1999, 274:19403-19410. MyD88 binds to a protein designated IRAK (IL-1 receptor associated kinase). See, e.g., O'Neill et al., J. Leukoc. Biol., 1998, 63(6):650-657; Auron, Cytokine Growth Factor Rev., 1998, 9(3-4):221-237; and O'Neill, Biochem. Soc. Trans., 2000, 28(5):557-563. IRAK is subsequently phosphorylated and released from the receptor complex to interact with a tumor necrosis factor receptor-associated factor, TRAF6, which transduces the signal to downstream effector molecules. See e.g., Cao et al., Nature, 1996, 383:443-446. TRAF6 can trigger the NIK/IKK kinase cascade to activate the transcription factor NK-kappa B. NF-kappa B regulates a number of genes that, in turn, regulate immune and inflammatory responses.

Four IRAKs have been identified: IRAK1 (see, e.g., Cao et al., Science, 1996, 271:1128-1131), IRAK2 (see, e.g. Muzio et al., Science, 1997, 278:1612-1615), the monymeloic cell specific IRAKM, also known as IRAK3 (see, e.g., Wesche et al., J. Biol. Chem., 1999, 274:19403-19410), and IRAK4 (see, e.g., PCT Publication No. WO 01/051641). IRAK proteins have been shown to play a role in transducing signals other than those originating from IL-1 receptors, including signals triggered by activation of IL-18 receptors (see, e.g., Kanakaraj et al., J. Exp. Med., 1999, 189(7):1129-1138) and LPS receptors (see, e.g., Yang et al., J. Immunol., 1999, 163:639-643; and Wesche et al., J. Biol. Chem., 1999, 274:19403-19410). Over-expression of IRAK2 and IRAKM has been shown to be capable of reconstituting the response to IL-1 and LPS in an IRAK deficient cell line.

The identification of compounds that inhibit the function of IRAK4 represents an attractive approach to the development of therapeutic agents for the treatment of inflammatory, cell proliferative and immune-related conditions and diseases associated with IRAK4-mediated signal transduction, such as rheumatoid arthritis, inflammatory bowel disease, multiple sclerosis, diabetes, obesity, allergic disease, psoriasis, asthma, graft rejection, cancer, and sepsis.

It is an object of the instant invention to provide novel compounds that are inhibitors of IRAK4.

It is also an object of the present invention to provide pharmaceutical compositions that comprise the novel compounds that are inhibitors of IRAK4.

It is also an object of the present invention to provide a method for treating IRAK4-mediated and associated conditions or diseases that comprises administering such inhibitors of IRAK4 activity.

SUMMARY OF THE INVENTION

The present invention relates to inhibitors of IRAK4 of formula (I) and provides compositions comprising such inhibitors, as well as methods therewith for treating IRAK4-mediated or -associated conditions or diseases.

DETAILED DESCRIPTION OF THE INVENTION

The compounds of the instant invention are useful in the inhibition of the activity of IRAK4.

An embodiment of the instant invention is illustrated by the Formula I:

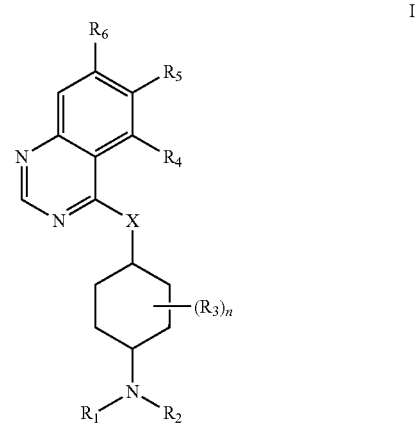

wherein:

X is NH or O;

b is 0 or 1;

n is 0, 1, 2, 3 or 4;

$R_1$ and $R_2$ are independently H and $(C_1$-$C_4)$alkyl, or $R_1$ and $R_2$ can be taken together with the nitrogen to which they are attached to form a heterocycle optionally containing, in addition to the nitrogen, one or two additional heteroatoms selected from N, O and S, said alkyl and heterocycle are optionally substituted with one or more substituents selected from $R_a$;

$R_3$ is $(C_1$-$C_4)$alkyl wherein two adjacent alkyl groups can join together and form a bridged moiety of 3-6 carbon atoms;

$R_4$ is absent, halo or $O_b(C_1$-$C_4)$alkyl;

R$_5$ is aryl or heteroaryl each optionally substituted with one or more substituents selected from R$_b$;

R$_6$ is absent, halo, or O(C$_1$-C$_4$)alkyl;

R$_a$ is independently selected from: halo, O$_b$(C$_1$-C$_4$)alkyl, SO$_2$(C$_1$-C$_4$)alkyl, C(O)C$_1$-C$_4$ alkyl, said alkyl optionally substituted with halo or heterocyclyl; and R$_b$ is independently selected from OH, halo, CHF$_2$, CF$_3$, COOH, SO$_2$(C$_1$-C$_4$)alkyl, C=O(O)C$_1$-C$_4$ alkyl, O$_b$(C$_1$-C$_4$)alkyl, aryl, heterocyclyl, CN, C(O)N(R$_c$)$_2$, N(R$_c$)$_2$; said R$_c$ and alkyl are optionally substituted with OH, O(C$_1$-C$_4$)alkyl and heterocyclyl; and R$_c$ is independently H, SO$_2$(C$_1$-C$_4$)alkyl, or C$_1$-C$_4$ alkyl; or a pharmaceutically acceptable salt or a stereoisomer thereof.

Another embodiment of the instant invention is illustrated by the Formula II:

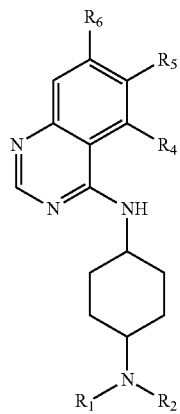

wherein:

b is 0 or 1;

R$_1$ and R$_2$ are independently H and (C$_1$-C$_4$)alkyl, or R$_1$ and R$_2$ can be taken together with the nitrogen to which they are attached to form: morpholinyl, piperidinyl, azetidinyl and piperazinyl, said alkyl, morpholinyl, piperidinyl, azetidinyl and piperaziyle are optionally substituted with one or more substituents selected from R$_a$;

R$_4$ is absent or methyl;

R$_5$ is aryl or heteroaryl each optionally substituted with one or more substituents selected from R$_b$;

R$_6$ is absent or F;

R$_a$ is independently selected from: F, O$_b$(C$_1$-C$_4$)alkyl, SO$_2$(C$_1$-C$_4$)alkyl, C(O)C$_1$-C$_4$ alkyl, said alkyl optionally substituted with F or morpholinyl;

R$_b$ is independently selected from OH, halo, CHF$_2$, CF$_3$, COOH, SO$_2$(C$_1$-C$_4$)alkyl, C=O(O)C$_1$-C$_4$ alkyl, O$_b$(C$_1$-C$_4$)alkyl, aryl, heterocyclyl, CN, C(O)N(R$_c$)$_2$, N(R$_c$)$_2$; said R$_c$ and alkyl are optionally substituted with OH, O(C$_1$-C$_4$)alkyl and heterocyclyl; and R$_c$ is independently H, SO$_2$(C$_1$-C$_4$)alkyl, or C$_1$-C$_4$ alkyl; or a pharmaceutically acceptable salt or a stereoisomer thereof.

A compound of the instant invention is selected from:

trans-N,N-dimethyl-N'-[6-(6-methylpyridazin-4-yl)quinazolin-4-yl]cyclohexane-1,4-diamine (1);

cis or trans-N,N-dimethyl-N'-(6-phenylquinazolin-4-yl)cyclohexane-1,4-diamine (2);

cis or trans-N,N-dimethyl-N'-[6-(pyridin-4-yl)quinazolin-4-yl]cyclohexane-1,4-diamine (3);

cis or trans-N,N-dimethyl-N'-[6-(pyridin-3-yl)quinazolin-4-yl]cyclohexane-1,4-diamine (4);

cis or trans-N,N-dimethyl-N'-(6-phenylquinazolin-4-yl)cyclohexane-1,4-diamine (5);

cis or trans-N,N-dimethyl-N'-[6-(pyridin-4-yl)quinazolin-4-yl]cyclohexane-1,4-diamine (6);

cis or trans-N,N-dimethyl-N'-[6-(pyridin-3-yl)quinazolin-4-yl]cyclohexane-1,4-diamine (7);

trans-N'-[6-(2-methoxypyridin-4-yl)quinazolin-4-yl]-N,N-dimethylcyclohexane-1,4-diamine (8);

trans-N,N-dimethyl-N'-[6-(1-methyl-1H-pyrazol-4-yl)quinazolin-4-yl]cyclohexane-1,4-diamine (9);

cis or trans-N,N-dimethyl-N'-[6-(1H-pyrazol-4-yl)quinazolin-4-yl]cyclohexane-1,4-diamine (10);

cis or trans-N'-[6-(6-aminopyridin-3-yl)quinazolin-4-yl]-N,N-dimethylcyclohexane-1,4-diamine (11);

trans-N,N-dimethyl-N'-[6-(1H-pyrazol-3-yl)quinazolin-4-yl]cyclohexane-1,4-diamine (12);

trans-N,N-dimethyl-N'-{6-[2-(methylamino)pyrimidin-5-yl]quinazolin-4-yl}cyclohexane-1,4-diamine (13);

trans-N'-{6-[1-(1-ethoxyethyl)-1H-pyrazol-4-yl]quinazolin-4-yl}-N,N-dimethylcyclohexane-1,4-diamine (14);

trans-N,N-dimethyl-N'-(6-{1-[2-(morpholin-4-yl)ethyl]-1H-pyrazol-4-yl}quinazolin-4-yl)cyclohexane-1,4-diamine (15);

trans-N,N-dimethyl-N'-{6-[1-(tetrahydro-2H-pyran-2-yl)-1H-pyrazol-4-yl]quinazolin-4-yl}cyclohexane-1,4-diamine (16);

trans-N,N-dimethyl-N'-{6-[1-(pyridin-2-ylmethyl)-1H-pyrazol-4-yl]quinazolin-4-yl}cyclohexane-1,4-diamine (17);

trans-N'-[6-(1-ethyl-1H-pyrazol-4-yl)quinazolin-4-yl]-N,N-dimethylcyclohexane-1,4-diamine (18);

trans-N,N-dimethyl-N'-{6-[1-(pyridin-4-ylmethyl)-1H-pyrazol-4-yl]quinazolin-4-yl}cyclohexane-1,4-diamine (19);

4-(4-{[trans-4-(dimethylamino)cyclohexyl]amino}quinazolin-6-yl)pyridine-3-carbonitrile (20);

trans-N,N-dimethyl-N'-[6-(3-methylpyridin-4-yl)quinazolin-4-yl]cyclohexane-1,4-diamine (21);

3-(4-{[trans-4-(dimethylamino)cyclohexyl]amino}quinazolin-6-yl)pyridine-4-carbonitrile (22);

trans-N,N-dimethyl-N'-{6-[5-(morpholin-4-yl)pyridin-3-yl]quinazolin-4-yl}cyclohexane-1,4-diamine (23);

trans-N'-[6-(3,5-dimethylisoxazol-4-yl)quinazolin-4-yl]-N,N-dimethylcyclohexane-1,4-diamine (24);

trans-N,N-dimethyl-N'-[6-(pyrimidin-5-yl)quinazolin-4-yl]cyclohexane-1,4-diamine (25);

trans-N,N-dimethyl-N'-[6-(5-methyl-3-phenylisoxazol-4-yl)quinazolin-4-yl]cyclohexane-1,4-diamine (26);

5-(4-{[trans-4-(dimethylamino)cyclohexyl]amino}quinazolin-6-yl)pyridine-2-carbonitrile (27);

5-(4-{[trans-4-(dimethylamino)cyclohexyl]amino}quinazolin-6-yl)pyridin-2-ol (28);

trans-N'-[6-(2-aminopyrimidin-5-yl)quinazolin-4-yl]-N,N-dimethylcyclohexane-1,4-diamine (29);

trans-N,N-dimethyl-N'-[6-(6-methylpyridin-3-yl)quinazolin-4-yl]cyclohexane-1,4-diamine (30);

methyl 5-(4-{[trans-4-(dimethylamino)cyclohexyl]amino}quinazolin-6-yl)pyridine-3-carboxylate (31);

trans-N'-[6-(isoxazol-4-yl)quinazolin-4yl]-N,N-dimethylcyclohexane-1,4-diamine (32);

5-(4-{[trans-4-(dimethylamino)cyclohexyl]amino}quinazolin-6-yl)pyrimidin-2-ol (33);

trans-N'-[6-(3-fluoropyridin-4-yl)quinazolin-4-yl]-N,N-dimethylcyclohexane-1,4-diamine (34);

trans-N'-[6-(4-methoxypyridin-3-yl)quinazolin-4-yl]-N,N-dimethylcyclohexane-1,4-diamine (35);
trans-N,N-dimethyl-N'-{6-[4-(trifluoromethyl)pyridin-3-yl]quinazolin-4-yl}cyclohexane-1,4-diamine (36);
5-(4-{[trans-4-(dimethylamino)cyclohexyl]amino}quinazolin-6-yl)pyridine-3-carboxylic acid (37);
trans-N'-[6-(3-methoxypyridin-4-yl)quinazolin-4-yl]-N,N-dimethylcyclohexane-1,4-diamine (38);
3-(4-{[trans-4-(dimethylamino)cyclohexyl]amino}quinazolin-6-yl)pyridine-2-carbonitrile (39);
trans-N'-{6-[5-(2-methoxyethoxy)pyridin-3-yl]quinazolin-4-yl}-N,N-dimethylcyclohexane-1,4-diamine (40);
trans-N,N-dimethyl-N'-{6-[5-(methylsulfonyl)pyridin-3-yl]quinazolin-4-yl}cyclohexane-1,4-diamine (41);
trans-N'-{6-[2-(cyclopropylamino)pyrimidin-5-yl]quinazolin-4-yl}-N,N-dimethylcyclohexane-1,4-diamine (42);
2-{[5-(4-{[trans-4-(dimethylamino)cyclohexyl]amino}quinazolin-6-yl)pyrimidin-2-yl]amino}ethanol (43);
3-(4-{[trans-4-(dimethylamino)cyclohexyl]amino}quinazolin-6-yl)benzonitrile (44);
trans-N'-[6-(1H-indol-5-yl)quinazolin-4-yl]-N,N-dimethylcyclohexane-1,4-diamine (45);
N-[trans-4-(morpholin-4-yl)cyclohexyl]-6-(pyridin-3-yl)quinazolin-4-amine (46);
N-[trans-4-(morpholin-4-yl)cyclohexyl]-6-(pyrimidin-5-yl)quinazolin-4-amine (47);
N-[trans-4-(morpholin-4-yl)cyclohexyl]-6-(pyridin-4-yl)quinazolin-4-amine (48);
trans-N'-[6-(2,3-dihydro-1,4-benzodioxin-6-yl)quinazolin-4-yl]-N,N-dimethylcyclohexane-1,4-diamine (49);
trans-N,N-dimethyl-N'-[6-(pyridazin-4-yl)quinazolin-4-yl]cyclohexane-1,4-diamine (50);
trans-N'-[6-(5-methoxypyridin-3-yl)quinazolin-4-yl]-N,N-dimethylcyclohexane-1,4-diamine (51);
trans-N'-[6-(5-fluoro-6-methoxypyridin-3-yl)quinazolin-4-yl]-N,N-dimethylcyclohexane-1,4-diamine (52);
trans-N'-[6-(5-fluoropyridin-3-yl)quinazolin-4-yl]-N,N-dimethylcyclohexane-1,4-diamine (53);
5-(4-{[trans-4-(dimethylamino)cyclohexyl]amino}quinazolin-6-yl)pyridine-3-carbonitrile (54);
trans-N,N-dimethyl-N'-[6-(1H-pyrrolo[2,3-b]pyridin-5-yl)quinazolin-4-yl]cyclohexane-1,4-diamine (55);
N-tert-butyl-5-(4-{[trans-4-(dimethylamino)cyclohexyl]amino}quinazolin-6-yl)pyridine-3-carboxamide (56);
trans-N,N-dimethyl-N'-[6-(4-methyl-3,4-dihydro-2H-pyrido[3,2-b][1,4]oxazin-7-yl)quinazolin-4-yl]cyclohexane-1,4-diamine (57);
trans-N,N-dimethyl-N'-[6-(1H-pyrazolo[3,4-b]pyridin-5-yl)quinazolin-4-yl]cyclohexane-1,4-diamine (58);
trans-N,N-dimethyl-N'-[6-(1H-pyrrolo[3,2-b]pyridin-6-yl)quinazolin-4-yl]cyclohexane-1,4-diamine (59);
trans-N,N-dimethyl-N'-[6-(3-methyl-3H-imidazo[4,5-b]pyridin-6-yl)quinazolin-4-yl]cyclohexane-1,4-diamine (60);
trans-N'-[6-(furo[3,2-b]pyridin-6-yl)quinazolin-4-yl]-N,N-dimethylcyclohexane-1,4-diamine (61);
trans-N'-[6-(3,5-difluorophenyl)quinazolin-4-yl]-N,N-dimethylcyclohexane-1,4-diamine (62);
3-(4-{[trans-4-(dimethylamino)cyclohexyl]amino}quinazolin-6-yl)-5-fluorophenol (63);
5-(4-{[trans-4-(dimethylamino)cyclohexyl]amino}quinazolin-6-yl)-2,3-difluorophenol (64);
5-(4-{[trans-4-(morpholin-4-yl)cyclohexyl]amino}quinazolin-6-yl)pyridin-3-ol (65);
3-fluoro-5-{4-[(trans-4-morpholin-4-ylcyclohexyl)amino]quinazolin-6-yl}phenol (66);
4-{4-[(trans-4-morpholin-4-ylcyclohexyl)amino]quinazolin-6-yl}pyridin-2-ol (67);
6-(3,5-difluorophenyl)-N-(trans-4-morpholin-4-ylcyclohexyl)quinazolin-4-amine (68);
6-(5-methoxypyridin-3-yl)-N-[trans-4-(morpholin-4-yl)cyclohexyl]quinazolin-4-amine (69);
2,3-difluoro-5-{4-[(trans-4-morpholin-4-ylcyclohexyl)amino]quinazolin-6-yl}phenol (70);
6-(5-amino-6-methoxypyridin-3-yl)-N-(trans-4-morpholin-4-ylcyclohexyl)quinazolin-4-amine (71);
3-{4-[(trans-4-morpholin-4-ylcyclohexyl)amino]quinazolin-6-yl}phenol (72);
6-(5-aminopyridin-3-yl)-N-(trans-4-morpholin-4-ylcyclohexyl)quinazolin-4-amine (73);
6-(2-aminopyridin-4-yl)-N-(trans-4-morpholin-4-ylcyclohexyl)quinazolin-4-amine (74);
6-(1-methyl-1H-pyrazol-4-yl)-N-(trans-4-morpholin-4-ylcyclohexyl)quinazolin-4-amine (75);
5-methyl-N-(trans-4-morpholin-4-ylcyclohexyl)-6-pyrimidin-5-ylquinazolin-4-amine (76);
5-methyl-6-(1-methyl-1H-pyrazol-4-yl)-N-(trans-4-morpholin-4-ylcyclohexyl)quinazolin-4-amine (77);
5-methyl-N-(trans-4-morpholin-4-ylcyclohexyl)-6-ylquinazolin-4-amine (78);
5-{5-methyl-4-[(trans-4-morpholin-4-ylcyclohexyl)amino]quinazolin-6-yl}pyridin-3-ol (79);
7-fluoro-N-(trans-4-morpholin-4-ylcyclohexyl)-6-(1H-pyrazol-4-yl)quinazolin-4-amine (80);
6-[5-(methylamino)pyridin-3-yl]-N-(trans-4-morpholin-4-ylcyclohexyl)quinazolin-4-amine (81);
N-(trans-4-morpholin-4-ylcyclohexyl)-6-(1H-pyrazol-4-yl)quinazolin-4-amine (82);
6-(3-aminophenyl)-N-(trans-4-morpholin-4-ylcyclohexyl)quinazolin-4-amine (83);
5-{7-fluoro-4-[(trans-4-morpholin-4-ylcyclohexyl)amino]quinazolin-6-yl}pyridin-3-ol (84);
6-(5-aminopyridin-3-yl)-7-fluoro-N-(trans-4-morpholin-4-ylcyclohexyl)quinazolin-4-amine (85);
7-fluoro-6-[5-(methylamino)pyridin-3-yl]-N-(trans-4-morpholin-4-ylcyclohexyl)quinazolin-4-amine (86);
7-fluoro-N-(trans-4-morpholin-4-ylcyclohexyl)-6-pyrimidin-5-ylquinazolin-4-amine (87);
6-(1H-indol-4-yl)-N-[trans-4-(morpholin-4-yl)cyclohexyl]quinazolin-4-amine (88);
6-(2-methylpyrimidin-5-yl)-N-[trans-4-(morpholin-4-yl)cyclohexyl]quinazolin-4-amine (89);
N-[cis-4-(morpholin-4-yl)cyclohexyl]-6-[2-(trifluoromethyl)pyrimidin-5-yl]quinazolin-4-amine (90);
N-[trans-4-(morpholin-4-yl)cyclohexyl]-6-(1H-pyrazol-3-yl)quinazolin-4-amine (91);
N-[5-(4-{[trans-4-(morpholin-4-yl)cyclohexyl]amino}quinazolin-6-yl)pyridin-3-yl]methanesulfonamide (92);
6-(5-methylpyridin-3-yl)-N-[trans-4-(morpholin-4-yl)cyclohexyl]quinazolin-4-amine (93);
[5-(4-{[trans-4-(morpholin-4-yl)cyclohexyl]amino}quinazolin-6-yl)pyridin-3-yl]methanol (94);
2-[5-(4-{[trans-4-(morpholin-4-yl)cyclohexyl]amino}quinazolin-6-yl)pyridin-3-yl]propan-2-ol (95);
6-(isoxazol-4-yl)-N-[trans-4-(morpholin-4-yl)cyclohexyl]quinazolin-4-amine (96);
6-(5-fluoropyridin-3-yl)-N-[trans-4-(morpholin-4-yl)cyclohexyl]quinazolin-4-amine (97);
5-(4-{[trans-4-(morpholin-4-yl)cyclohexyl]amino}quinazolin-6-yl)pyridine-3-carbonitrile (98);
6-(5-chloropyridin-3-yl)-N-[trans-4-(morpholin-4-yl)cyclohexyl]quinazolin-4-amine (99);

2-chloro-5-(4-{[trans-4-(morpholin-4-yl)cyclohexyl]
amino}quinazolin-6-yl)pyridin-3-ol (100);
ethyl 1-methyl-3-(4-(((trans)-4-morpholinocyclohexyl)
amino)quinazolin-6-yl)-1H-pyrazole-4-carboxylate
(101);
6-(2-methyl-1,3-thiazol-4-yl)-N-(trans-4-morpholin-4-ylcyclohexyl)quinazolin-4-amine (102);
6-[2-(1-methylethyl)-1,3-thiazol-4-yl]-N-(trans-4-morpholin-4-ylcyclohexyl)quinazolin-4-amine (103);
N-(trans-4-morpholin-4-ylcyclohexyl)-6-[5-(trifluoromethyl)pyridin-3-yl]quinazolin-4-amine (104);
3-{4-[(trans-4-morpholin-4-ylcyclohexyl)amino]quinazolin-6-yl}-5-(trifluoromethyl)pyridin-2-ol (105);
2-chloro-5-{4-[(trans-4-morpholin-4-ylcyclohexyl)amino]
quinazolin-6-yl}pyridin-3-ol (106);
6-(5-amino-6-fluoropyridin-3-yl)-N-(trans-4-morpholin-4-ylcyclohexyl)quinazolin-4-amine (107);
6-{4-[(trans-4-morpholin-4-ylcyclohexyl)amino]quinazolin-6-yl}-pyridine-2-carboxylic acid (108);
6-(4-fluoro-1H-pyrazol-3-yl)-N-(trans-4-morpholin-4-ylcyclohexyl)quinazolin-4-amine (109);
4-{4-[(trans-4-morpholin-4-ylcyclohexyl)amino]quinazolin-6-yl}-1H-pyrazole-3-carbonitrile (110);
5-{4-[(trans-4-morpholin-4-ylcyclohexyl)amino]quinazolin-6-yl}-1H-1,2,3-triazole-4-carbonitrile (111);
(1-methyl-4-{4-[(trans-4-morpholin-4-ylcyclohexyl)amino]
quinazolin-6-yl}-1H-pyrazol-3-yl)methanol (112);
6-(1-methyl-1H-pyrazol-5-yl)-N-(trans-4-morpholin-4-ylcyclohexyl)quinazolin-4-amine (113);
N-(trans-4-morpholin-4-ylcyclohexyl)-6-[3-(trifluoromethyl)-1H-pyrazol-4-yl]quinazolin-4-amine (114);
6-(1-methyl-1H-1,2,3-triazol-5-yl)-N-(trans-4-morpholin-4-ylcyclohexyl)quinazolin-4-amine (115);
6-(2,3-dihydro-1H-pyrrolo[3,2-b]pyridin-6-yl)-N-[trans-4-(morpholin-4-yl)cyclohexyl]quinazolin-4-amine (116);
3-(4-{[trans-4-(morpholin-4-yl)cyclohexyl]
amino}quinazolin-6-yl)thiophene-2-carbonitrile (117);
4-(4-{[trans-4-(morpholin-4-yl)cyclohexyl]
amino}quinazolin-6-yl)thiophene-3-carbonitrile (118);
6-(4-methyl-1H-imidazol-5-yl)-N-[trans-4-(morpholin-4-yl)cyclohexyl]quinazolin-4-amine (119);
6-(3-methyl-1H-pyrazol-4-yl)-N-[trans-4-(morpholin-4-yl)cyclohexyl]quinazolin-4-amine (120);
6-(1,5-dimethyl-1H-pyrazol-4-yl)-N-[trans-4-(morpholin-4-yl)cyclohexyl]quinazolin-4-amine (121);
6-(4-methyl-1H-imidazol-2-yl)-N-[trans-4-(morpholin-4-yl)cyclohexyl]quinazolin-4-amine (122);
6-(1,4-dimethyl-1H-imidazol-2-yl)-N-[trans-4-(morpholin-4-yl)cyclohexyl]quinazolin-4-amine (123);
6-(3,5-dimethyl-1H-pyrazol-4-yl)-N-[trans-4-(morpholin-4-yl)cyclohexyl]quinazolin-4-amine (124);
6-(2-methyl-1H-imidazol-4-yl)-N-[trans-4-(morpholin-4-yl)cyclohexyl]quinazolin-4-amine (125);
6-(2-cyclopropyl-1-methyl-1H-imidazol-5-yl)-N-[trans-4-(morpholin-4-yl)cyclohexyl]quinazolin-4-amine (126);
6-(1-methyl-1H-imidazol-2-yl)-N-[trans-4-(morpholin-4-yl)cyclohexyl]quinazolin-4-amine (127);
6-(1-methyl-1H-1,2,4-triazol-5-yl)-N-[trans-4-(morpholin-4-yl)cyclohexyl]quinazolin-4-amine (128);
6-(isoxazol-4-yl)-N-[trans-4-(morpholin-4-yl)cyclohexyl]
quinazolin-4-amine (129);
6-(6-fluoro-5-methoxypyridin-3-yl)-N-[trans-4-(morpholin-4-yl)cyclohexyl]quinazolin-4-amine (130);
2-fluoro-5-(4-{[trans-4-(morpholin-4-yl)cyclohexyl]
amino}quinazolin-6-yl)pyridin-3-ol (131);
6-[5-(dimethylamino)-6-fluoropyridin-3-yl]-N-[trans-4-(morpholin-4-yl)cyclohexyl]quinazolin-4-amine (132);
6-[6-fluoro-5-(methylamino)pyridin-3-yl]-N-[trans-4-(morpholin-4-yl)cyclohexyl]quinazolin-4-amine (133);
6-(6-chloro-5-fluoropyridin-3-yl)-N-[trans-4-(morpholin-4-yl)cyclohexyl]quinazolin-4-amine (134);
6-(5,6-difluoropyridin-3-yl)-N-[trans-4-(morpholin-4-yl)
cyclohexyl]quinazolin-4-amine (135);
6-[5-(difluoromethyl)pyridin-3-yl]-N-[trans-4-(morpholin-4-yl)cyclohexyl]quinazolin-4-amine (136);
6-(5-amino-6-chloropyridin-3-yl)-N-[trans-4-(morpholin-4-yl)cyclohexyl]quinazolin-4-amine (137);
5-(4-(((trans)-4-(dimethylamino)cyclohexyl)amino)quinazolin-6-yl)pyridin-3-ol (138);
N,N-dimethyl-6-(4-(((trans)-4-morpholinocyclohexyl)
amino)quinazolin-6-yl)picolinamide (139);
5-(4-{[trans-4-(4,4-difluoropiperidin-1-yl)cyclohexyl]
amino}quinazolin-6-yl)-2-fluoropyridin-3-ol (140);
5-(4-{[trans-4-(3-methoxyazetidin-1-yl)cyclohexyl]
amino}quinazolin-6-yl)pyridin-3-ol (141);
5-[4-({trans-4-[cyclopropyl(methyl)amino]
cyclohexyl}amino)quinazolin-6-yl]pyridin-3-ol (142);
5-(4-({trans-4-[(2-methoxyethyl)amino]cyclohexyl}amino)
quinazolin-6-yl)pyridin-3-ol (143);
5-(4-{[trans-4-(4-methylpiperazin-1-yl)cyclohexyl]
amino}quinazolin-6-yl)pyridin-3-ol (144);
5-[4-({trans-4-[(2R,6S)-2,6-dimethylmorpholin-4-yl]
cyclohexyl}amino)quinazolin-6-yl]pyridin-3-ol (145);
6-[5-(methylamino)pyridin-3-yl]-N-{trans-4-[4-(methylsulfonyl)piperazin-1-yl]cyclohexyl}quinazolin-4-amine (146);
N-[trans-4-(4,4-difluoropiperidin-1-yl)cyclohexyl]-6-[5-(methylamino)pyridin-3-yl]quinazolin-4-amine (147);
N-[trans-4-(4-fluoropiperidin-1-yl)cyclohexyl]-6-[5-(methylamino)pyridin-3-yl]quinazolin-4-amine (148);
6-[5-(methylamino)pyridin-3-yl]-N-{trans-4-[4-(morpholin-4-ylmethyl)piperidin-1-yl]cyclohexyl}quinazolin-4-amine (149);
6-[5-(methylamino)pyridin-3-yl]-N-{trans-4-[(3R)-3-(morpholin-4-ylmethyl)piperidin-1-yl]cyclohexyl}quinazolin-4-amine (150);
6-[5-(methylamino)pyridin-3-yl]-N-{trans-4-[(3S)-3-(morpholin-4-ylmethyl)piperidin-1-yl]cyclohexyl}quinazolin-4-amine (151);
2-fluoro-5-(4-{[trans-4-(4-fluoropiperidin-1-yl)cyclohexyl]
amino}quinazolin-6-yl)pyridin-3-ol (152);
2-fluoro-5-[4-({trans-4-[4-(methylsulfonyl)piperazin-1-yl]
cyclohexyl}amino)quinazolin-6-yl]pyridin-3-ol (153);
6-(5-amino-6-fluoropyridin-3-yl)-N-[trans-4-(4,4-difluoropiperidin-1-yl)cyclohexyl]quinazolin-4-amine (154);
6-(5-amino-6-fluoropyridin-3-yl)-N-[trans-4-(4-fluoropiperidin-1-yl)cyclohexyl]quinazolin-4-amine (155);
5-(4-{[trans-4-(4,4-difluoropiperidin-1-yl)cyclohexyl]
amino}quinazolin-6-yl)pyridin-3-ol (156);
5-(4-{[trans-4-(4-fluoropiperidin-1-yl)cyclohexyl]
amino}quinazolin-6-yl)pyridin-3-ol (157);
6-(5-amino-6-fluoropyridin-3-yl)-N-{trans-4-[(2R,6S)-2,6-dimethylmorpholin-4-yl]cyclohexyl}quinazolin-4-amine (158);
6-(5-amino-6-fluoropyridin-3-yl)-N-{trans-4-[4-(methylsulfonyl)piperazin-1-yl]cyclohexyl}quinazolin-4-amine (159);
6-(5-amino-6-fluoropyridin-3-yl)-N-{trans-4-[3-(morpholin-4-ylmethyl)piperidin-1-yl]cyclohexyl}quinazolin-4-amine (160);
6-(5-amino-6-fluoropyridin-3-yl)-N-{trans-4-[(2R)-2-(fluoromethyl)morpholin-4-yl]cyclohexyl}quinazolin-4-amine (161);

6-(5-amino-6-fluoropyridin-3-yl)-N-{trans-4-[(2S)-2-(fluoromethyl)morpholin-4-yl]cyclohexyl}quinazolin-4-amine (162);

6-(5-amino-6-fluoropyridin-3-yl)-N-{trans-4-[(2R)-2-methylmorpholin-4-yl]cyclohexyl}quinazolin-4-amine (163);

6-(5-amino-6-fluoropyridin-3-yl)-N-{trans-4-[(2S)-2-methylmorpholin-4-yl]cyclohexyl}quinazolin-4-amine (164);

N-{trans-4-[(2R,6S)-2,6-dimethylmorpholin-4-yl]cyclohexyl}-6-[6-fluoro-5-(methylamino)pyridin-3-yl]quinazolin-4-amine (165);

N-[trans-4-(4,4-difluoropiperidin-1-yl)cyclohexyl]-6-[6-fluoro-5-(methylamino)pyridin-3-yl]quinazolin-4-amine (166);

cyclopropyl {4-[trans-4-({6-[6-fluoro-5-(methylamino)pyridin-3-yl]quinazolin-4-yl}amino)cyclohexyl]piperazin-1-yl}methanone (167);

6-[6-fluoro-5-(methylamino)pyridin-3-yl]-N-[trans-4-(4-fluoropiperidin-1-yl)cyclohexyl]quinazolin-4-amine (168);

6-[6-fluoro-5-(methylamino)pyridin-3-yl]-N-{trans-4-[(2R)-2-methylmorpholin-4-yl]cyclohexyl}quinazolin-4-amine (169);

6-[6-fluoro-5-(methylamino)pyridin-3-yl]-N-{trans-4-[(2S)-2-methylmorpholin-4-yl]cyclohexyl}quinazolin-4-amine (170);

or a pharmaceutically acceptable salt or stereoisomer thereof.

The compounds of the present invention may have asymmetric centers, chiral axes, and chiral planes (as described in: E. L. Eliel and S. H. Wilen, *Stereochemistry of Carbon Compounds*, John Wiley & Sons, New York, 1994, pages 1119-1190), and occur as racemates, racemic mixtures, and as individual diastereomers, with all possible isomers and mixtures thereof, including optical isomers, all such stereoisomers being included in the present invention.

In addition, the compounds disclosed herein may exist as tautomers and both tautomeric forms are intended to be encompassed by the scope of the invention, even though only one tautomeric structure is depicted.

This invention is also intended to encompass pro-drugs of the compounds disclosed herein. A prodrug of any of the compounds can be made using well known pharmacological techniques.

When any variable (e.g. $R_3$, etc.) occurs more than one time in any constituent, its definition on each occurrence is independent at every other occurrence. Also, combinations of substituents and variables are permissible only if such combinations result in stable compounds. Lines drawn into the ring systems from substituents represent that the indicated bond may be attached to any of the substitutable ring atoms. If the ring system is bicyclic, it is intended that the bond be attached to any of the suitable atoms on either ring of the bicyclic moiety. When $R_4$ and/or $R_6$ are "absent" it is understood that a hydrogen atom is present.

In the compounds of Formula I and II, the atoms may exhibit their natural isotopic abundances, or one or more of the atoms may be artificially enriched in a particular isotope having the same atomic number, but an atomic mass or mass number different from the atomic mass or mass number predominantly found in nature. The present invention is meant to include all suitable isotopic variations of the compounds of Formula I and II. For example, different isotopic forms of hydrogen (H) include protium ($^1H$) and deuterium ($^2H$). Protium is the predominant hydrogen isotope found in nature. Enriching for deuterium may afford certain therapeutic advantages, such as increasing in vivo half-life or reducing dosage requirements, or may provide a compound useful as a standard for characterization of biological samples. Isotopically-enriched compounds within Formulas I and II can be prepared without undue experimentation by conventional techniques well known to those skilled in the art or by processes analogous to those described in the Scheme and Examples herein using appropriate isotopically-enriched reagents and/or intermediates.

It is understood that one or more silicon (Si) atoms can be incorporated into the compounds of the instant invention in place of one or more carbon atoms by one of ordinary skill in the art to provide compounds that are chemically stable and that can be readily synthesized by techniques known in the art from readily available starting materials. Carbon and silicon differ in their covalent radius leading to differences in bond distance and the steric arrangement when comparing analogous C-element and Si-element bonds. These differences lead to subtle changes in the size and shape of silicon-containing compounds when compared to carbon. One of ordinary skill in the art would understand that size and shape differences can lead to subtle or dramatic changes in potency, solubility, lack of off target activity, packaging properties, and so on. (Diass, J. O. et al. Organometallics (2006) 5:1188-1198; Showell, G. A. et al. Bioorganic & Medicinal Chemistry Letters (2006) 16:2555-2558).

It is understood that substituents and substitution patterns on the compounds of the instant invention can be selected by one of ordinary skill in the art to provide compounds that are chemically stable and that can be readily synthesized by techniques known in the art, as well as those methods set forth below, from readily available starting materials. If a substituent is itself substituted with more than one group, it is understood that these multiple groups may be on the same carbon or on different carbons, so long as a stable structure results. In some instances, two substituents are attached to the same carbon and come together to form a carbocyclic or heterocyclic ring (a spirocyclic ring system).

As used herein, "alkyl" is intended to include branched, cyclic and straight-chain saturated aliphatic hydrocarbon groups having the specified number of carbon atoms. For example, $C_1$-$C_4$, as in "($C_1$-$C_4$)alkyl" is defined to include groups having 1, 2, 3, and 4 carbon atoms in a linear, cyclic or branched arrangement. For example, "($C_1$-$C_4$)alkyl" specifically includes methyl, ethyl, n-propyl, i-propyl, n-butyl, t-butyl, i-butyl, cyclopropyl, and cyclobutyl.

The term, "aryl" is intended to mean any stable monocyclic or bicyclic carbon ring of up to 7 atoms in each ring, wherein at least one ring is aromatic. Examples of such aryl elements include phenyl, naphthyl, tetrahydro-naphthyl, indanyl and biphenyl. In cases where the aryl substituent is bicyclic and one ring is non-aromatic, it is understood that attachment is via the aromatic ring. Aryl specifically includes phenyl.

The term "heteroaryl", as used herein, represents a stable monocyclic or bicyclic ring of up to 7 atoms in each ring, wherein at least one ring is aromatic and contains from 1 to 4 heteroatoms selected from the group consisting of O, N and S. Heteroaryl groups within the scope of this definition include but are not limited to: acridinyl, carbazolyl, cinnolinyl, quinoxalinyl, pyrazolyl, indolyl, benzotriazolyl, furanyl, thienyl, benzothienyl, benzofuranyl, quinolinyl, isoquinolinyl, oxazolyl, isoxazolyl, pyrazinyl, pyridazinyl, pyridinyl, pyrimidinyl, pyrrolyl, tetrahydroquinoline, dihydrobenzodioxinyl, pyrrolopyridinyl, dihydropyridooxazinyl, pyrazolopyridinyl, imidazolpyridinyl, furopyridinyl, thiazolyl, triazolyl, dihydropyrrolopyridinyl, thiophenyl and imidazolyl. Heteroaryl groups specifically include: pyrazolyl, indolyl, isoxazolyl, pyridazinyl, pyridinyl, pyrimidinyl, dihydrobenzodioxinyl, pyrrolopyridinyl, dihydropyridooxazinyl, pyrazolopyridinyl, imidazolpyridinyl, furopyridinyl, thiazolyl, triazolyl, dihydropyrrolopyridinyl, thiophenyl and imidazolyl. As with the definition of heterocycle below, "heteroaryl" is also understood to include the N-oxide derivative of any nitrogen-containing heteroaryl. In cases where the heteroaryl substituent is bicyclic and one ring is non-aromatic or contains no heteroatoms, it is understood that attachment is via the aromatic ring or via the heteroatom containing ring, respectively.

The term "heterocycle" or "heterocyclyl" as used herein is intended to mean a 3- to 10-membered aromatic heterocycle containing from 1 to 4 heteroatoms selected from the group consisting of O, N and S, and includes monocyclic or bicyclic groups (fused, bridged or spirocyclic). Further examples of "heterocyclyl" include, but are not limited to the following: benzoimidazolyl, benzoimidazolonyl, benzofuranyl, benzofurazanyl, benzopyrazolyl, benzotriazolyl, benzothiophenyl, benzoxazolyl, carbazolyl, carbolinyl, cinnolinyl, furanyl, imidazolyl, indolinyl, indolyl, indolazinyl, indazolyl, isobenzofuranyl, isoindolyl, isoquinolyl, isothiazolyl, isoxazolyl, naphthpyridinyl, oxadiazolyl, oxazolyl, oxazoline, isoxazoline, oxetanyl, pyranyl, pyrazinyl, pyrazolyl, pyridazinyl, pyridopyridinyl, pyridazinyl, pyridyl, pyrimidyl, pyrrolyl, quinazolinyl, quinolyl, quinoxalinyl, tetrahydropyranyl, tetrazolyl, tetrazolopyridyl, thiadiazolyl, thiazolyl, thienyl, triazolyl, azetidinyl, 1,4-dioxanyl, hexahydroazepinyl, piperazinyl, piperidinyl, pyridin-2-onyl, pyrrolidinyl, morpholinyl, thiomorpholinyl, dihydrobenzoimidazolyl, dihydrobenzofuranyl, dihydrobenzothiophenyl, dihydrobenzoxazolyl, dihydrofuranyl, dihydroimidazolyl, dihydroindolyl, dihydroisooxazolyl, dihydroisothiazolyl, dihydrooxadiazolyl, dihydrooxazolyl, dihydropyrazinyl, dihydropyrazolyl, dihydropyridinyl, dihydropyrimidinyl, dihydropyrrolyl, dihydroquinolinyl, dihydrotetrazolyl, dihydrothiadiazolyl, dihydrothiazolyl, dihydrothienyl, dihydrotriazolyl, dihydroazetidinyl, methylenedioxybenzoyl, tetrahydrofuranyl, and tetrahydrothienyl, and N-oxides thereof. Attachment of a heterocyclyl substituent can occur via a carbon atom or via a heteroatom.

In one embodiment of Formula I and II, heterocyclyl is independently selected from benzoimidazolyl, benzoimidazolonyl, benzofuranyl, benzofurazanyl, benzopyrazolyl, benzotriazolyl, benzothiophenyl, benzoxazolyl, carbazolyl, carbolinyl, cinnolinyl, furanyl, imidazolyl, indolinyl, indolyl, indolazinyl, indazolyl, isobenzofuranyl, isoindolyl, isoquinolyl, isothiazolyl, isoxazolyl, naphthpyridinyl, oxadiazolyl, oxazolyl, oxazoline, isoxazoline, oxetanyl, pyranyl, pyrazinyl, pyrazolyl, pyridazinyl, pyridopyridinyl, pyridazinyl, pyridyl, pyrimidyl, pyrrolyl, quinazolinyl, quinolyl, quinoxalinyl, tetrahydropyranyl, tetrazolyl, tetrazolopyridyl, thiadiazolyl, thiazolyl, thienyl, triazolyl, azetidinyl, 1,4-dioxanyl, hexahydroazepinyl, piperazinyl, piperidinyl, pyridin-2-onyl, pyrrolidinyl, morpholinyl, thiomorpholinyl, dihydrobenzoimidazolyl, dihydrobenzofuranyl, dihydrobenzothiophenyl, dihydrobenzoxazolyl, dihydrofuranyl, dihydroimidazolyl, dihydroindolyl, dihydroisooxazolyl, dihydroisothiazolyl, dihydrooxadiazolyl, dihydrooxazolyl, dihydropyrazinyl, dihydropyrazolyl, dihydropyridinyl, dihydropyrimidinyl, dihydropyrrolyl, dihydroquinolinyl, dihydrotetrazolyl, dihydrothiadiazolyl, dihydrothiazolyl, dihydrothienyl, dihydrotriazolyl, dihydroazetidinyl, methylenedioxybenzoyl, tetrahydrofuranyl, and tetrahydrothienyl, and N-oxides thereof.

In another embodiment of Formula I and II, heterocyclyl is independently selected from benzoimidazolyl, benzoimidazolonyl, benzofuranyl, benzofurazanyl, benzopyrazolyl, benzotriazolyl, benzothiophenyl, benzoxazolyl, carbazolyl, carbolinyl, cinnolinyl, furanyl, imidazolyl, indolinyl, indolyl, indolazinyl, indazolyl, isobenzofuranyl, isoindolyl, isoquinolyl, isothiazolyl, isoxazolyl, naphthpyridinyl, oxadiazolyl, oxazolyl, oxazoline, isoxazoline, oxetanyl, pyranyl, pyrazinyl, pyrazolyl, pyridazinyl, pyridopyridinyl, pyridazinyl, pyridyl, pyrimidyl, pyrrolyl, quinazolinyl, quinolyl, quinoxalinyl, tetrahydropyranyl, tetrazolyl, tetrazolopyridyl, thiadiazolyl, thiazolyl, thienyl, triazolyl, azetidinyl, 1,4-dioxanyl, hexahydroazepinyl, piperazinyl, piperidinyl, pyridin-2-onyl, pyrrolidinyl, morpholinyl and thiomorpholinyl.

In another embodiment of Formula I and II, heterocyclyl is independently selected from carbazolyl, carbolinyl, cinnolinyl, furanyl, imidazolyl, indolinyl, indolyl, indolazinyl, indazolyl, isobenzofuranyl, isoindolyl, isoquinolyl, isothiazolyl, isoxazolyl, naphthpyridinyl, oxadiazolyl, oxazolyl, oxazoline, isoxazoline, oxetanyl, pyranyl, pyrazinyl, pyrazolyl, pyridazinyl, pyridopyridinyl, pyridazinyl, pyridyl, pyrimidyl, pyrrolyl, quinazolinyl, quinolyl, quinoxalinyl, tetrahydropyranyl, tetrazolyl, tetrazolopyridyl, thiadiazolyl, thiazolyl, thienyl, triazolyl, azetidinyl, 1,4-dioxanyl, hexahydroazepinyl, piperazinyl, piperidinyl, pyridin-2-onyl, pyrrolidinyl, morpholinyl and thiomorpholinyl.

In another embodiment of Formula I and II, heterocycle is selected from: azetidinyl, piperazinyl, piperidinyl, pyrrolidinyl, thiomorpholinyl, and morpholinyl.

As appreciated by those of skill in the art, "halo" or "halogen" as used herein is intended to include chloro (Cl), fluoro (F), bromo (Br) and iodo (I).

In another embodiment, X is NH.
In another embodiment, X is O.
In another embodiment, n is 0, 1, or 2.
In another embodiment, n is 0 or 1.
In another embodiment, n is 1.
In another embodiment, n is 0.
In another embodiment, $R_3$ is methyl, wherein two adjacent methyl groups can join together and form a bridged moiety.

In an embodiment, $R_5$ is phenyl, pyrazolyl, indolyl, isoxazolyl, pyridazinyl, pyridinyl, pyrimidinyl, dihydrobenzodioxinyl, pyrrolopyridinyl, dihydropyridooxazinyl, pyrazolopyridinyl, imidazolpyridinyl, furopyridinyl, thiazolyl, triazolyl, dihydropyrrolopyridinyl, thiophenyl and imidazolyl. optionally substituted with one or more substituents selected from $R_b$.

In an embodiment, when $R_5$ is aryl said aryl is phenyl.
In an embodiment, when $R_b$ is aryl said aryl is phenyl.
In an embodiment, when $R_b$ is heterocyclyl said heterocyclyl is morpholinyl and pyranyl.
In an embodiment, when $R_b$ is alkyl or $R_c$, said alkyl and $R_c$ are optionally substituted with a heterocycle which is pyridinyl.

The pharmaceutically acceptable salts of the instant compounds can be synthesized from the compounds of this invention which contain a basic or acidic moiety by conventional chemical methods. Generally, the salts of the basic compounds are prepared either by ion exchange chromatography or by reacting the free base with stoichiometric amounts or with an excess of the desired salt-forming inorganic or organic acid in a suitable solvent or various combinations of solvents. Similarly, the salts of the acidic compounds are formed by reactions with the appropriate inorganic or organic base.

Thus, pharmaceutically acceptable salts of the compounds of this invention include the conventional non-toxic salts of the compounds of this invention as formed by reacting a basic instant compound with an inorganic or organic acid.

For example, conventional non-toxic salts include those derived from inorganic acids such as hydrochloric, hydrobromic, sulfuric, sulfamic, phosphoric, nitric and the like, as well as salts prepared from organic acids such as acetic, propionic, succinic, glycolic, stearic, lactic, malic, tartaric, citric, ascorbic, pamoic, maleic, hydroxymaleic, phenylacetic, glutamic, benzoic, salicylic, sulfanilic, 2-acetoxybenzoic, fumaric, toluenesulfonic, methanesulfonic, ethane disulfonic, oxalic, isethionic, trifluoroacetic (TFA) and the like.

When the compound of the present invention is acidic, suitable "pharmaceutically acceptable salts" refers to salts prepared form pharmaceutically acceptable non-toxic bases including inorganic bases and organic bases. Salts derived from inorganic bases include aluminum, ammonium, calcium, copper, ferric, ferrous, lithium, magnesium, manganic salts, manganous, potassium, sodium, zinc and the like. Particularly preferred are the ammonium, calcium, magnesium, potassium and sodium salts. Salts derived from pharmaceutically acceptable organic non-toxic bases include salts of primary, secondary and tertiary amines, substituted amines including naturally occurring substituted amines, cyclic amines and basic ion exchange resins, such as arginine, betaine, caffeine, choline, N,N$^1$-dibenzylethylenediamine, diethylamine, 2-diethylaminoethanol, 2-dimethylaminoethanol, ethanolamine, ethylenediamine, N-ethylmorpholine, N-ethylpiperidine, glucamine, glucosamine, histidine, hydrabamine, isopropylamine, lysine, methylglucamine, morpholine, piperazine, piperidine, polyamine resins, procaine, purines, theobromine, triethylamine, trimethylamine, tripropylamine, tromethamine and the like.

The preparation of the pharmaceutically acceptable salts described above and other typical pharmaceutically acceptable salts is more fully described by Berg et al., "Pharmaceutical Salts," *J. Pharm. Sci.*, 1977:66:1-19.

It will also be noted that the compounds of the present invention are potentially internal salts or zwitterions, since under physiological conditions a deprotonated acidic moiety in the compound, such as a carboxyl group, may be anionic, and this electronic charge might then be balanced off internally against the cationic charge of a protonated or alkylated basic moiety, such as a quaternary nitrogen atom.

Utility

According to another embodiment, the present invention provides a method of treating or reducing the severity of a disease in a patient by using a compound of Formulas III as described above, wherein said disease is selected from IRAK4 mediated pathologies, such as rheumatoid arthritis, multiple sclerosis, sepsis, lupus, osteoarthritis, inflammatory bowel disease, Parkinson's disease, cardiac contractile dysfunction, type I diabetes, type II diabetes or familial cold autoinflammatory syndrome, allergic disease, cancer, psoriasis, asthma or graft rejection.

The compounds of the invention find use in a variety of applications. As will be appreciated by those skilled in the art, the kinase activity of IRAK-4 may be modulated in a variety of ways; that is, one can affect the phosphorylation/activation of IRAK-4 either by modulating the initial phosphorylation of the protein or by modulating the autophosphorylation of the other active sites of the protein. Alternatively, the kinase activity of IRAK-4 may be modulated by affecting the binding of a substrate of IRAK-4 phosphorylation.

The compounds of the invention are used to treat or prevent inflammation related diseases. Disease states which can be treated by the methods and compositions provided herein include, but are not limited to, cancer, autoimmune disease, viral disease, fungal disease, neurological/neurodegenerative disorders, arthritis, inflammation, antiproliferative (e.g. ocular retinopathy), neuronal, alopecia, cardiovascular disease, graft rejection, inflammatory bowel disease, proliferation induced after medical procedures, including, but not limited to, surgery, angioplasty, and the like. It is appreciated that in some cases the cells may not be in a hyper- or hypoproliferation state (abnormal state) and still require treatment. Thus, in one embodiment, the invention herein includes application to cells or individuals which are afflicted or may eventually become afflicted with any one of these disorders or states.

The compounds of this invention may be administered to mammals, including humans, either alone or, in combination with pharmaceutically acceptable carriers, excipients or diluents, in a pharmaceutical composition, according to standard pharmaceutical practice. The compounds can be administered orally or parenterally, including the intravenous, intramuscular, intraperitoneal, subcutaneous and topical routes of administration.

The pharmaceutical compositions containing the active ingredient may be in a form suitable for oral use, for example, as tablets, troches, lozenges, aqueous or oily suspensions, dispersible powders or granules, emulsions, hard or soft capsules, or syrups or elixirs. Compositions intended for oral use may be prepared according to any method known to the art for the manufacture of pharmaceutical compositions and such compositions may contain one or more agents selected from the group consisting of sweetening agents, flavoring agents, coloring agents and preserving agents in order to provide pharmaceutically elegant and palatable preparations. Tablets contain the active ingredient in admixture with non-toxic pharmaceutically acceptable excipients which are suitable for the manufacture of tablets. These excipients may be for example, inert diluents, such as calcium carbonate, sodium carbonate, lactose, calcium phosphate or sodium phosphate; granulating and disintegrating agents, for example, microcrystalline cellulose, sodium crosscarmellose, corn starch, or alginic acid; binding agents, for example starch, gelatin, polyvinylpyrrolidone or acacia, and lubricating agents, for example, magnesium stearate, stearic acid or talc. The tablets may be uncoated or they may be coated by known techniques to mask the unpleasant taste of the drug or delay disintegration and absorption in the gastrointestinal tract and thereby provide a sustained action over a longer period. For example, a water soluble taste masking material such as hydroxypropylmethyl-cellulose or hydroxypropylcellulose, or a time delay material such as ethyl cellulose, cellulose acetate buryrate may be employed.

Formulations for oral use may also be presented as hard gelatin capsules wherein the active ingredient is mixed with an inert solid diluent, for example, calcium carbonate, calcium phosphate or kaolin, or as soft gelatin capsules wherein the active ingredient is mixed with water soluble carrier such as polyethyleneglycol or an oil medium, for example peanut oil, liquid paraffin, or olive oil.

Aqueous suspensions contain the active material in admixture with excipients suitable for the manufacture of aqueous suspensions. Such excipients are suspending agents, for example sodium carboxymethylcellulose, methylcellulose, hydroxypropylmethylcellulose, sodium alginate, polyvinyl-pyrrolidone, gum tragacanth and gum acacia; dispersing or wetting agents may be a naturally-occurring phosphatide, for example lecithin, or condensation products of an alkylene oxide with fatty acids, for example polyoxyethylene stearate, or condensation products of ethylene oxide with long chain aliphatic alcohols, for example heptadecaethylene-oxycetanol, or condensation products of ethylene oxide with partial esters derived from fatty acids and a hexitol such as polyoxyethylene sorbitol monooleate, or condensation products of ethylene oxide with partial esters derived from fatty acids and hexitol anhydrides, for example polyethylene sorbitan monooleate. The aqueous suspensions may also contain one or more preservatives, for example ethyl, or n-propyl p-hydroxybenzoate, one or more coloring agents, one or more flavoring agents, and one or more sweetening agents, such as sucrose, saccharin or aspartame.

Oily suspensions may be formulated by suspending the active ingredient in a vegetable oil, for example arachis oil, olive oil, sesame oil or coconut oil, or in mineral oil such as liquid paraffin. The oily suspensions may contain a thickening agent, for example beeswax, hard paraffin or cetyl alcohol. Sweetening agents such as those set forth above, and flavoring agents may be added to provide a palatable oral preparation. These compositions may be preserved by the addition of an anti-oxidant such as butylated hydroxyanisol or alpha-tocopherol.

Dispersible powders and granules suitable for preparation of an aqueous suspension by the addition of water provide the active ingredient in admixture with a dispersing or wetting agent, suspending agent and one or more preservatives. Suitable dispersing or wetting agents and suspending agents are exemplified by those already mentioned above. Additional excipients, for example sweetening, flavoring and coloring agents, may also be present. These compositions may be preserved by the addition of an anti-oxidant such as ascorbic acid.

The pharmaceutical compositions of the invention may also be in the form of an oil-in-water emulsion. The oily phase may be a vegetable oil, for example olive oil or arachis oil, or a mineral oil, for example liquid paraffin or mixtures of these. Suitable emulsifying agents may be naturally-occurring phosphatides, for example soy bean lecithin, and esters or partial esters derived from fatty acids and hexitol anhydrides, for example sorbitan monooleate, and condensation products of the said partial esters with ethylene oxide, for example polyoxyethylene sorbitan monooleate. The emulsions may also contain sweetening, flavouring agents, preservatives and antioxidants.

Syrups and elixirs may be formulated with sweetening agents, for example glycerol, propylene glycol, sorbitol or sucrose. Such formulations may also contain a demulcent, a preservative, flavoring and coloring agents and antioxidant.

The pharmaceutical compositions may be in the form of sterile injectable aqueous solutions. Among the acceptable vehicles and solvents that may be employed are water, Ringer's solution and isotonic sodium chloride solution.

The sterile injectable preparation may also be a sterile injectable oil-in-water microemulsion where the active ingredient is dissolved in the oily phase. For example, the active ingredient may be first dissolved in a mixture of soybean oil and lecithin. The oil solution then introduced into a water and glycerol mixture and processed to form a microemulsion.

The injectable solutions or microemulsions may be introduced into a patient's blood-stream by local bolus injection. Alternatively, it may be advantageous to administer the solution or microemulsion in such a way as to maintain a constant circulating concentration of the instant compound. In order to maintain such a constant concentration, a continuous intravenous delivery device may be utilized. An example of such a device is the Deltec CADD-PLUS™ model 5400 intravenous pump.

The pharmaceutical compositions may be in the form of a sterile injectable aqueous or oleagenous suspension for intramuscular and subcutaneous administration. This suspension may be formulated according to the known art using those suitable dispersing or wetting agents and suspending agents which have been mentioned above. The sterile injectable preparation may also be a sterile injectable solution or suspension in a non-toxic parenterally-acceptable diluent or solvent, for example as a solution in 1,3-butane diol. In addition, sterile, fixed oils are conventionally employed as a solvent or suspending medium. For this purpose any bland fixed oil may be employed including synthetic mono- or diglycerides. In addition, fatty acids such as oleic acid find use in the preparation of injectables.

For topical use, creams, ointments, jellies, solutions or suspensions, etc., containing the compound of Formula I are employed. (For purposes of this application, topical application shall include mouth washes and gargles.)

The compounds for the present invention can be administered in intranasal form via topical use of suitable intranasal vehicles and delivery devices, or via transdermal routes, using those forms of transdermal skin patches well known to those of ordinary skill in the art. To be administered in the form of a transdermal delivery system, the dosage administration will, of course, be continuous rather than intermittent throughout the dosage regimen. Compounds of the present invention may also be delivered as a suppository employing bases such as cocoa butter, glycerinated gelatin, hydrogenated vegetable oils, mixtures of polyethylene glycols of various molecular weights and fatty acid esters of polyethylene glycol.

When a composition according to this invention is administered into a human subject, the daily dosage will normally be determined by the prescribing physician with the dosage generally varying according to the age, weight, and response of the individual patient, as well as the severity of the patient's symptoms.

The dosage regimen utilizing the compounds of the instant invention can be selected in accordance with a variety of factors including type, age, weight, sex; the route of administration; the renal and hepatic function of the patient; and the particular compound or salt thereof employed. An ordinarily skilled physician or veterinarian can readily determine and prescribe the effective amount of the drug required to treat, for example, to prevent, inhibit (fully or partially) or arrest the progress of the disease. For example, compounds of the instant invention can be administered in a total daily dose of up to 10,000 mg.

Compounds of the instant invention can be administered once daily (QD), or divided into multiple daily doses such as twice daily (BID), and three times daily (TID). Compounds of the instant invention can be administered at a total daily dosage of up to 10,000 mg, e.g., 2,000 mg, 3,000 mg, 4,000 mg, 6,000 mg, 8,000 mg or 10,000 mg, which can be administered in one daily dose or can be divided into multiple daily doses as described above.

For example, compounds of the instant invention can be administered in a total daily dose of up to 1,000 mg. Compounds of the instant invention can be administered once daily (QD), or divided into multiple daily doses such as twice daily (BID), and three times daily (TID). Compounds of the instant invention can be administered at a total daily dosage of up to 1,000 mg, e.g., 200 mg, 300 mg, 400 mg, 600 mg, 800 mg or 1,000 mg, which can be administered in one daily dose or can be divided into multiple daily doses as described above.

In addition, the administration can be continuous, i.e., every day, or intermittently. The terms "intermittent" or "intermittently" as used herein means stopping and starting at either regular or irregular intervals. For example, intermittent administration of a compound of the instant invention may be administration one to six days per week or it may mean administration in cycles (e.g. daily administration for two to eight consecutive weeks, then a rest period with no administration for up to one week) or it may mean administration on alternate days.

In addition, the compounds of the instant invention may be administered according to any of the schedules described above, consecutively for a few weeks, followed by a rest period. For example, the compounds of the instant invention may be administered according to any one of the schedules described above from two to eight weeks, followed by a rest period of one week, or twice daily at a dose of 100-500 mg for three to five days a week. In another particular embodiment, the compounds of the instant invention may be administered three times daily for two consecutive weeks, followed by one week of rest.

Any one or more of the specific dosages and dosage schedules of the compounds of the instant invention, may also be applicable to any one or more of the therapeutic agents to be used in the combination treatment (hereinafter referred to as the "second therapeutic agent").

Moreover, the specific dosage and dosage schedule of this second therapeutic agent can further vary, and the optimal dose, dosing schedule and route of administration will be determined based upon the specific second therapeutic agent that is being used.

Of course, the route of administration of the compounds of the instant invention is independent of the route of administration of the second therapeutic agent. In an embodiment, the administration for a compound of the instant invention is oral administration. In another embodiment, the administration for a compound of the instant invention is intravenous administration. Thus, in accordance with these embodiments, a compound of the instant invention is administered orally or intravenously, and the second therapeutic agent can be administered orally, parenterally, intraperitoneally, intravenously, intraarterially, transdermally, sublingually, intramuscularly, rectally, transbuccally, intranasally, liposomally, via inhalation, vaginally, intraocularly, via local delivery by catheter or stent, subcutaneously, intraadiposally, intraarticularly, intrathecally, or in a slow release dosage form.

In addition, a compound of the instant invention and second therapeutic agent may be administered by the same mode of administration, i.e. both agents administered e.g. orally, by IV. However, it is also within the scope of the present invention to administer a compound of the instant invention by one mode of administration, e.g. oral, and to administer the second therapeutic agent by another mode of administration, e.g. IV or any other ones of the administration modes described hereinabove.

The first treatment procedure, administration of a compound of the instant invention, can take place prior to the second treatment procedure, i.e., the second therapeutic agent, after the treatment with the second therapeutic agent, at the same time as the treatment with the second therapeutic agent, or a combination thereof. For example, a total treatment period can be decided for a compound of the instant invention. The second therapeutic agent can be administered prior to onset of treatment with a compound of the instant invention or following treatment with a compound of the instant invention.

The instant compounds are also useful in combination with other therapeutic agents. Combinations of the presently disclosed compounds with therapeutic agents are within the scope of the invention. A person of ordinary skill in the art would be able to discern which combinations of agents would be useful based on the particular characteristics of the drugs and the pathologies involved. The instant compounds are also useful in combination with known therapeutic agents.

The instant compounds are useful in combination with a known anti-inflammatory agent. In one embodiment, the anti-inflammatory agent is a nonsteroidal anti-inflammatory drug (NSAID). In one embodiment, the NSAID is selected from the group consisting of salicylates, indomethacin, flurbiprofen, diclofenac, ketorolac, naproxen, piroxicam, tebufelone, ibuprofen, etodolac, nabumetone, tenidap, alcofenac, antipyrine, aminopyrine, dipyrone, aminopyrone, phenylbutazone, clofezone, oxyphenbutazone, prenazone, apazone, benzydamine, bucolome, cinchophen, clonixin, ditrazol, epirizole, fenoprofen, floctafenin, flufenamic acid, glaphenine, indoprofen, ketoprofen, loxoprofen, meclofenamic acid, mefenamic acid, niflumic acid, phenacetin, salidifamides, sulindac, suprofen, tolmetin, a pharmaceutically acceptable salt thereof, and a mixture thereof.

In another embodiment, the NSAID is a selective COX-2 inhibitor. For purposes of this specification NSAID's which are selective inhibitors of COX-2 are defined as those which possess a specificity for inhibiting COX-2 over COX-1 of at least 100 fold as measured by the ratio of $IC_{50}$ for COX-2 over $IC_{50}$ for COX-1 evaluated by cell or microsomal assays. Such compounds include, but are not limited to those disclosed in U.S. Pat. Nos. 5,474,995, 5,861,419, 6,001,843, 6,020,343, 5,409,944, 5,436,265, 5,536,752, 5,550,142, 5,604,260, 5,698,584, and 5,710,140, WO 94/15932, U.S. Pat. Nos. 5,344,991, 5,134,142, 5,380,738, 5,393,790, 5,466,823, 5,633,272, and 5,932,598, all of which are hereby incorporated by reference.

Compounds that have been described as specific inhibitors of COX-2 and are therefore useful in the present invention include, but are not limited to: parecoxib, CELEBREX® and BEXTRA® or a pharmaceutically acceptable salt thereof.

Those skilled in the art will realize that the term "cancer" to be the name for diseases in which the body's cells become abnormal and divide without control.

Cancers that may be treated by the compounds, compositions and methods of the invention include, but are not limited to: Cardiac: sarcoma (angiosarcoma, fibrosarcoma, rhabdomyosarcoma, liposarcoma), myxoma, rhabdomyoma, fibroma, lipoma and teratoma; Lung: bronchogenic carcinoma (squamous cell, undifferentiated small cell, undifferentiated large cell, adenocarcinoma), alveolar (bronchiolar) carcinoma, bronchial adenoma, sarcoma, lymphoma, chondromatous hamartoma, mesothelioma; Gastrointestinal: esophagus (squamous cell carcinoma, adenocarcinoma, leiomyosarcoma, lymphoma), stomach (carcinoma, lymphoma, leiomyosarcoma), pancreas (ductal adenocarcinoma, insulinoma, glucagonoma, gastrinoma, carcinoid tumors, vipoma), small bowel (adenocarcinoma, lymphoma, carcinoid tumors, Karposi's sarcoma, leiomyoma, hemangioma, lipoma, neurofibroma, fibroma), large bowel (adenocarcinoma, tubular adenoma, villous adenoma, hamartoma, leiomyoma) colorectal; Genitourinary tract: kidney (adenocarcinoma, Wilm's tumor [nephroblastoma], lymphoma, leukemia), bladder and urethra (squamous cell carcinoma, transitional cell carcinoma, adenocarcinoma), prostate (adenocarcinoma, sarcoma), testis (seminoma, teratoma, embryonal carcinoma, teratocarcinoma, choriocarcinoma, sarcoma, interstitial cell carcinoma, fibroma, fibroadenoma, adenomatoid tumors, lipoma); Liver: hepatoma (hepatocellular carcinoma), cholangiocarcinoma, hepatoblastoma, angiosarcoma, hepatocellular adenoma, hemangioma; Bone: osteogenic sarcoma (osteosarcoma), fibrosarcoma, malignant fibrous histiocytoma, chondrosarcoma, Ewing's sarcoma, malignant lymphoma (reticulum cell sarcoma), multiple myeloma, malignant giant cell tumor chordoma, osteochronfroma (osteocartilaginous exostoses), benign chondroma, chondroblastoma, chondromyxofibroma, osteoid osteoma and giant cell tumors; Nervous system: skull (osteoma, hemangioma, granuloma, xanthoma, osteitis deformans), meninges (meningioma, meningiosarcoma, gliomatosis), brain (astrocytoma, medulloblastoma, glioma, ependymoma, germinoma [pinealoma], glioblastoma multiform, oligodendroglioma, schwannoma, retinoblastoma, congenital tumors), spinal cord neurofibroma, meningioma, glioma, sarcoma); Gynecological: uterus (endometrial carcinoma), cervix (cervical carcinoma, pre-tumor cervical dysplasia), ovaries (ovarian carcinoma [serous cystadenocarcinoma, mucinous cystadenocarcinoma, unclassified carcinoma], granulosa-thecal cell tumors, Sertoli-Leydig cell tumors, dysgerminoma, malignant teratoma), vulva (squamous cell carcinoma, intraepithelial carcinoma, adenocarcinoma, fibrosarcoma, melanoma), vagina (clear cell carcinoma, squamous cell carcinoma, botryoid sarcoma (embryonal rhabdomyosarcoma), fallopian tubes (carcinoma), breast; Hematologic: blood (myeloid leukemia [acute and chronic], acute lymphoblastic leukemia, chronic lymphocytic leukemia, myeloproliferative diseases, multiple myeloma, myelodysplastic syndrome), Hodgkin's disease, non-Hodgkin's lymphoma [malignant lymphoma]; Skin: malignant melanoma, basal cell carcinoma, squamous cell carcinoma, Karposi's sarcoma, moles dysplastic nevi, lipoma, angioma, dermatofibroma, keloids, psoriasis; and Adrenal glands: neuroblastoma. Thus, the term "cancerous cell" as provided herein, includes a cell afflicted by any one of the above-identified conditions.

In one embodiment, cancers that may be treated by the compounds, compositions and methods of the invention include, but are not limited to: lung cancer, pancreatic cancer, colon cancer, colorectal cancer, myeloid leukemias, acute myelogenous leukemia, chronic myelogenous leukemia, chronic myelomonocytic leukemia, thyroid cancer, myelodysplastic syndrome, bladder carcinoma, epidermal carcinoma, melanoma, breast cancer, prostate cancer, head and neck cancers, ovarian cancer, brain cancers, cancers of mesenchymal origin, sarcomas, tetracarcinomas, neuroblastomas, kidney carcinomas, hepatomas, non-Hodgkin's lymphoma, multiple myeloma, and anaplastic thyroid carcinoma.

In another embodiment, cancers that may be treated by the compounds, compositions and methods of the invention include, but are not limited to: breast, prostate, colon, colorectal, lung, brain, testicular, stomach, pancrease, skin, small intestine, large intestine, throat, head and neck, oral, bone, liver, bladder, kidney, thyroid and blood.

In another embodiment, cancers that may be treated by the compounds, compositions and methods of the invention include breast, prostate, colon, ovary, endometrium and thyroid.

In another embodiment, cancers that may be treated by the compositions and methods of the invention include acute myeloid leukemia (AML), liposarcoma, colorectal cancer, gastric cancer and melanoma.

In a further embodiment, cancers that may be treated by the compositions and methods of the invention include hematological malignancies, for example acute myeloid leukemia.

In a further embodiment, cancers that may be treated by the compositions and methods of the invention include acute lymphoblastic leukemia (ALL), lymphoma, lung, breast and glioblastoma.

The compounds of the invention are also useful in preparing a medicament that may be useful in treating cancer. In one embodiment, the compounds of the invention are for the potential treatment of cancer.

The compounds of the invention may be useful to the treatment of a variety of cancers, including, but not limited to: carcinoma, including, but not limited to, of the bladder, breast, colon, rectum, endometrium, kidney, liver, lung, head and neck, esophagus, gall bladder, cervix, pancreas, prostrate, larynx, ovaries, stomach, uterus, sarcoma and thyroid cancer; hematopoietic tumors of the lymphoid lineage, including leukemia, acute lymphocytic leukemia, chronic lymphocytic leukemia, acute lymphoblastic leukemia, B-cell lymphoma, T-cell lymphoma, Hodgkins lymphoma, non-Hodgkins lymphoma, hairy cell lymphoma, mantle cell lymphoma, myeloma, and Burkett's lymphoma; hematopoetic tumors of myeloid lineage, including acute and chronic myelogenous leukemias, myelodysplastic syndrome and promyelocytic leukemia; tumors of mesenchymal origin, including fibrosarcoma and rhabdomyosarcoma; tumors of the central and peripheral nervous system, including astrocytoma, neuroblastoma, glioma, and schwannomas; and other tumors, including melanoma, skin (non-melanomal) cancer, mesothelioma (cells), seminoma, teratocarcinoma, osteosarcoma, xenoderoma pigmentosum, keratoctanthoma, thyroid follicular cancer and Kaposi's sarcoma.

The compounds of the invention may be useful for the treatment of activated B-cell-like diffuse large B-cell lymphoma (ABC-DLBCL), chronic lymphocytic leukemia (CLL) and Waldenström's Macroglobulinemia.

The instant compounds are useful in combination with a known anti-cancer agent. Combinations of the presently disclosed compounds with anti-cancer agents are within the scope of the invention. Examples of such anti-cancer agents can be found in *Cancer Principles and Practice of Oncology* by V. T. Devita and S. Hellman (editors), $6^{th}$ edition (Feb. 15, 2001), Lippincott Williams & Wilkins Publishers. A person of ordinary skill in the art would be able to discern which combinations of agents would be useful based on the particular characteristics of the drugs and the cancer involved. Such agents include the following: estrogen receptor modulators, androgen receptor modulators, retinoid receptor modulators, cytotoxic/cytostatic agents, antiproliferative agents, prenylprotein transferase inhibitors, HMG-CoA reductase inhibitors and other angiogenesis inhibitors, HIV protease inhibitors, reverse transcriptase inhibitors, inhibitors of cell proliferation and survival signaling, bisphosphonates, aromatase inhibitors, siRNA therapeutics, γ-secretase inhibitors, agents that interfere with receptor tyrosine kinases (RTKs) and agents that interfere with cell cycle checkpoints.

In one embodiment, the anti-cancer agent is selected from the group consisting of abarelix (Plenaxis Depot®); aldesleukin (Prokine®); Aldesleukin (Proleukin®); Alemtuzumabb (Campath®); alitretinoin (Panretin®); allopurinol (Zyloprim®); altretamine (Hexalen®); amifostine (Ethyol®); anastrozole (Arimidex®); arsenic trioxide (Trisenox®); asparaginase (Elspar®); azacitidine (Vidaza®); bevacuzimab (Avastin®); bexarotene capsules (Targretin®); bexarotene gel (Targretin®); bleomycin (Blenoxane®); bortezomib (Velcade®); busulfan intravenous (Busulfex®); busulfan oral (Myleran®); calusterone (Methosarb®); capecitabine (Xeloda®); carboplatin (Paraplatin®); carmustine (BCNU®, BiCNU®); carmustine (Gliadel®); carmustine with Polifeprosan 20 Implant (Gliadel Wafer®); celecoxib (Celebrex®); cetuximab (Erbitux®); chlorambucil (Leukeran®); cisplatin (Platinol®); cladribine (Leustatin®, 2-CdA®); clofarabine (Clolar®); cyclophosphamide (Cytoxan®, Neosar®); cyclophosphamide (Cytoxan Injection®); cyclophosphamide (Cytoxan Tablet®); cytarabine (Cytosar-U®); cytarabine liposomal (DepoCyt®); dacarbazine (DTIC-Dome®); dactinomycin, actinomycin D (Cosmegen®); Darbepoetin alfa (Aranesp®); daunorubicin liposomal (DanuoXome®); daunorubicin, daunomycin (Daunorubicin®); daunorubicin, daunomycin (Cerubidine®); Denileukin diftitox (Ontak®); dexrazoxane (Zinecard®); docetaxel (Taxotere®); doxorubicin (Adriamycin PFS®); doxorubicin (Adriamycin®, Rubex®); doxorubicin (Adriamycin PFS Injection®); doxorubicin liposomal (Doxil®); dromostanolone propionate (Dromostanolone®); dromostanolone propionate (Masterone Injection®); Elliott's B Solution (Elliott's B Solution®); epirubicin (Ellence®); Epoetin alfa (Epogen®); erlotinib (Tarceva®); estramustine (Emcyt®); etoposide phosphate (Etopophos®); etoposide, VP-16 (Vepesid®); exemestane (Aromasin®); Filgrastim (Neupogen®); floxuridine (intraarterial) (FUDR®); fludarabine (Fludara®); fluorouracil, 5-FU (Adrucil®); fulvestrant (Faslodex®); gefitinib (Iressa®); gemcitabine (Gemzar®); gemtuzumab ozogamicin (Mylotarg®); goserelin acetate (Zoladex Implant®); goserelin acetate (Zoladex®); histrelin acetate (Histrelin Implant®); hydroxyurea (Hydrea®); Ibritumomab Tiuxetan (Zevalin®); idarubicin (Idamycin®); ifosfamide (IFEX®); imatinib mesylate (Gleevec®); interferon alfa 2a (Roferon A®); Interferon alfa-2b (Intron A®); irinotecan (Camptosar®); lenalidomide (Revlimid®); letrozole (Femara®); leucovorin (Wellcovorin®, Leucovorin®); Leuprolide Acetate (Eligard®); levamisole (Ergamisol®); lomustine, CCNU (CeeBU®); mechlorethamine, nitrogen mustard (Mustargen®); megestrol acetate (Megace®); melphalan, L-PAM (Alkeran®); mercaptopurine, 6-MP (Purinethol®); mesna (Mesnex®); mesna (Mesnex Tabs®); methotrexate (Methotrexate®); methoxsalen (Uvadex®); mitomycin C (Mutamycin®); mitotane (Lysodren®); mitoxantrone (Novantrone®); nandrolone phenpropionate (Durabolin-50®); nelarabine (Arranon®); Nofetumomab (Verluma®); Oprelvekin (Neumega®); oxaliplatin (Eloxatin®); paclitaxel (Paxene®); paclitaxel (Taxol®); paclitaxel protein-bound particles (Abraxane®); palifermin (Kepivance®); pamidronate (Aredia®); pegademase (Adagen (Pegademase Bovine)®); pegaspargase (Oncaspar®); Pegfilgrastim (Neulasta®); pemetrexed disodium (Alimta®); pentostatin (Nipent®); pipobroman (Vercyte®); plicamycin, mithramycin (Mithracin®); porfimer sodium (Photofrin®); procarbazine (Matulane®); quinacrine (Atabrine®); Rasburicase (Elitek®); Rituximab (Rituxan®); sargramostim (Leukine®); Sargramostim (Prokine®); sorafenib (Nexavar®); streptozocin (Zanosar®); sunitinib maleate (Sutent®); talc (Sclerosol®); tamoxifen (Nolvadex®); temozolomide (Temodar®); teniposide, VM-26 (Vumon®); testolactone (Teslac®); thioguanine, 6-TG (Thioguanine®); thiotepa (Thioplex®); topotecan (Hycamtin®); toremifene (Fareston®); Tositumomab (Bexxar®); Tositumomab/I-131 tositumomab (Bexxar®); Trastuzumab (Herceptin®); tretinoin, ATRA (Vesanoid®); Uracil Mustard (Uracil Mustard Capsules®); valrubicin (Valstar®); vinblastine (Velban®); vincristine (Oncovin®); vinorelbine (Navelbine®); zoledronate (Zometa®) and vorinostat (Zolinza®); a pharmaceutically acceptable salt thereof, and a mixture thereof.

The term "administration" and variants thereof (e.g., "administering" a compound) in reference to a compound of the invention means introducing the compound or a prodrug of the compound into the system of the animal in need of treatment. When a compound of the invention or prodrug thereof is provided in combination with one or more other active agents (e.g., a cytotoxic agent, etc.), "administration" and its variants are each understood to include concurrent and sequential introduction of the compound or prodrug thereof and other agents.

As used herein, the term "composition" is intended to encompass a product comprising the specified ingredients in the specified amounts, as well as any product which results, directly or indirectly, from combination of the specified ingredients in the specified amounts.

The term "therapeutically effective amount" as used herein means that amount of active compound or pharmaceutical agent that elicits the biological or medicinal response in a tissue, system, animal or human that is being sought by a researcher, veterinarian, medical doctor or other clinician.

The compounds of the instant invention are useful for the treatment and/or reducing the severity of rheumatoid arthritis.

The compounds of the instant invention are useful for the treatment and/or reducing the severity of inflammatory bowel disease.

The compounds of the instant invention are useful for the treatment and/or reducing the severity of cancer.

The compounds of the instant invention are useful for the treatment and/or reducing the severity of lupus.

The compounds of the instant invention are useful for the treatment of rheumatoid arthritis.

The compounds of the instant invention are useful for the treatment of inflammatory bowel disease.

The compounds of the instant invention are useful for the treatment of lupus.

The compounds of the instant invention are useful for the treatment of cancer.

Further included within the scope of the invention is a method for treating an inflammatory disease which comprises administering to a mammal in need thereof a therapeutically effective amount of a compound of the instant invention.

Further included within the scope of the invention is a method for treating an inflammatory disease which comprises administering to a mammal in need thereof a therapeutically effective amount of a compound of the instant invention wherein the inflammatory disease is selected from rheumatoid arthritis, inflammatory bowel disease and cancer.

Further included within the scope of the invention is a method of treating an inflammatory disease which comprises administering a therapeutically effective amount of a compound of the instant invention in combination with a second therapeutic agent.

Further included within the scope of the invention is a method of treating an inflammatory disease which comprises administering a therapeutically effective amount of a compound of the instant invention in combination with a second therapeutic agent, wherein the second therapeutic agent is selected from an anti-cancer agent and an anti-inflammatory agent.

Abbreviations used in the description of the chemistry and in the Examples that follow are:
2nd Gen. Precatalyst cataCXium® chloro[(di(1-adamantyl)-N-butylphosphine)-2-(2-aminobiphenyl)]palladium(II)
2nd Gen. Precatalyst X-Phos Chloro(2-dicyclohexylphosphino-2',4',6'-triisopropyl-1,1'-biphenyl)[2-(2'-amino-1,1'-biphenyl)]palladium(II)
3rd Gen X-Phos Precatalys (2-Dicyclohexylphosphino-2',4',6'-triisopropyl-1,1'-biphenyl)[2-(2'-amino-1,1'-biphenyl)]palladium(II) methanesulfonate
Ac acetyl
ACN or MeCN acetonitrile
AcOH or HOAc acetic acid
APCI atmospheric-pressure chemical ionization
aq aqueous
Bn benzyl
Boc or BOC tert-butoxycarbonyl
Brettphos 2-(dicyclohexylphosphino)3,6-dimethoxy-2',4',6'-triisopropyl-1,1'-biphenyl
Bu butyl
Bz benzoyl
calc'd calculated
cBu cyclobutyl
Cbz benyzloxycarbonyl
$CDCl_3$ chloroform-d
$CHCl_3$ chloroform
cHep cycloheptyl
cHex cyclohexyl
cPen cyclopentyl
cPr cyclopropyl
DAST (diethylamino)sulfur trifluoride
Dba dibenzylideneacetone
DBU 1,8-diazabicycloundec-7-ene
DCE 1,2-dichloroethane
DCM dichloromethane
DIBAL or Dibal-H diisobutylaluminum hydride
DIEA or Hünig's base N,N-diisopropylethylamine
DMA 1,2-dimethylacetamide
DMAP 4-dimethylaminopyridine
DMEA dimethylethylamine
DMSO dimethylsulfoxide
DMF dimethylformamide
DMP Dess-Martin periodinane (1,1,1-triacetoxy)-1,1-dihydro-1,2-benziodoxol-3(1H)-one
DMSO dimethyl sulfoxide
dppf 1,1'-bis(diphenylphosphino)ferrocene
DTT dithiothreitol
EDC 1-ethyl-3-(3-dimethylaminopropyl)carbodiimide
EDTA ethylenediamine tetraacetic acid
ESI electrospray ionization
Et ethyl
EtOH ethanol
EtOAc ethyl acetate
g grams
GST glutathione S-transferase
h hour
HATU N,N,N',N'-tetramethyl-O-(7-azabenzotriazol-1-yl)uronium hexafluorophosphate
HCl hydrochloric acid
HMDS 1,1,1,3,3,3-hexamethyldisilazane
HOBt 1-hydroxybenzotriazole
HPLC high-performance liquid chromatography
IPA or iPrOH isopropanol
iPr isopropyl
LC liquid chromatography
LCMS liquid chromatography mass spectrometry
LDA lithium diisopropylamide
M molar
mCPBA m-choroperoxybenzoic acid
Me methyl
MeOH methanol
mg milligrams
min minute
µL microliters
mL milliliters
mmol millimoles
MS mass spectrometry
Ms methanesulfonyl (mesyl)
MTBE methyl tert-butyl ether
NBS N-bromosuccinimide
NMR nuclear magnetic resonance spectroscopy
OAc acetate
obsv'd observed
$Pd(PPh_3)_4$ palladium(0) tetrakis-triphenylphosphine
$Pd(dppf)Cl_2$ 1,1'-bis(diphenylphosphino)ferrocene]dichloro palladium(II)
Ph phenyl
$(PinB)_2$ 4,4,4',4',5,5,5',5'-octamethyl-2,2'-bi(1,3,2-dioxaborolane)
$POCl_3$ phosphorous oxychloride
Pr propyl
PS polystyrene
rac racemic mixture
RT or rt room temperature (ambient, about 25° C.)
sat saturated
SFC supercritical fluid chromatography
Si-DPP-Pd SiliaCat®DPP-Pd
S-phos 2-dicyclohexylphosphino-2',6'-dimethoxybiphenyl
T3P Propylphosphonic anhydride
TBAF tert-butyl ammonium fluoride
TBDPS tert-butyl diphenyl silyl
TBS or TBDMS tert-butyldimethyl silyl
TBSCl tert-butyldimethylsilyl chloride
tBu tert-butyl
tBu X-phos 2-di-tert-butylphosphino-2',4',6'-triisopropylbiphenyl
TEA triethylamine ($Et_3N$)
TFA trifluoroacetic acid
TFAA trifluoroacetic anhydride
THF tetrahydrofuran
TLC thin layer chromatography
TMS trimethylsilyl
Tris tris(hydroxymethyl)aminomethane
Ts toluenesulfonyl (tolyl)
TSA p-toluenesulfonic acid
X-phos 2-dicyclohexylphosphino-2',4',6'-triisopropylbiphenyl
Xantphos 4,5-bis(diphenylphosphino)-9,9-dimethylxanthene General Synopsis of Reaction Schemes The following General Reaction Schemes, Schemes 1 to 5, provide useful details for preparing the instant compounds. The requisite intermediates are in some cases commercially available or can be prepared according to literature procedures. The illustrative General Reaction Schemes below are not limited by the compounds listed or by any particular substituents employed for illustrative purposes. Substituent labeling (i.e. R groups) as shown in the Reaction Schemes do not necessarily correlate to that used in the claims and often, for clarity, a single substituent is shown attached to the compound where multiple substituents are allowed under the definitions of Formula I hereinabove.

Scheme 1
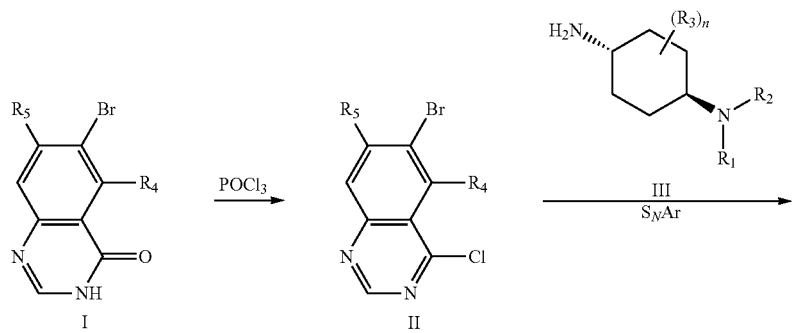
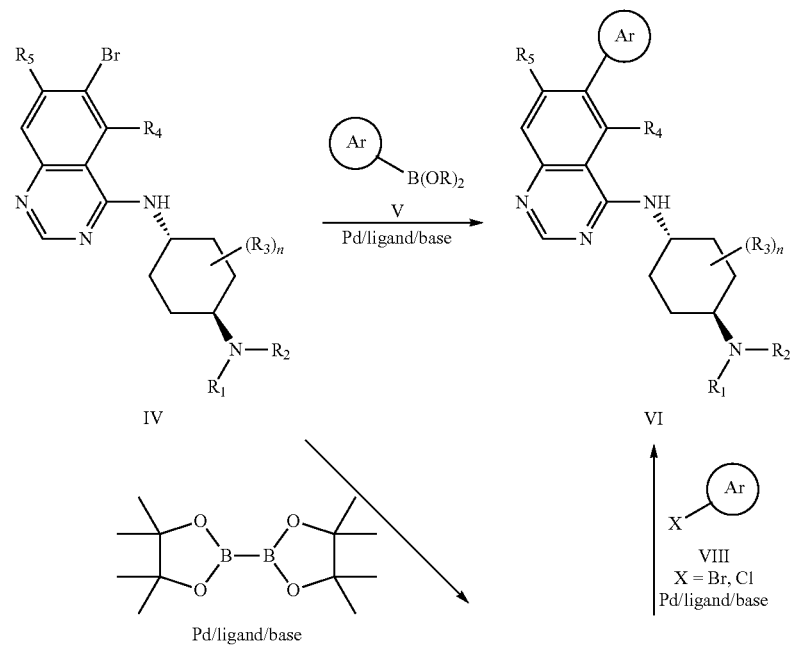
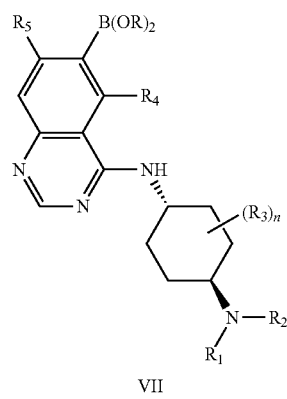

Compounds of formula VI are prepared by the palladium-mediated cross coupling of 6-bromo-4-aminoquinazolines (IV) to aryl boronic acids or boronate esters (V). Additionally, compounds of formula VI are obtained by the palladium-mediated cross coupling of 6-boronate-4-aminoquinazolines (VII) to aryl halides (VIII). 6-boronate-4-aminoquinazolines (VII) are prepared by borylation of 6-bromo-4-aminoquinazolines (IV). 6-bromo-4-aminoquinazolines (IV) are prepared by the reaction of 4-chloroquinazolines (II) with the desired amines (III) via $S_NAr$ conditions. Substituted 4-chloroquinazolines (II) are prepared from substituted 4-quinazolinones (I) by chlorination with $POCl_3$.

Compounds of formula X are prepared from substituted quinazolines (IX) by acidic deprotection of the PMB protecting group. Substituted quinazolines (IX) are prepared according to Scheme 1.

Scheme 2

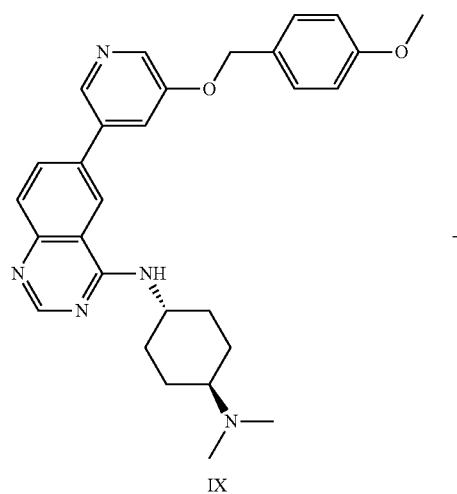

IX

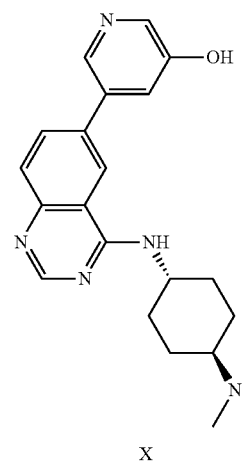

X

Scheme 3

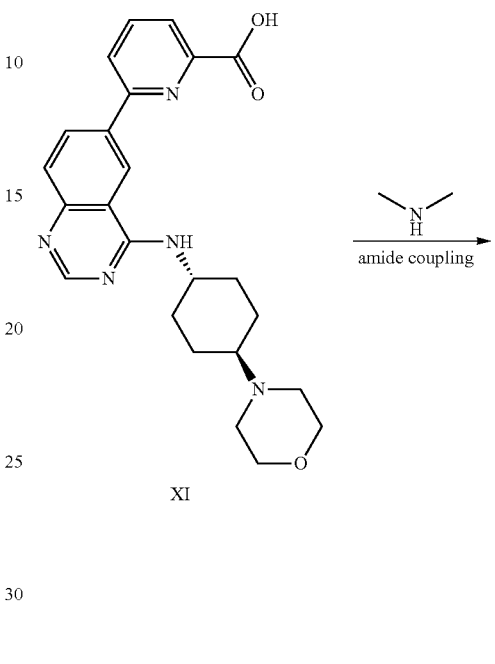

XI

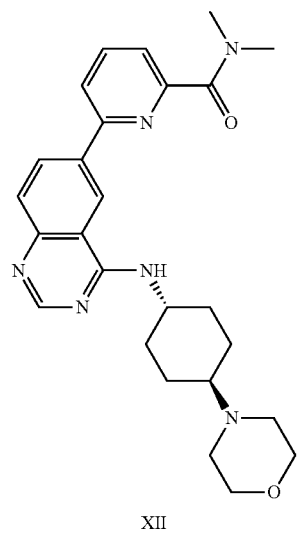

XII

Compounds of formula XII are prepared from substituted quinazolines (XI) by amidation conditions. Substituted quinazolines (XI) are prepared according to Scheme 1.

Scheme 4
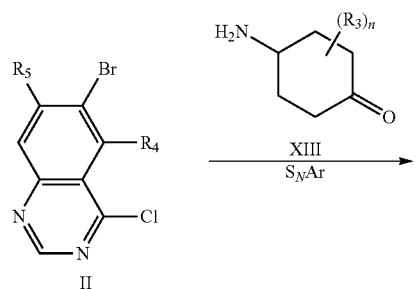
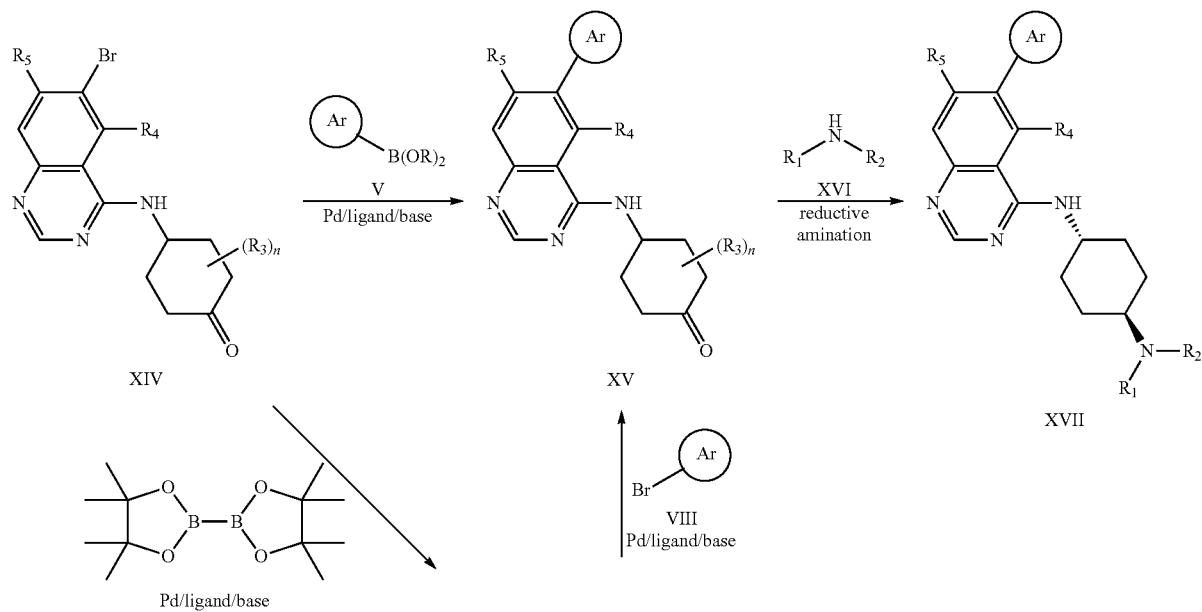
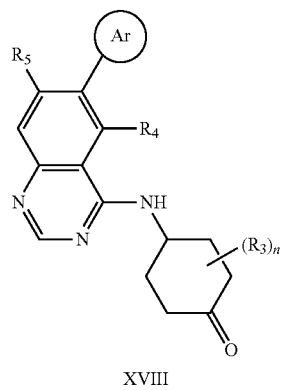

Compounds of formula XVII are prepared by the reductive amination of cyclohexanones (XV) with substituted amines (XVI). Cyclohexanones (XV) are prepared by the palladium-mediated cross coupling of 6-bromo-4-aminoquinazolines (XIV) to aryl boronic acids or boronate esters (V). Alternately, cyclohexanones (XV) are obtained by the palladium-mediated cross coupling of 6-boronate-4-aminoquinazolines (XVIII) to aryl halides (VIII). 6-boronate-4-aminoquinazolines (XVIII) are prepared by borylation of 6-bromo-4-aminoquinazolines (XIV). 6-bromo-4-aminoquinazolines (XIV) are obtained by the reaction of 4-chloroquinazolines (II) with the desired substituted 4-aminocyclohexanones (XIII) via $S_NAr$ conditions. Substituted 4-chloroquinazolines (II) are prepared according to Scheme 1.

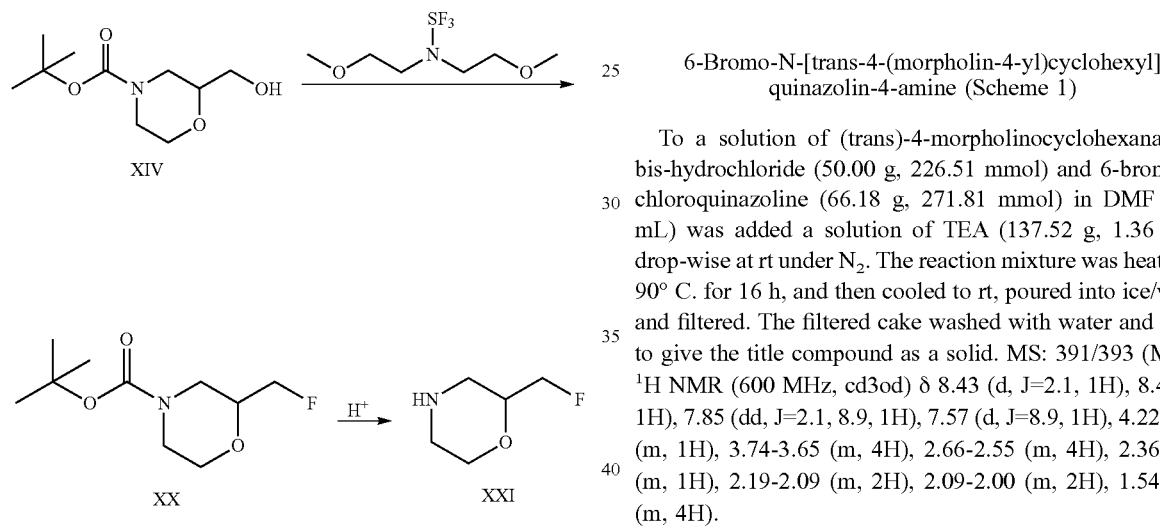

Scheme 5

Compounds of formula XXI are prepared by the acidic deprotection of fluoromethylmorpholines (XX). Fluoromethylmorpholines (XX) are prepared by the fluorination of hydroxymethylmorpholines (XIV) with bis(2-methoxyethyl)aminosulfur trifluoride.

Intermediate 1-1

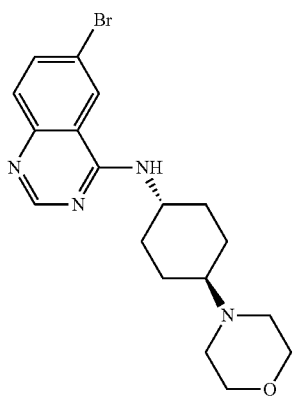 [SMILES: Brc1ccc2ncnc(N[C@H]3CC[C@H](N4CCOCC4)CC3)c2c1]

6-Bromo-N-[trans-4-(morpholin-4-yl)cyclohexyl]quinazolin-4-amine (Scheme 1)

To a solution of (trans)-4-morpholinocyclohexanamine bis-hydrochloride (50.00 g, 226.51 mmol) and 6-bromo-4-chloroquinazoline (66.18 g, 271.81 mmol) in DMF (600 mL) was added a solution of TEA (137.52 g, 1.36 mol) drop-wise at rt under $N_2$. The reaction mixture was heated to 90° C. for 16 h, and then cooled to rt, poured into ice/water and filtered. The filtered cake washed with water and dried to give the title compound as a solid. MS: 391/393 (M+1). $^1$H NMR (600 MHz, cd3od) δ 8.43 (d, J=2.1, 1H), 8.41 (s, 1H), 7.85 (dd, J=2.1, 8.9, 1H), 7.57 (d, J=8.9, 1H), 4.22-4.12 (m, 1H), 3.74-3.65 (m, 4H), 2.66-2.55 (m, 4H), 2.36-2.25 (m, 1H), 2.19-2.09 (m, 2H), 2.09-2.00 (m, 2H), 1.54-1.38 (m, 4H).

The following examples in Table 1 were prepared in an analogous manner of those described in Intermediate 1-1 and general scheme 1.

TABLE 1

| Intermediate Number | Structure | Chemical Name | MS (M + 1) |
|---|---|---|---|
| 1-2 | 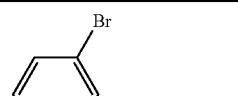 | trans-N'-(6-bromoquinazolin-4-yl)-N,N-dimethylcyclohexane-1,4-diamine | Calc'd 349.0, found 349/351 |

TABLE 1-continued

| Intermediate Number | Structure | Chemical Name | MS (M + 1) |
|---|---|---|---|
| 1-3 | 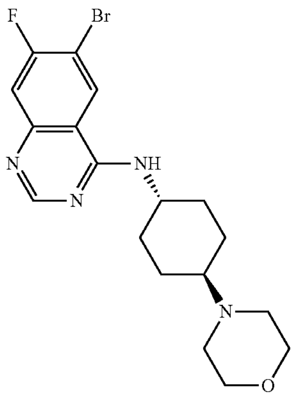 [SMILES: Fc1cc2ncnc(N[C@H]3CC[C@H](N4CCOCC4)CC3)c2cc1Br] | 6-bromo-7-fluoro-N-[trans-4-(morpholin-4-yl)cyclohexyl]quinazolin-4-amine | Calc'd 409.0, found 409/411 |
| 1-4 | 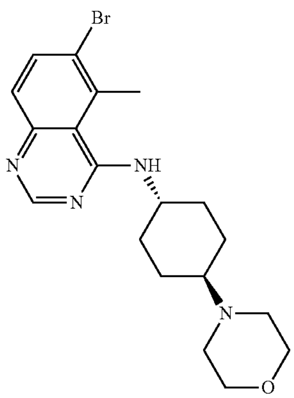 [SMILES: Cc1c(Br)ccc2ncnc(N[C@H]3CC[C@H](N4CCOCC4)CC3)c12] | 7-bromo-8-methyl-N-[trans-4-(morpholin-4-yl)cyclohexyl]naphthalen-1-amine | Calc'd 405.0, found 405/407 |

Intermediate 2-1

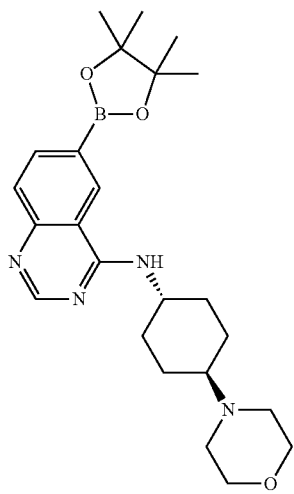 [SMILES: CC1(C)OB(c2ccc3ncnc(N[C@H]4CC[C@H](N5CCOCC5)CC4)c3c2)OC1(C)C]

N-((Trans)-4-morpholinocyclohexyl)-6-(4,4,5,5-tetramethyl-1,3,2-dioxaborolan-2-yl)quinazolin-4-amine (Scheme 1)

To a solution of 6-bromo-N-((trans)-4-morpholinocyclohexyl)quinazolin-4-amine (65.0 g, 0.166 mol) in dioxane (400 mL) at 23° C. was added Pd(dppf)Cl$_2$ (13.6 g, 0.017 mol) and (PinB)$_2$ (51 g, 0.20 mol), followed by the addition of 2,6-dimethylpyridine (20 g, 0.18 mol) and potassium acetate (32.6 g, 0.33 mol). The resulting mixture was heated to 90° C. and stirred for 16 h. The mixture was cooled to 23° C. and filtered. The filtrate was concentrated under reduced pressure, and the residue was dissolved in dichloromethane. The solution was washed sequentially with saturated aqueous NaHCO$_3$ and saturated aqueous NaCl. The organic layer was concentrated and decolorized by activated carbon to give a product. The crude solid was triturated with MTBE to afford the title compound as a solid. MS: 339 (M+1). $^1$H NMR (500 MHz, acetone-d6): δ 8.52 (s, 1H), 8.46 (s, 1H), 8.03 (d, J=8.5 Hz, 1H), 7.68 (d, J=8.5 Hz, 2H), 4.35-4.28 (m, 1H), 3.64-3.59 (m, 4H), 2.83-2.81 (m, 1H), 2.58-2.54 (m, 4H, 2.32-2.25 (m, 1H), 2.21-2.26 (m, 2H), 2.00-1.95 (m, 2H), 1.58-1.40 (m, 4H), 1.38 (s, 12H).

Intermediate 3-1

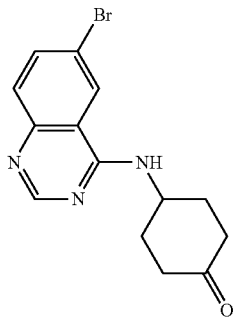 [SMILES: O=C1CCC(Nc2ncnc3ccc(Br)cc23)CC1]

4-[(6-Bromoquinazolin-4-yl)amino]cyclohexanone (Scheme 4)

A 200 mL round bottom flask was charged with 6-bromo-4-chloroquinazoline (5.00 g, 20.5 mmol), 4-aminocyclohexanone hydrochloride (3.38 g, 22.6 mmol), DMA (50 mL) and DIEA (17.9 mL, 103 mmol). The contents of the flask were allowed to stir at room temperature for 24 hours. The reaction mixture was concentrated under reduced pressure. The resulting residue was triturated in EtOH affording a precipitate. The solid was collected by vacuum filtration on a glass frit and dried under reduced pressure to afford the title compound without further purification. MS: 320/322 (M+1). $^1$H NMR (600 MHz, DMSO-$d_6$) δ 8.66 (1H, s), 8.57 (1H, s), 8.41 (1H, br s), 7.91 (1H, d, J=8.85 Hz), 7.62 (1H, d, J=8.83 Hz), 4.71-4.63 (1H, m), 2.57-2.52 (2H, m), 2.30-2.28 (2H, m), 2.22-2.16 (2H, m), 1.86-1.84 (2H, m).

Intermediate 4-1

4-[(6-(5-(Methylamino)pyridin-3-yl)quinazolin-4-yl)amino]cyclohexanone (Scheme 4)

A 20 mL microwave vial was charged with 4-((6-bromoquinazolin-4-yl)amino)cyclohexanone (200 mg, 0.625 mmol), 5-(methylamino)pyridine-3-boronic acid pinacol ester (219 mg, 0.937 mmol), 3rd Gen X-Phos Precatalyst (106 mg, 0.125 mmol) and DMA (6 ml). An aqueous solution of 2M potassium phosphate tribasic (0.937 mL, 1.87 mmol) was added. The vial was flushed with argon, capped and the contents heated to 60° C. for 3 hours. The reaction mixture was diluted with DCM (10 mL), filtered through celite and concentrated. The resulting residue was diluted with chloroform/isopropanol—3:1 (20 mL), washed with aqueous ammonium chloride (saturated, 2×10 mL), dried (MgSO$_4$), filtered and the filtrate was concentrated under reduced pressure. The resulting residue was purified by column chromatography on silica gel ISCO; 12 g pre-packed, (0-25% ethyl acetate/methanol) to afford the title compound. MS: 348 (M+1). $^1$H NMR (600 MHz, CD$_3$OD): δ 8.495 (s, 1H); 8.488 (s, 1H); 8.14 (d, J=1.9 Hz, 1H); 8.07 (dd, J=8.7, 2.0 Hz, 1H); 7.92 (d, J=2.6 Hz, 1H); 7.80 (d, J=8.6 Hz, 1H); 7.29 (t, J=2.2 Hz, 1H); 2.88 (s, 3H); 2.69-2.63 (m, 2H); 2.44-2.38 (m, 4H); 1.97-1.90 (m, 2H).

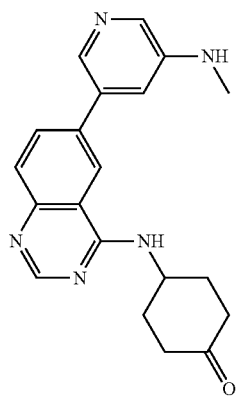 [SMILES: CNc1cncc(-c2ccc3ncnc(NC4CCC(=O)CC4)c3c2)c1]

The following examples in Table 2 were prepared in an analogous manner of those described in Intermediate 4-1 and general scheme 4.

TABLE 2

| Intermediate Number | Structure | Chemical Name | MS (M + 1) |
|---|---|---|---|
| 4-2 | (structure shown) | 4-{[6-(5-hydroxypyridin-3-yl)quinazolin-4-yl]amino}cyclohexanone | Calc'd 335.0, found 335 |

TABLE 2-continued

| Intermediate Number | Structure | Chemical Name | MS (M + 1) |
|---|---|---|---|
| 4-3 | 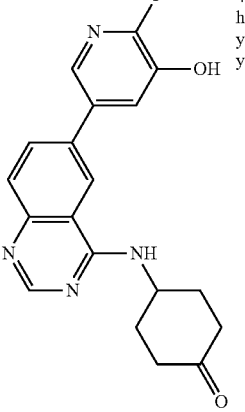 | 4-{[6-(6-fluoro-5-hydroxypyridin-3-yl)quinazolin-4-yl]amino}cyclohexanone | Calc'd 353.0, found 353 |
| 4-4 | 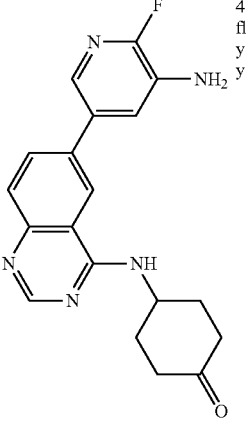 | 4-{[6-(5-amino-6-fluoropyridin-3-yl)quinazolin-4-yl]amino}cyclohexanone | Calc'd 352.0, found 352 |

Intermediate 5-1

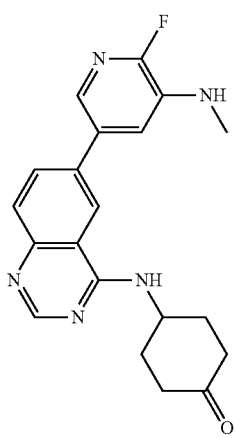 [SMILES: Nc1cc(-c2ccc3ncnc(NC4CCC(=O)CC4)c3c2)cnc1F]

4-((6-(6-Fluoro-5-(methylamino)pyridin-3-yl)quinazolin-4-yl)amino)cyclohexanone (Scheme 4)

Step 1: 4-((6-(4,4,5,5-Tetramethyl-1,3,2-dioxaborolan-2-yl)quinazolin-4-yl)amino)cyclohexanone (Scheme 4)

A 20 mL microwave vial was charged with 4-((6-bromoquinazolin-4-yl)amino)cyclohexanone (0.480 g, 1.50 mmol), bis(pinacolato)diboron (0.419 g, 1.65 mmol), potassium acetate (0.442 g, 4.50 mmol), 1,1'-bis(diphenylphosphino)ferrocenepalladium(II)dichloride dichloromethane complex (0.122 g, 0.150 mmol) and dioxane (10 mL). The vial was flushed with argon, capped and the contents heated to 80° C. for 2 hours. The reaction mixture was diluted with DCM (5 mL), filtered and the filtrate was concentrated under reduced pressure to afford crude 4-((6-(4,4,5,5-tetramethyl-1,3,2-dioxaborolan-2-yl)quinazolin-4-yl)amino)cyclohexanone which was taken forward without further purification. MS: 368 (M+1).

Step 2: 4-((6-(6-Fluoro-5-(methylamino)pyridin-3-yl)quinazolin-4-yl)amino)cyclohexanone A 20 mL microwave vial was charged with 4-((6-(4,4,5,5-tetramethyl-1,3,2-dioxaborolan-2-yl)quinazolin-4-yl)amino)cyclohexanone (551 mg, 1.50 mmol), 5-bromo-2- fluoro-N-methylpyridin-3-amine (308 mg, 1.5 mmol), 3rd Gen X-Phos Precatalyst (254 mg, 0.300 mmol) and DMA (10 ml). An aqueous solution of 2M potassium phosphate tribasic (2.25 ml, 4.50 mmol) was added. The vial was flushed with argon, capped and the contents heated to 60° C. for 3 hours. The reaction mixture was filtered through celite, washing through with DCM and the filtrate was concentrated. The resulting residue was diluted with chloroform/isopropanol—3:1 (20 mL), washed with aqueous ammonium chloride (saturated, 2×10 mL), dried ($MgSO_4$), filtered and the solvent was evaporated under reduced pressure. The resulting residue was purified by column chromatography on silica gel ISCO; 40 g prepacked, (0-15% ethyl acetate/methanol) to afford the title compound. MS: 366 (M+1). $^1$H NMR (600 MHz, DMSO-$d_6$): δ 8.57 (d, J=2.0 Hz, 1H); 8.48 (s, 1H); 8.08-8.05 (m, 2H); 7.74-7.72 (m, 2H); 7.29-7.27 (m, 1H); 6.04 (d, J=5.6 Hz, 1H); 4.70-4.67 (m, 1H); 2.81 (d, J=4.9 Hz, 3H); 2.61-2.55 (m, 2H); 2.29 (d, J=15.0 Hz, 2H); 2.27-2.22 (m, 2H); 1.88-1.82 (m, 2H).

Intermediates 6-1 and 6-2

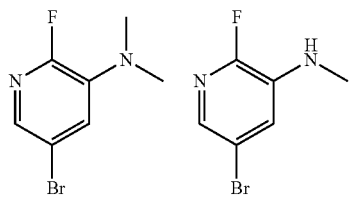

5-Bromo-2-fluoro-N,N-dimethylpyridin-3-amine and 5-bromo-2-fluoro-N-methylpyridin-3-amine A 50 mL round bottom flask containing 5-bromo-2-fluoropyridin-3-amine (500 mg, 2.62 mmol) in DMF (5 mL) was cooled to 0° C. using an ice-water bath. Sodium hydride (60% dispersion in mineral oil) (105 mg, 2.62 mmol) was added and the reaction mixture was stirred for 10 minutes. Iodomethane (0.164 mL, 2.62 mmol) was added and the reaction mixture warmed to ambient temperature over 16 hours. The reaction mixture was concentrated, the resulting residue diluted with dichloromethane (5 mL), washed with aqueous sodium hydrogen carbonate (saturated, 2×5 mL), dried ($MgSO_4$), filtered and the solvent was evaporated under reduced pressure. The resulting residue was purified by column chromatography on silica gel ISCO; 12 g prepacked, (0-10% hexanes/ethyl acetate) to afford 5-bromo-2-fluoro-N,N-dimethylpyridin-3-amine. MS: 219 (M+1). 1H NMR (600 MHz, DMSO-$d_6$): δ 7.65 (t, J=2.2 Hz, 1H); 7.43 (dd, J=9.5, 2.2 Hz, 1H); 2.82 (d, J=1.3 Hz, 6H) and 5-bromo-2-fluoro-N-methylpyridin-3-amine. MS: 205 (M+1). $^1$H NMR (600 MHz, DMSO-$d_6$): δ 7.33 (t, J=2.2 Hz, 1H); 7.12 (dd, J=9.5, 2.2 Hz, 1H); 6.24 (s, 1H); 2.68 (d, J=4.9 Hz, 3H).

Intermediate 7-1

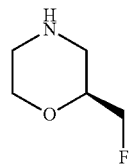

(S)-2-(Fluoromethyl)morpholine, HCl (Scheme 5)

Step 1: (S)-Tert-butyl 2-(fluoromethyl)morpholine-4-carboxylate

A 100 mL round bottom flask was charged with (S)-tert-butyl 2-(hydroxymethyl)morpholine-4-carboxylate (1.00 g, 4.60 mmol) and DCM (20.0 mL). Bis(2-methoxyethyl)aminosulfur trifluoride (2.55 ml, 13.8 mmol) was added and the reaction was allowed to stir at room temperature for 18 hours. The reaction was diluted with water and extracted with DCM. The organic layer was dried over MgSO4, filtered and the filtrate was concentrated under reduced pressure affording crude (S)-tert-butyl 2-(fluoromethyl)morpholine-4-carboxylate which was taken forward without further purification. MS: 164 (M+1-56).

Step 2: (S)-2-(Fluoromethyl)morpholine, HCl

A 25 mL round bottom flask was charged with (S)-tert-butyl 2-(fluoromethyl)morpholine-4-carboxylate (0.958 g, 4.37 mmol) and 4M hydrochloric acid in dioxane (5.50 mL, 21.9 mmol). The reaction was stirred at room temperature for 1 hour then concentrated under reduced pressure to afford the title compound which was taken on without purification. MS: 120 (M+1).

The following example in Table 3 was prepared in an analogous manner of that described in Intermediate 7-1 and general scheme 5.

TABLE 3

| Intermediate Number | Structure | Chemical Name | MS (M + 1) |
|---|---|---|---|
| 7-2 | 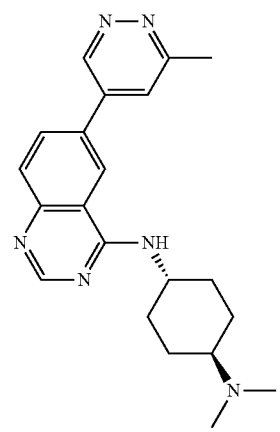 [SMILES: Cc1cc(-c2ccc3ncnc(N[C@H]4CC[C@H](N(C)C)CC4)c3c2)cnn1] | (R)-2-(fluoromethyl)morpholine, HCl | Calc'd 120.0, found 120 |

EXAMPLE 1-1

Trans-N,N-dimethyl-N'-[6-(6-methylpyridazin-4-yl)quinazolin-4-yl]cyclohexane-1,4-diamine (Scheme 1)

Aqueous potassium phosphate, tribasic (2.3 M, 100 μL, 0.229 mmol) was added to a vial containing a solution of 3-methyl-5-(4,4,5,5-tetramethyl-1,3,2-dioxaborolan-2-yl)pyridazine (12.6 mg, 0.057 mmol), chloro(2-dicyclohexylphosphino-2',4',6'-triisopropyl-1,1'-biphenyl)[2-(2'-amino-1,1'-biphenyl)]palladium(II) (6.76 mg, 0.008 mmol) and trans-N'-(6-bromoquinazolin-4-yl)-N,N-dimethylcyclohexane-1,4-diamine (20.0 mg, 0.057 mmol) in dimethylacetamide (500 μL) under an argon atmosphere. The reaction mixture was stirred for 16 h at 60° C. The reaction was cooled to rt, filtered and purified by mass triggered reverse phase HPLC (ACN/water with 0.1% NH$_4$OH modifier) to afford the title compound. MS: 363 (M+1). $^1$H NMR (600 MHz, DMSO-d$_6$) δ 9.61 (s, 1H), 8.82 (s, 1H), 8.47 (s, 1H), 8.25 (d, J=8.8 Hz, 1H), 8.10 (d, J=7.6 Hz, 1H), 7.98 (d, J=2.2 Hz, 1H), 7.76 (d, J=8.6 Hz, 1H), 4.17-4.13 (m, 1H), 2.68 (s, 3H), 2.26-2.16 (m, 7H), 2.04 (d, J=12.0 Hz, 2H), 1.86 (d, J=12.2 Hz, 2H), 1.46-1.40 (m, 2H), 1.35-1.29 (m, 2H).

The following examples in Table 4 were prepared in an analogous manner of those described in Example 1-1 and general scheme 1.

TABLE 4

| Example # | Structure | Chemical Name | MS (M + 1) |
|---|---|---|---|
| 1-2 | 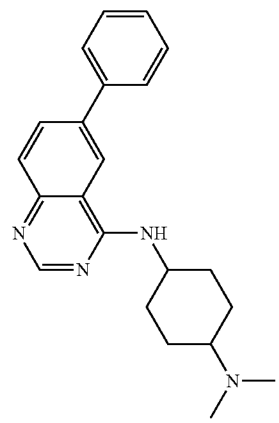 [SMILES: CN(C)C1CCC(Nc2ncnc3ccc(-c4ccccc4)cc23)CC1] | cis or trans-N,N-dimethyl-N'-(6-phenylquinazolin-4-yl)cyclohexane-1,4-diamine | Calc'd 347.0, found 347 |
| 1-3 | 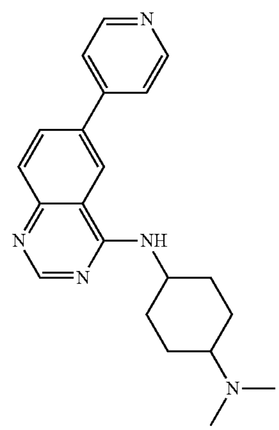 [SMILES: CN(C)C1CCC(Nc2ncnc3ccc(-c4ccncc4)cc23)CC1] | cis or trans-N,N-dimethyl-N'-[6-(pyridin-4-yl)quinazolin-4-yl]cyclohexane-1,4-diamine | Calc'd 348.0, found 348 |
| 1-4 | 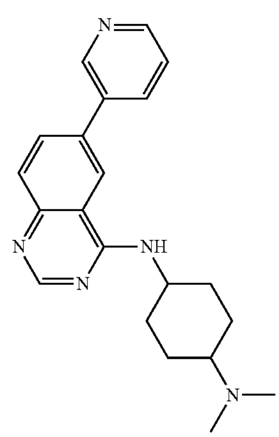 [SMILES: CN(C)C1CCC(Nc2ncnc3ccc(-c4cccnc4)cc23)CC1] | cis or trans-N,N-dimethyl-N'-[6-(pyridin-3-yl)quinazolin-4-yl]cyclohexane-1,4-diamine | Calc'd 348.0, found 348 |

TABLE 4-continued

| Example # | Structure | Chemical Name | MS (M + 1) |
|---|---|---|---|
| 1-5 | 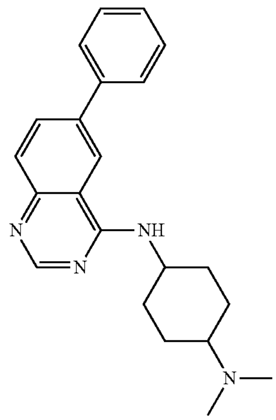 [SMILES: CN(C)C1CCC(Nc2ncnc3ccc(-c4ccccc4)cc23)CC1] | cis or trans-N,N-dimethyl-N'-(6-phenylquinazolin-4-yl)cyclohexane-1,4-diamine | Calc'd 347.0, found 347 |
| 1-6 | 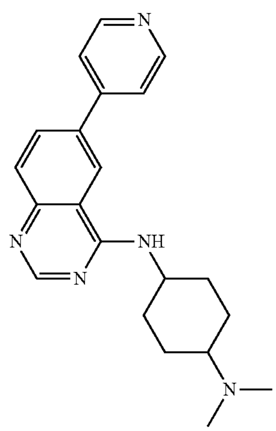 [SMILES: CN(C)C1CCC(Nc2ncnc3ccc(-c4ccncc4)cc23)CC1] | cis or trans-N,N-dimethyl-N'-[6-(pyridin-4-yl)quinazolin-4-yl]cyclohexane-1,4-diamine | Calc'd 348.0, found 348 |
| 1-7 | 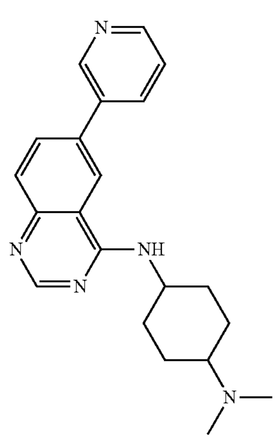 [SMILES: CN(C)C1CCC(Nc2ncnc3ccc(-c4cccnc4)cc23)CC1] | cis or trans-N,N-dimethyl-N'-[6-(pyridin-3-yl)quinazolin-4-yl]cyclohexane-1,4-diamine | Calc'd 348.0, found 348 |

TABLE 4-continued

| Example # | Structure | Chemical Name | MS (M + 1) |
|---|---|---|---|
| 1-8 | 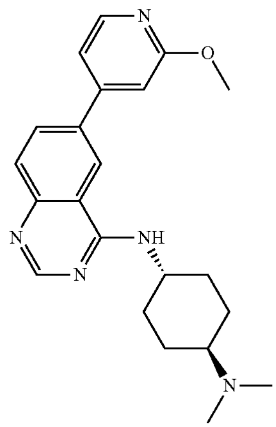 [SMILES: COc1cc(-c2ccc3ncnc(N[C@H]4CC[C@H](N(C)C)CC4)c3c2)ccn1] | trans-N'-[6-(2-methoxypyridin-4-yl)quinazolin-4-yl]-N,N-dimethylcyclohexane-1,4-diamine | Calc'd 378.0, found 378 |
| 1-9 | 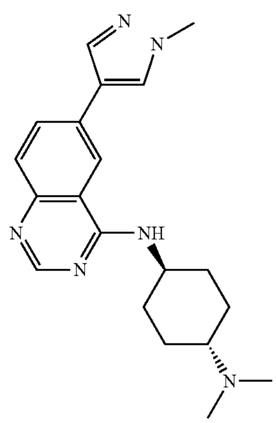 [SMILES: CN/C=C(\C=N)c1ccc2ncnc(N[C@H]3CC[C@H](N(C)C)CC3)c2c1] | trans-N,N-dimethyl-N'-[6-(1-methyl-1H-pyrazol-4-yl)quinazolin-4-yl]cyclohexane-1,4-diamine | Calc'd 351.0, found 351 |
| 1-10 | 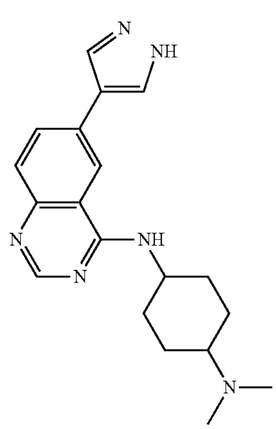 [SMILES: CN(C)C1CCC(Nc2ncnc3ccc(/C(C=N)=C/N)cc23)CC1] | cis or trans-N,N-dimethyl-N'-[6-(1H-pyrazol-4-yl)quinazolin-4-yl]cyclohexane-1,4-diamine | Calc'd 337.0, found 337 |

TABLE 4-continued

| Example # | Structure | Chemical Name | MS (M + 1) |
|---|---|---|---|
| 1-11 | 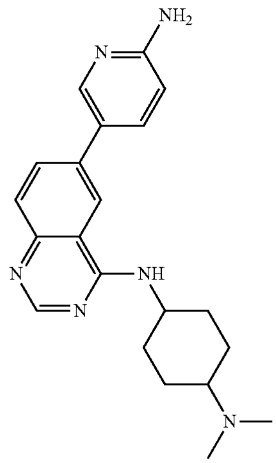 [SMILES: CN(C)C1CCC(Nc2ncnc3ccc(-c4ccc(N)nc4)cc23)CC1] | cis or trans-N'-[6-(6-aminopyridin-3-yl)quinazolin-4-yl]-N,N-dimethylcyclohexane-1,4-diamine | Calc'd 363.0, found 363 |
| 1-12 | 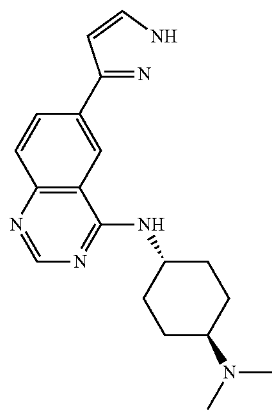 [SMILES: CN(C)[C@H]1CC[C@H](Nc2ncnc3ccc(C(=N)/C=C\N)cc23)CC1] | trans-N,N-dimethyl-N'-[6-(1H-pyrazol-3-yl)quinazolin-4-yl]cyclohexane-1,4-diamine | Calc'd 337.0, found 337 |
| 1-13 | 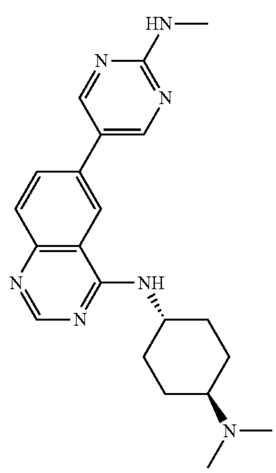 [SMILES: CNc1ncc(-c2ccc3ncnc(N[C@H]4CC[C@H](N(C)C)CC4)c3c2)cn1] | trans-N,N-dimethyl-N'-{6-[2-(methylamino)pyrimidin-5-yl]quinazolin-4-yl}cyclohexane-1,4-diamine | Calc'd 378.0, found 378 |

TABLE 4-continued

| Example # | Structure | Chemical Name | MS (M + 1) |
|---|---|---|---|
| 1-14 | 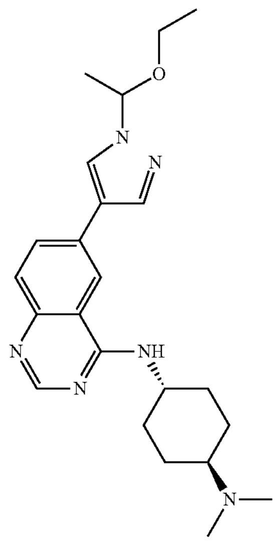 [SMILES: CCOC(C)N/C=C(\C=N)c1ccc2ncnc(N[C@H]3CC[C@H](N(C)C)CC3)c2c1] | trans-N'-{6-[1-(1-ethoxyethyl)-1H-pyrazol-4-yl]quinazolin-4-yl}-N,N-dimethylcyclohexane-1,4-diamine | Calc'd 409.0, found 409 |
| 1-15 | 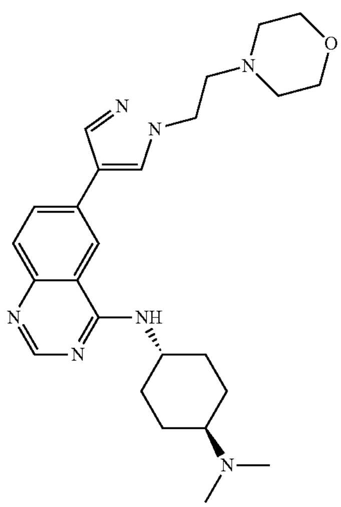 [SMILES: CN(C)[C@H]1CC[C@H](Nc2ncnc3ccc(/C(C=N)=C/NCCN4CCOCC4)cc23)CC1] | trans-N,N-dimethyl-N'-(6-{1-[2-(morpholin-4-yl)ethyl]-1H-pyrazol-4-yl}quinazolin-4-yl)cyclohexane-1,4-diamine | Calc'd 450.0, found 450 |
| 1-16 | 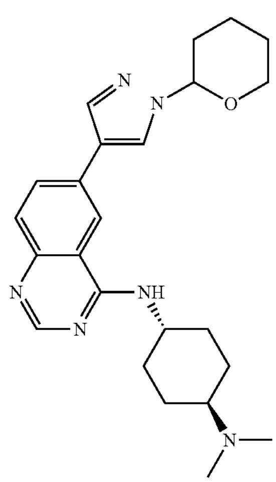 [SMILES: CN(C)[C@H]1CC[C@H](Nc2ncnc3ccc(/C(C=N)=C/NC4CCCCO4)cc23)CC1] | trans-N,N-dimethyl-N'-{6-[1-(tetrahydro-2H-pyran-2-yl)-1H-pyrazol-4-yl]quinazolin-4-yl}cyclohexane-1,4-diamine | Calc'd 421.0, found 421 |

TABLE 4-continued

| Example # | Structure | Chemical Name | MS (M + 1) |
|---|---|---|---|
| 1-17 | 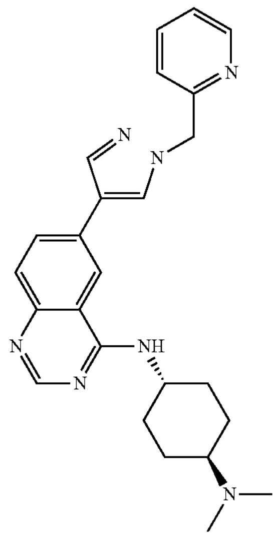 [SMILES: CN(C)[C@H]1CC[C@H](Nc2ncnc3ccc(/C(C=N)=C/NCc4ccccn4)cc23)CC1] | trans-N,N-dimethyl-N'-{6-[1-(pyridin-2-ylmethyl)-1H-pyrazol-4-yl]quinazolin-4-yl}cyclohexane-1,4-diamine | Calc'd 428.0, found 428 |
| 1-18 | 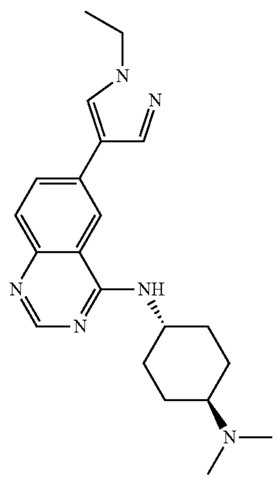 [SMILES: CCN/C=C(\C=N)c1ccc2ncnc(N[C@H]3CC[C@H](N(C)C)CC3)c2c1] | trans-N'-[6-(1-ethyl-1H-pyrazol-4-yl)quinazolin-4-yl]-N,N-dimethylcyclohexane-1,4-diamine | Calc'd 365.0, found 365 |
| 1-19 | 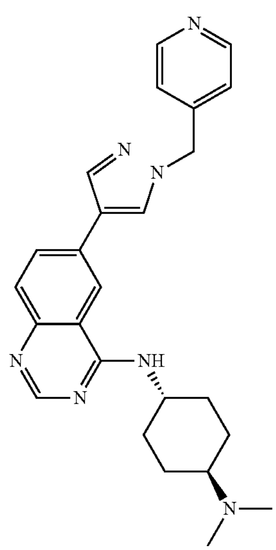 [SMILES: CN(C)[C@H]1CC[C@H](Nc2ncnc3ccc(/C(C=N)=C/NCc4ccncc4)cc23)CC1] | trans-N,N-dimethyl-N'-{6-[1-(pyridin-4-ylmethyl)-1H-pyrazol-4-yl]quinazolin-4-yl}cyclohexane-1,4-diamine | Calc'd 428.0, found 428 |

TABLE 4-continued
| Example # | Structure | Chemical Name | MS (M + 1) |
|---|---|---|---|
| 1-20 | 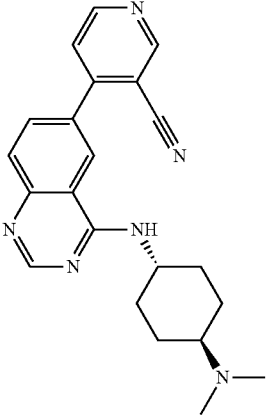 [SMILES: CN(C)[C@H]1CC[C@H](Nc2ncnc3ccc(-c4ccncc4C#N)cc23)CC1] | 4-(4-{[trans-4-(dimethylamino)cyclohexyl]amino}quinazolin-6-yl)pyridine-3-carbonitrile | Calc'd 373.0, found 373 |
| 1-21 | 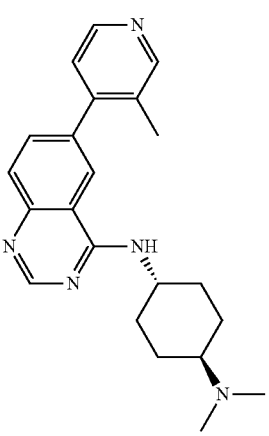 [SMILES: Cc1cnccc1-c1ccc2ncnc(N[C@H]3CC[C@H](N(C)C)CC3)c2c1] | trans-N,N-dimethyl-N'-[6-(3-methylpyridin-4-yl)quinazolin-4-yl]cyclohexane-1,4-diamine | Calc'd 362.0, found 362 |
| 1-22 | 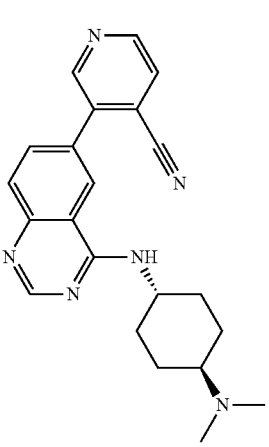 [SMILES: CN(C)[C@H]1CC[C@H](Nc2ncnc3ccc(-c4cnccc4C#N)cc23)CC1] | 3-(4-{[trans-4-(dimethylamino)cyclohexyl]amino}quinazolin-6-yl)pyridine-4-carbonitrile | Calc'd 373.0, found 373 |

TABLE 4-continued

| Example # | Structure | Chemical Name | MS (M + 1) |
|---|---|---|---|
| 1-23 | 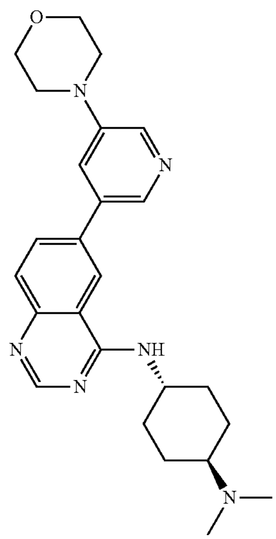 [SMILES: CN(C)[C@H]1CC[C@H](Nc2ncnc3ccc(-c4cncc(N5CCOCC5)c4)cc23)CC1] | trans-N,N-dimethyl-N'-{6-[5-(morpholin-4-yl)pyridin-3-yl]quinazolin-4-yl}cyclohexane-1,4-diamine | Calc'd 433.0, found 433 |
| 1-24 | 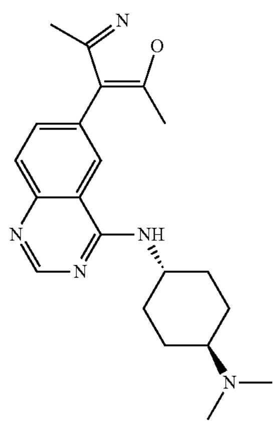 [SMILES: CC(=N)/C(=C(/C)O)c1ccc2ncnc(N[C@H]3CC[C@H](N(C)C)CC3)c2c1] | trans-N'-[6-(3,5-dimethylisoxazol-4-yl)quinazolin-4-yl]-N,N-dimethylcyclohexane-1,4-diamine | Calc'd 366.0, found 366 |
| 1-25 | 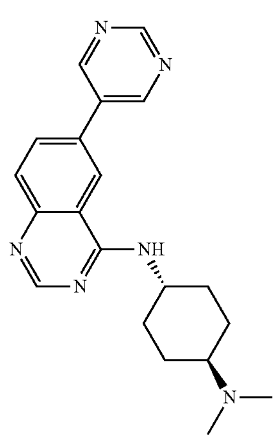 [SMILES: CN(C)[C@H]1CC[C@H](Nc2ncnc3ccc(-c4cncnc4)cc23)CC1] | trans-N,N-dimethyl-N'-[6-(pyrimidin-5-yl)quinazolin-4-yl]cyclohexane-1,4-diamine | Calc'd 349.0, found 349 |

TABLE 4-continued

| Example # | Structure | Chemical Name | MS (M + 1) |
|---|---|---|---|
| 1-26 | 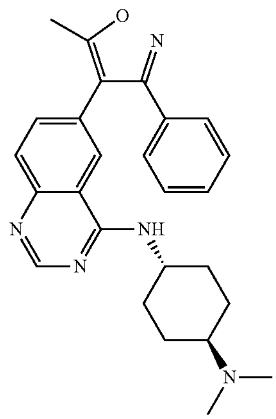 [SMILES: C/C(O)=C(/C(=N)c1ccccc1)c1ccc2ncnc(N[C@H]3CC[C@H](N(C)C)CC3)c2c1] | trans-N,N-dimethyl-N'-[6-(5-methyl-3-phenylisoxazol-4-yl)quinazolin-4-yl]cyclohexane-1,4-diamine | Calc'd 428.0, found 428 |
| 1-27 | 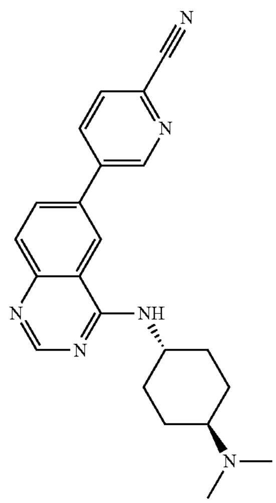 [SMILES: CN(C)[C@H]1CC[C@H](Nc2ncnc3ccc(-c4ccc(C#N)nc4)cc23)CC1] | 5-(4-{[trans-4-(dimethylamino)cyclohexyl]amino}quinazolin-6-yl)pyridine-2-carbonitrile | Calc'd 373.0, found 373 |
| 1-28 | 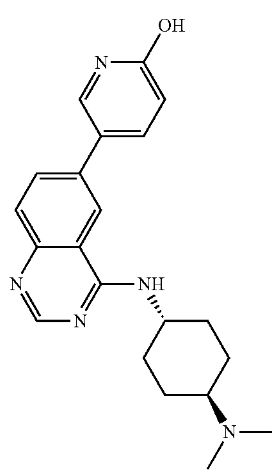 [SMILES: CN(C)[C@H]1CC[C@H](Nc2ncnc3ccc(-c4ccc(O)nc4)cc23)CC1] | 5-(4-{[trans-4-(dimethylamino)cyclohexyl]amino}quinazolin-6-yl)pyridin-2-ol | Calc'd 364.0, found 364 |

TABLE 4-continued

| Example # | Structure | Chemical Name | MS (M + 1) |
|---|---|---|---|
| 1-29 | 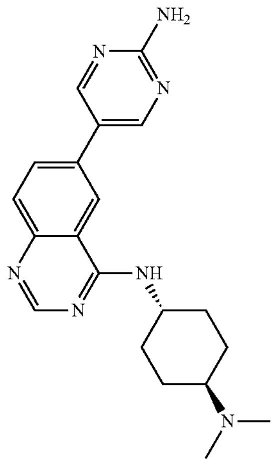 [SMILES: CN(C)[C@H]1CC[C@H](Nc2ncnc3ccc(-c4cnc(N)nc4)cc23)CC1] | trans-N'-[6-(2-aminopyrimidin-5-yl)quinazolin-4-yl]-N,N-dimethylcyclohexane-1,4-diamine | Calc'd 364.0, found 364 |
| 1-30 | 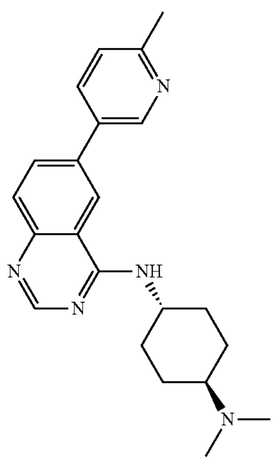 [SMILES: Cc1ccc(-c2ccc3ncnc(N[C@H]4CC[C@H](N(C)C)CC4)c3c2)cn1] | trans-N,N-dimethyl-N'-[6-(6-methylpyridin-3-yl)quinazolin-4-yl]cyclohexane-1,4-diamine | Calc'd 362.0, found 362 |
| 1-31 | 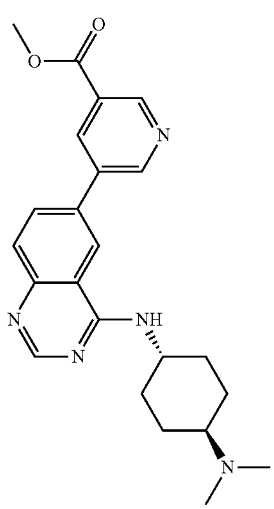 [SMILES: COC(=O)c1cncc(-c2ccc3ncnc(N[C@H]4CC[C@H](N(C)C)CC4)c3c2)c1] | methyl 5-(4-{[trans-4-(dimethylamino)cyclohexyl]amino}quinazolin-6-yl)pyridine-3-carboxylate | Calc'd 406.0, found 406 |

TABLE 4-continued

| Example # | Structure | Chemical Name | MS (M + 1) |
|---|---|---|---|
| 1-32 | 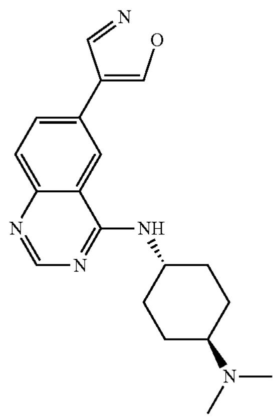 [SMILES: CN(C)[C@H]1CC[C@H](Nc2ncnc3ccc(/C(C=N)=C/O)cc23)CC1] | trans-N'-6-(isoxazol-4-yl)quinazolin-4-yl]-N,N-dimethylcyclohexane-1,4-diamine | Calc'd 338.0, found 338 |
| 1-33 | 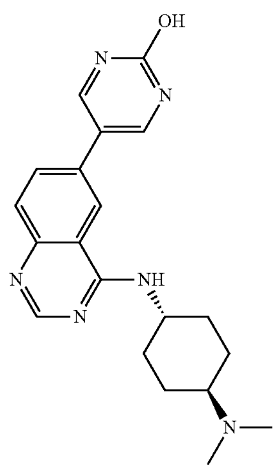 [SMILES: CN(C)[C@H]1CC[C@H](Nc2ncnc3ccc(-c4cnc(O)nc4)cc23)CC1] | 5-(4-{[trans-4-(dimethylamino)cyclohexyl]amino}quinazolin-6-yl)pyrimidin-2-ol | Calc'd 365.0, found 365 |
| 1-34 | 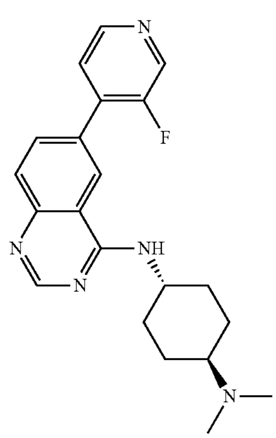 [SMILES: CN(C)[C@H]1CC[C@H](Nc2ncnc3ccc(-c4ccncc4F)cc23)CC1] | trans-N'-[6-(3-fluoropyridin-4-yl)quinazolin-4-yl]-N,N-dimethylcyclohexane-1,4-diamine | Calc'd 366.0, found 366 |

TABLE 4-continued
| Example # | Structure | Chemical Name | MS (M + 1) |
|---|---|---|---|
| 1-35 | 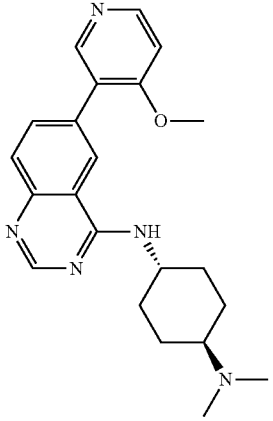 [SMILES: COc1ccncc1-c1ccc2ncnc(N[C@H]3CC[C@H](N(C)C)CC3)c2c1] | trans-N'-[6-(4-methoxypyridin-3-yl)quinazolin-4-yl]-N,N-dimethylcyclohexane-1,4-diamine | Calc'd 378.0, found 378 |
| 1-36 | 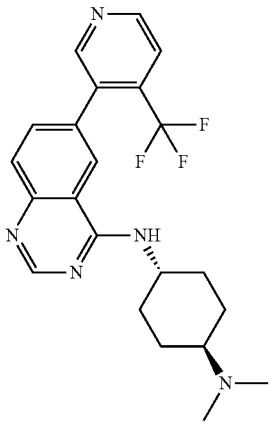 [SMILES: CN(C)[C@H]1CC[C@H](Nc2ncnc3ccc(-c4cnccc4C(F)(F)F)cc23)CC1] | trans-N,N-dimethyl-N'-{6-[4-(trifluoromethyl)pyridin-3-yl]quinazolin-4-yl}cyclohexane-1,4-diamine | Calc'd 416.0, found 416 |
| 1-37 | 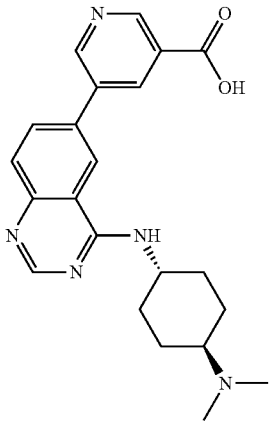 [SMILES: CN(C)[C@H]1CC[C@H](Nc2ncnc3ccc(-c4cncc(C(=O)O)c4)cc23)CC1] | 5-(4-{[trans-4-(dimethylamino)cyclohexyl]amino}quinazolin-6-yl)pyridine-3-carboxylic acid | Calc'd 392.0, found 392 |

TABLE 4-continued

| Example # | Structure | Chemical Name | MS (M + 1) |
|---|---|---|---|
| 1-38 | 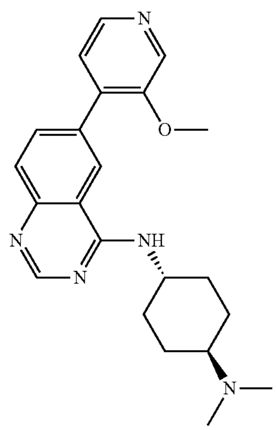 [SMILES: COc1cnccc1-c1ccc2ncnc(N[C@H]3CC[C@H](N(C)C)CC3)c2c1] | trans-N'-[6-(3-methoxypyridin-4-yl)quinazolin-4-yl]-N,N-dimethylcyclohexane-1,4-diamine | Calc'd 378.0, found 378 |
| 1-39 | 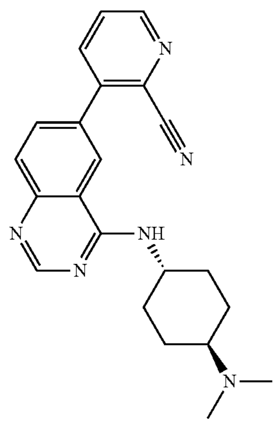 [SMILES: CN(C)[C@H]1CC[C@H](Nc2ncnc3ccc(-c4cccnc4C#N)cc23)CC1] | 3-(4-{[trans-4-(dimethylamino)cyclohexyl]amino}quinazolin-6-yl)pyridine-2-carbonitrile | Calc'd 373.0, found 373 |
| 1-40 | 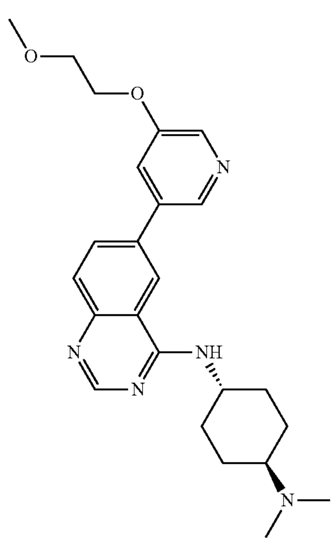 | trans-N'-{6-[5-(2-methoxyethoxy)pyridin-3-yl]quinazolin-4-yl}-N,N-dimethylcyclohexane-1,4-diamine | Calc'd 422.0, found 422 |

TABLE 4-continued

| Example # | Structure | Chemical Name | MS (M + 1) |
|---|---|---|---|
| 1-41 | 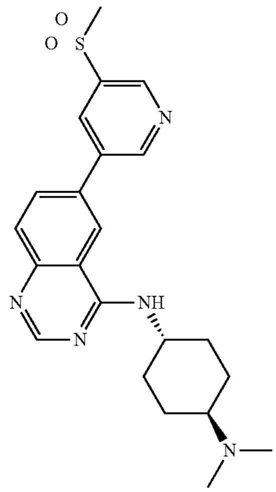 | trans-N,N-dimethyl-N'-{6-[5-(methylsulfonyl)pyridin-3-yl]quinazolin-4-yl}cyclohexane-1,4-diamine | Calc'd 426.0, found 426 |
| 1-42 | 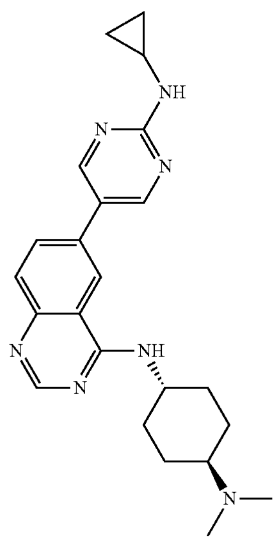 [SMILES: CN(C)[C@H]1CC[C@H](Nc2ncnc3ccc(-c4cnc(NC5CC5)nc4)cc23)CC1] | trans-N'-{6-[2-(cyclopropylamino)pyrimidin-5-yl]quinazolin-4-yl}-N,N-dimethylcyclohexane-1,4-diamine | Calc'd 404.0, found 404 |
| 1-43 | 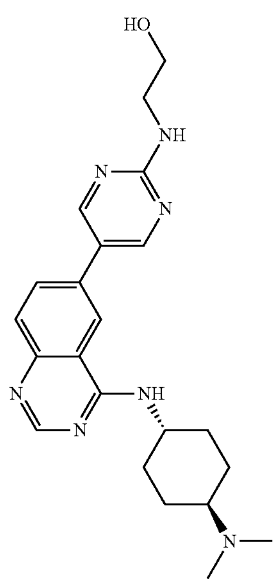 [SMILES: CN(C)[C@H]1CC[C@H](Nc2ncnc3ccc(-c4cnc(NCCO)nc4)cc23)CC1] | 2-{[5-(4-{[trans-4-(dimethylamino)cyclohexyl]amino}quinazolin-6-yl)pyrimidin-2-yl]amino}ethanol | Calc'd 408.0, found 408 |

TABLE 4-continued

| Example # | Structure | Chemical Name | MS (M + 1) |
|---|---|---|---|
| 1-44 | 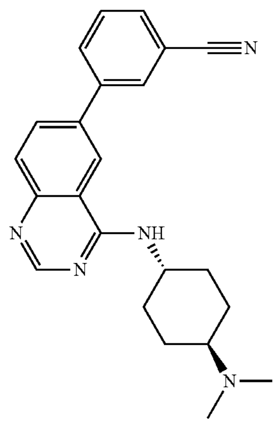 [SMILES: CN(C)[C@H]1CC[C@H](Nc2ncnc3ccc(-c4cccc(C#N)c4)cc23)CC1] | 3-(4-{[trans-4-(dimethylamino)cyclohexyl]amino}quinazolin-6-yl)benzonitrile | Calc'd 372.0, found 372 |
| 1-45 | 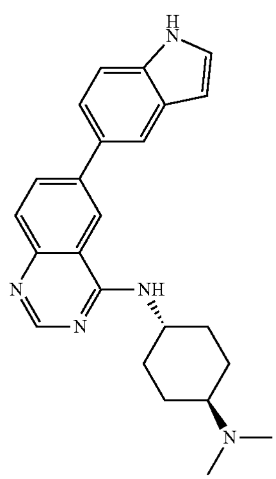 [SMILES: CN(C)[C@H]1CC[C@H](Nc2ncnc3ccc(-c4ccc5[nH]ccc5c4)cc23)CC1] | trans-N'-[6-(1H-indol-5-yl)quinazolin-4-yl]-N,N-dimethylcyclohexane-1,4-diamine | Calc'd 386.0, found 386 |
| 1-46 | 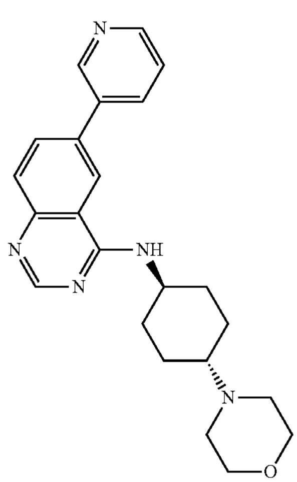 [SMILES: c1cncc(-c2ccc3ncnc(N[C@H]4CC[C@H](N5CCOCC5)CC4)c3c2)c1] | N-[trans-4-(morpholin-4-yl)cyclohexyl]-6-(pyridin-3-yl)quinazolin-4-amine | Calc'd 390.0, found 390 |

TABLE 4-continued

| Example # | Structure | Chemical Name | MS (M + 1) |
|---|---|---|---|
| 1-47 | 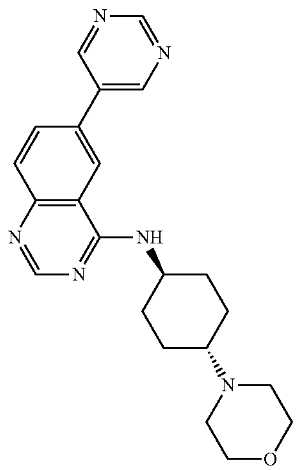 [SMILES: c1ncc(-c2ccc3ncnc(N[C@H]4CC[C@H](N5CCOCC5)CC4)c3c2)cn1] | N-[trans-4-(morpholin-4-yl)cyclohexyl]-6-(pyrimidin-5-yl)quinazolin-4-amine | Calc'd 391.0, found 391 |
| 1-48 | 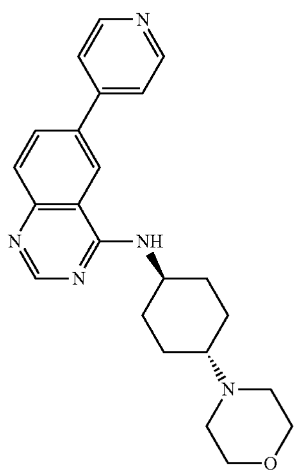 [SMILES: c1cc(-c2ccc3ncnc(N[C@H]4CC[C@H](N5CCOCC5)CC4)c3c2)ccn1] | N-[trans-4-(morpholin-4-yl)cyclohexyl]-6-(pyridin-4-yl)quinazolin-4-amine | Calc'd 390.0, found 390 |
| 1-49 | 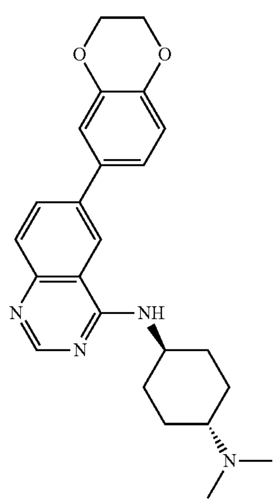 [SMILES: CN(C)[C@H]1CC[C@H](Nc2ncnc3ccc(-c4ccc5c(c4)OCCO5)cc23)CC1] | trans-N'-[6-(2,3-dihydro-1,4-benzodioxin-6-yl)quinazolin-4-yl]-N,N-dimethylcyclohexane-1,4-diamine | Calc'd 405.0, found 405 |

TABLE 4-continued

| Example # | Structure | Chemical Name | MS (M + 1) |
|---|---|---|---|
| 1-50 | 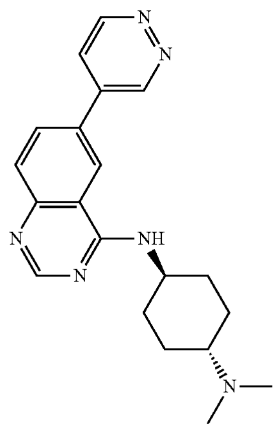 [SMILES: CN(C)[C@H]1CC[C@H](Nc2ncnc3ccc(-c4ccnnc4)cc23)CC1] | trans-N,N-dimethyl-N'-[6-(pyridazin-4-yl)quinazolin-4-yl]cyclohexane-1,4-diamine | Calc'd 349.0, found 349 |
| 1-51 | 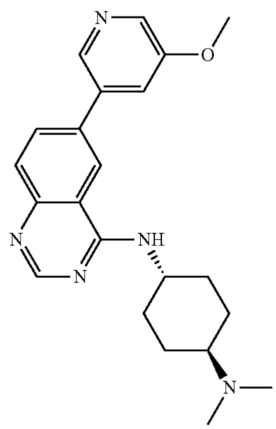 [SMILES: COc1cncc(-c2ccc3ncnc(N[C@H]4CC[C@H](N(C)C)CC4)c3c2)c1] | trans-N'-[6-(5-methoxypyridin-3-yl)quinazolin-4-yl]-N,N-dimethylcyclohexane-1,4-diamine | Calc'd 378.0, found 378 |
| 1-52 | 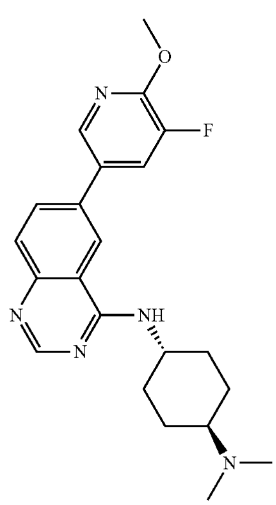 [SMILES: COc1ncc(-c2ccc3ncnc(N[C@H]4CC[C@H](N(C)C)CC4)c3c2)cc1F] | trans-N'-[6-(5-fluoro-6-methoxypyridin-3-yl)quinazolin-4-yl]-N,N-dimethylcyclohexane-1,4-diamine | Calc'd 396.0, found 396 |

TABLE 4-continued

| Example # | Structure | Chemical Name | MS (M + 1) |
| --- | --- | --- | --- |
| 1-53 | 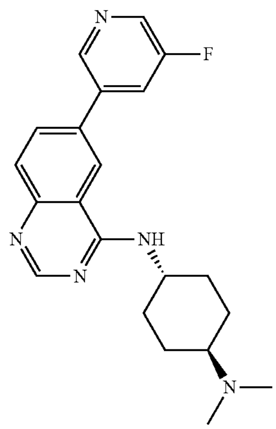 [SMILES: CN(C)[C@H]1CC[C@H](Nc2ncnc3ccc(-c4cncc(F)c4)cc23)CC1] | trans-N'-[6-(5-fluoropyridin-3-yl)quinazolin-4-yl]-N,N-dimethylcyclohexane-1,4-diamine | Calc'd 366.0, found 366 |
| 1-54 | 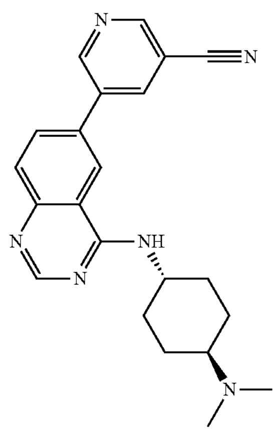 [SMILES: CN(C)[C@H]1CC[C@H](Nc2ncnc3ccc(-c4cncc(C#N)c4)cc23)CC1] | 5-(4-{[trans-4-(dimethylamino)cyclohexyl]amino}quinazolin-6-yl)pyridine-3-carbonitrile | Calc'd 373.0, found 373 |
| 1-55 | 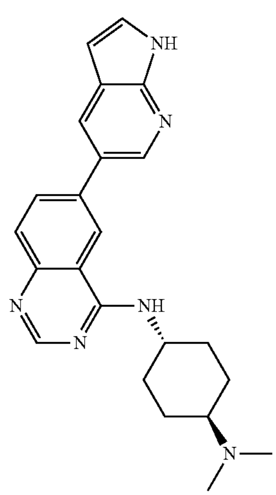 [SMILES: CN(C)[C@H]1CC[C@H](Nc2ncnc3ccc(-c4cnc5[nH]ccc5c4)cc23)CC1] | trans-N,N-dimethyl-N'-[6-(1H-pyrrolo[2,3-b]pyridin-5-yl)quinazolin-4-yl]cyclohexane-1,4-diamine | Calc'd 387.0, found 387 |

TABLE 4-continued

| Example # | Structure | Chemical Name | MS (M + 1) |
|---|---|---|---|
| 1-56 | 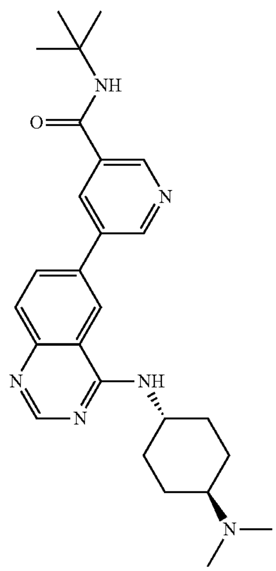 [SMILES: CN(C)[C@H]1CC[C@H](Nc2ncnc3ccc(-c4cncc(C(=O)NC(C)(C)C)c4)cc23)CC1] | N-tert-butyl-5-(4-{[trans-4-(dimethylamino)cyclohexyl]amino}quinazolin-6-yl)pyridine-3-carboxamide | Calc'd 447.0, found 447 |
| 1-57 | 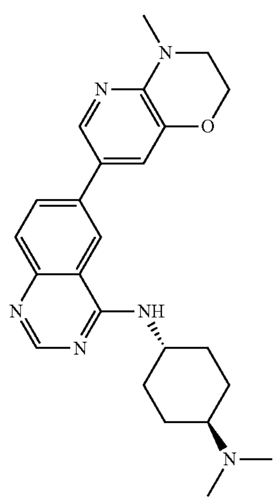 [SMILES: CN1CCOc2cc(-c3ccc4ncnc(N[C@H]5CC[C@H](N(C)C)CC5)c4c3)cnc21] | trans-N,N-dimethyl-N'-[6-(4-methyl-3,4-dihydro-2H-pyrido[3,2-b][1,4]oxazin-7-yl)quinazolin-4-yl]cyclohexane-1,4-diamine | Calc'd 419.0, found 419 |
| 1-58 | 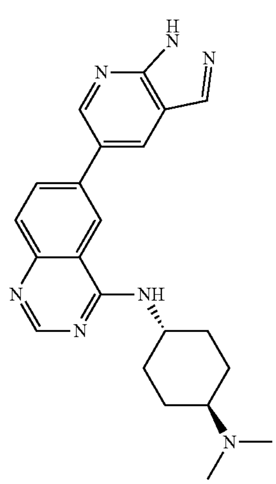 | trans-N,N-dimethyl-N'-[6-(1H-pyrazolo[3,4-b]pyridin-5-yl)quinazolin-4-yl]cyclohexane-1,4-diamine | Calc'd 388.0, found 388 |

TABLE 4-continued

| Example # | Structure | Chemical Name | MS (M + 1) |
|---|---|---|---|
| 1-59 | 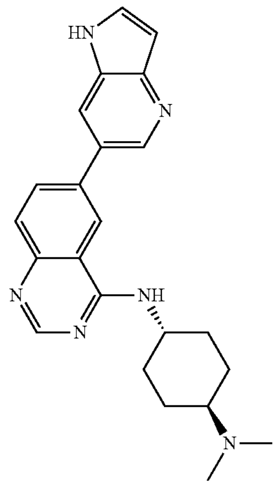 [SMILES: CN(C)[C@H]1CC[C@H](Nc2ncnc3ccc(-c4cnc5cc[nH]c5c4)cc23)CC1] | trans-N,N-dimethyl-N'-[6-(1H-pyrrolo[3,2-b]pyridin-6-yl)quinazolin-4-yl]cyclohexane-1,4-diamine | Calc'd 387.0, found 387 |
| 1-60 | 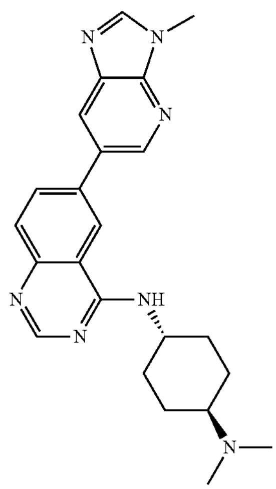 [SMILES: Cn1cnc2cc(-c3ccc4ncnc(N[C@H]5CC[C@H](N(C)C)CC5)c4c3)cnc21] | trans-N,N-dimethyl-N'-[6-(3-methyl-3H-imidazo[4,5-b]pyridin-6-yl)quinazolin-4-yl]cyclohexane-1,4-diamine | Calc'd 402.0, found 402 |
| 1-61 | 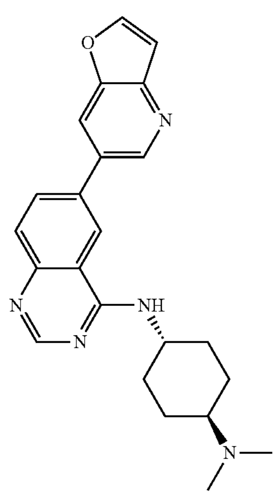 [SMILES: CN(C)[C@H]1CC[C@H](Nc2ncnc3ccc(-c4cnc5ccoc5c4)cc23)CC1] | trans-N'-[6-(furo[3,2-b]pyridin-6-yl)quinazolin-4-yl]-N,N-dimethylcyclohexane-1,4-diamine | Calc'd 388.0, found 388 |

TABLE 4-continued

| Example # | Structure | Chemical Name | MS (M + 1) |
|---|---|---|---|
| 1-62 | 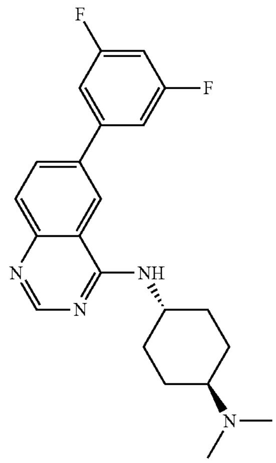 [SMILES: CN(C)[C@H]1CC[C@H](Nc2ncnc3ccc(-c4cc(F)cc(F)c4)cc23)CC1] | trans-N'-[6-3,5-difluorophenyl)quinazolin-4-yl]-N,N-dimethylcyclohexane-1,4-diamine | Calc'd 383.0, found 383 |
| 1-63 | 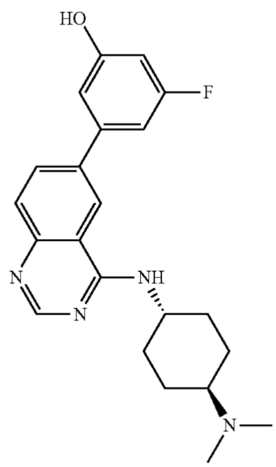 [SMILES: CN(C)[C@H]1CC[C@H](Nc2ncnc3ccc(-c4cc(O)cc(F)c4)cc23)CC1] | 3-(4-{[trans-4-(dimethylamino)cyclohexyl]amino}quinazolin-6-yl)-5-fluorophenol | Calc'd 381.0, found 381 |
| 1-64 | 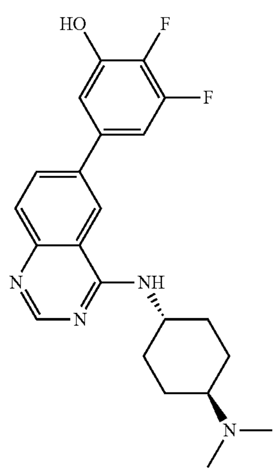 [SMILES: CN(C)[C@H]1CC[C@H](Nc2ncnc3ccc(-c4cc(O)c(F)c(F)c4)cc23)CC1] | 5-(4-{[trans-4-(dimethylamino)cyclohexyl]amino}quinazolin-6-yl)-2,3-difluorophenol | Calc'd 399.0, found 399 |

TABLE 4-continued
| Example # | Structure | Chemical Name | MS (M + 1) |
|---|---|---|---|
| 1-65 | 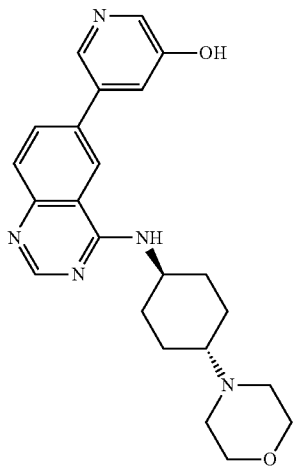 [SMILES: Oc1cncc(-c2ccc3ncnc(N[C@H]4CC[C@H](N5CCOCC5)CC4)c3c2)c1] | 5-(4-{[trans-4-(morpholin-4-yl)cyclohexyl]amino}quinazolin-6-yl)pyridin-3-ol | Calc'd 406.0, found 406 |
| 1-66 | 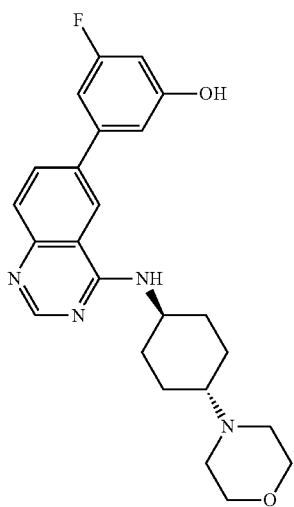 [SMILES: Oc1cc(F)cc(-c2ccc3ncnc(N[C@H]4CC[C@H](N5CCOCC5)CC4)c3c2)c1] | 3-fluoro-5-{4-[(trans-4-morpholin-4-ylcyclohexyl)amino]quinazolin-6-yl}phenol | Calc'd 423.0, found 423 |
| 1-67 | 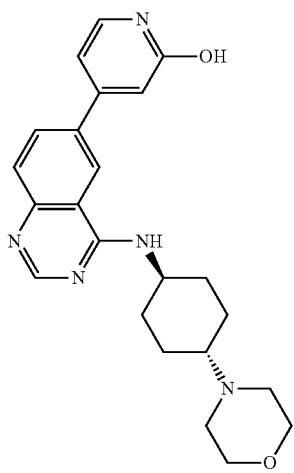 | 4-{4-[(trans-4-morpholin-4-ylcyclohexyl)amino]quinazolin-6-yl}pyridin-2-ol | Calc'd 406.0, found 406 |

TABLE 4-continued

| Example # | Structure | Chemical Name | MS (M + 1) |
|---|---|---|---|
| 1-68 | 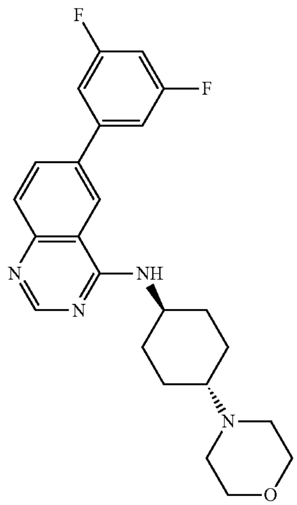 [SMILES: Fc1cc(F)cc(-c2ccc3ncnc(N[C@H]4CC[C@H](N5CCOCC5)CC4)c3c2)c1] | 6-(3,5-difluorophenyl)-N-(trans-4-morpholin-4-ylcyclohexyl)quinazolin-4-amine | Calc'd 425.0, found 425 |
| 1-69 | 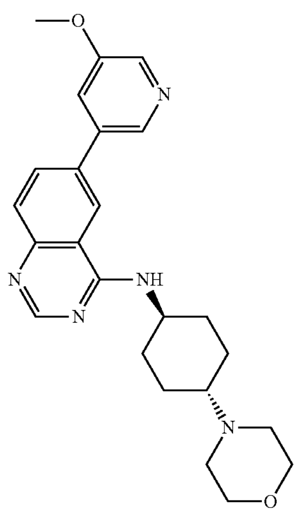 [SMILES: COc1cncc(-c2ccc3ncnc(N[C@H]4CC[C@H](N5CCOCC5)CC4)c3c2)c1] | 6-(5-methoxypyridin-3-yl)-N-[trans-4-(morpholin-4-yl)cyclohexyl]quinazolin-4-amine | Calc'd 420.0, found 420 |
| 1-70 | 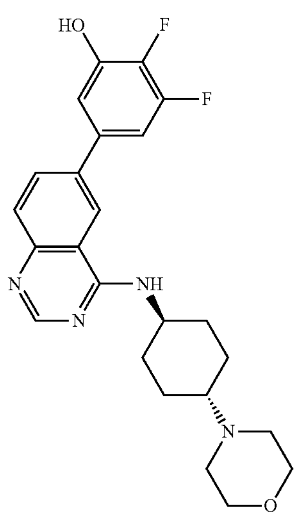 [SMILES: Oc1cc(-c2ccc3ncnc(N[C@H]4CC[C@H](N5CCOCC5)CC4)c3c2)cc(F)c1F] | 2,3-difluoro-5-{4-[(trans-4-morpholin-4-ylcyclohexyl)amino]quinazolin-6-yl}phenol | Calc'd 441.0, found 441 |

TABLE 4-continued

| Example # | Structure | Chemical Name | MS (M + 1) |
|---|---|---|---|
| 1-71 | 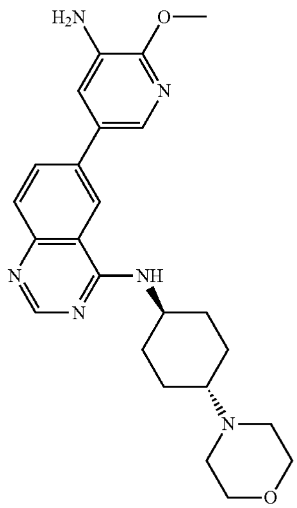 [SMILES: COc1ncc(-c2ccc3ncnc(N[C@H]4CC[C@H](N5CCOCC5)CC4)c3c2)cc1N] | 6-(5-amino-6-methoxypyridin-3-yl)-N-(trans-4-morpholin-4-ylcyclohexyl)quinazolin-4-amine | Calc'd 435.0, found 435 |
| 1-72 | 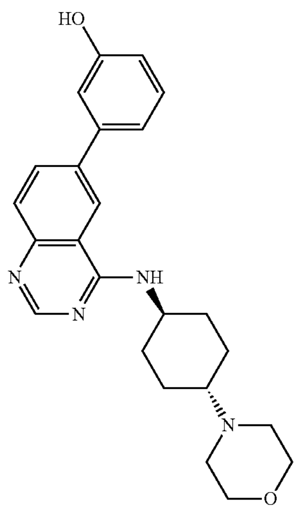 [SMILES: Oc1cccc(-c2ccc3ncnc(N[C@H]4CC[C@H](N5CCOCC5)CC4)c3c2)c1] | 3-{4-[(trans-4-morpholin-4-ylcyclohexyl)amino]quinazolin-6-yl}phenol | Calc'd 405.0, found 405 |
| 1-73 | 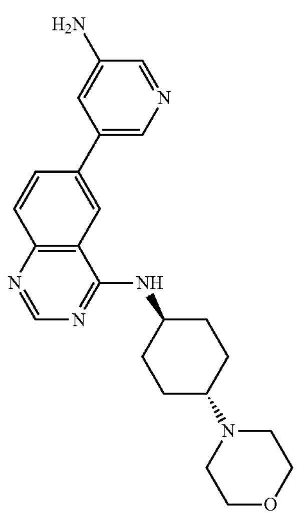 [SMILES: Nc1cncc(-c2ccc3ncnc(N[C@H]4CC[C@H](N5CCOCC5)CC4)c3c2)c1] | 6-(5-aminopyridin-3-yl)-N-(trans-4-morpholin-4-ylcyclohexyl)quinazolin-4-amine | Calc'd 405.0, found 405 |

TABLE 4-continued

| Example # | Structure | Chemical Name | MS (M + 1) |
|---|---|---|---|
| 1-74 | 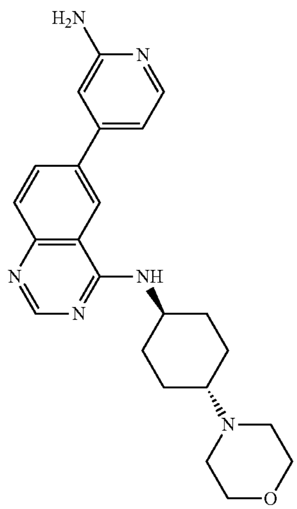 [SMILES: Nc1cc(-c2ccc3ncnc(N[C@H]4CC[C@H](N5CCOCC5)CC4)c3c2)ccn1] | 6-(2-aminopyridin-4-yl)-N-(trans-4-morpholin-4-ylcyclohexyl)quinazolin-4-amine | Calc'd 405.0, found 405 |
| 1-75 | 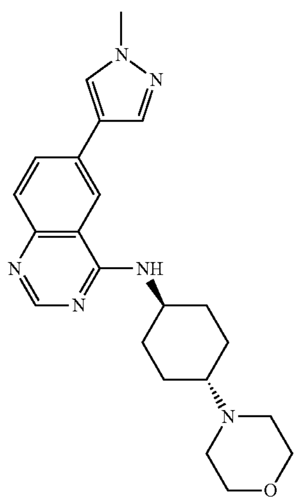 [SMILES: Cn1cc(-c2ccc3ncnc(N[C@H]4CC[C@H](N5CCOCC5)CC4)c3c2)cn1] | 6-(1-methyl-1H-pyrazol-4-yl)-N-(trans-4-morpholin-4-ylcyclohexyl)quinazolin-4-amine | Calc'd 393.0, found 393 |
| 1-76 | 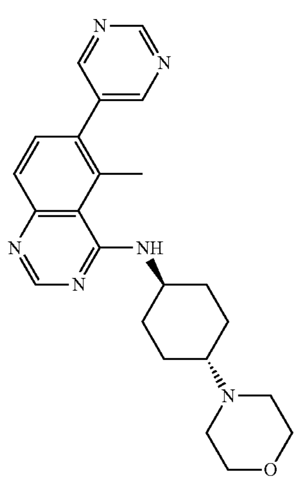 [SMILES: Cc1c(-c2cncnc2)ccc2ncnc(N[C@H]3CC[C@H](N4CCOCC4)CC3)c12] | 5-methyl-N-(trans-4-morpholin-4-ylcyclohexyl)-6-pyrimidin-5-ylquinazolin-4-amine | Calc'd 405.0, found 405 |

TABLE 4-continued

| Example # | Structure | Chemical Name | MS (M + 1) |
|---|---|---|---|
| 1-77 | 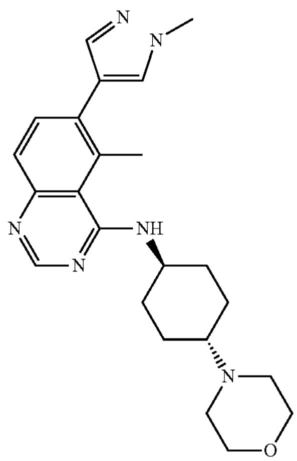 [SMILES: CN/C=C(\C=N)c1ccc2ncnc(N[C@H]3CC[C@H](N4CCOCC4)CC3)c2c1C] | 5-methyl-6-(1-methyl-1H-pyrazol-4-yl)-N-(trans-4-morpholin-4-ylcyclohexyl)quinazolin-4-amine | Calc'd 407.0, found 407 |
| 1-78 | 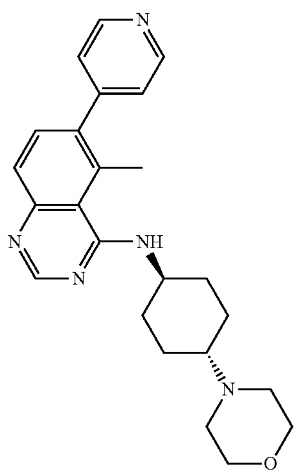 [SMILES: Cc1c(-c2ccncc2)ccc2ncnc(N[C@H]3CC[C@H](N4CCOCC4)CC3)c12] | 5-methyl-N-(trans-4-morpholin-4-ylcyclohexyl)-6-pyridin-4-ylquinazolin-4-amine | Calc'd 404.0, found 404 |
| 1-79 | 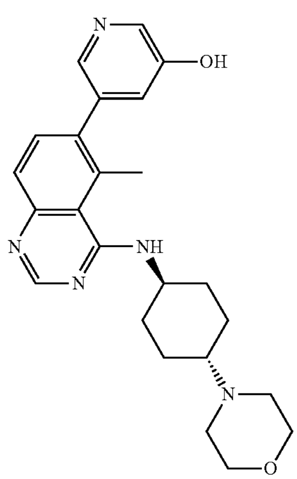 [SMILES: Cc1c(-c2cncc(O)c2)ccc2ncnc(N[C@H]3CC[C@H](N4CCOCC4)CC3)c12] | 5-{5-methyl-4-[(trans-4-morpholin-4-ylcyclohexyl)amino]quinazolin-6-yl}pyridin-3-ol | Calc'd 420.0, found 420 |

TABLE 4-continued

| Example # | Structure | Chemical Name | MS (M + 1) |
|---|---|---|---|
| 1-80 | 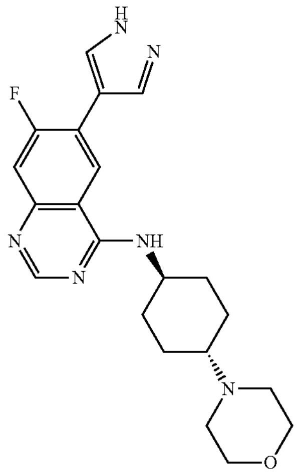 | 7-fluoro-N-(trans-4-morpholin-4-ylcyclohexyl)-6-(1H-pyrazol-4-yl)quinazolin-4-amine | Calc'd 397.0, found 397 |
| 1-81 | 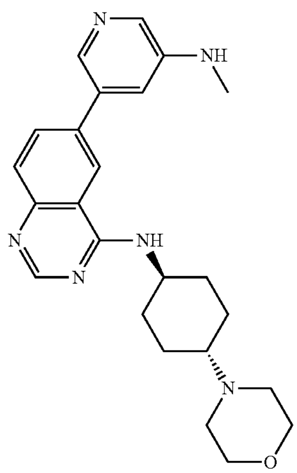 [SMILES: CNc1cncc(-c2ccc3ncnc(N[C@H]4CC[C@H](N5CCOCC5)CC4)c3c2)c1] | 6-[5-(methylamino)pyridin-3-yl]-N-(trans-4-morpholin-4-ylcyclohexyl)quinazolin-4-amine | Calc'd 419.0, found 419 |
| 1-82 | 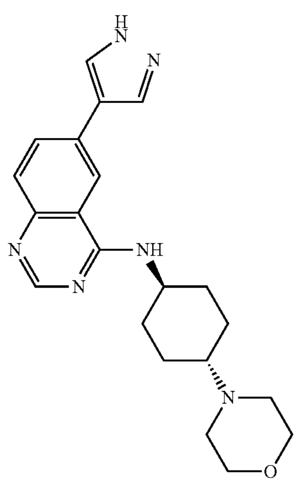 | N-(trans-4-morpholin-4-ylcyclohexyl)-6-(1H-pyrazol-4-yl)quinazolin-4-amine | Calc'd 379.0, found 379 |

TABLE 4-continued

| Example # | Structure | Chemical Name | MS (M + 1) |
|---|---|---|---|
| 1-83 | 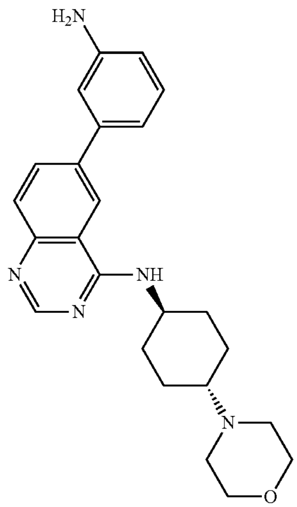 | 6-(3-aminophenyl)-N-(trans-4-morpholin-4-ylcyclohexyl)quinazolin-4-amine | Calc'd 404.0, found 404 |
| 1-84 | 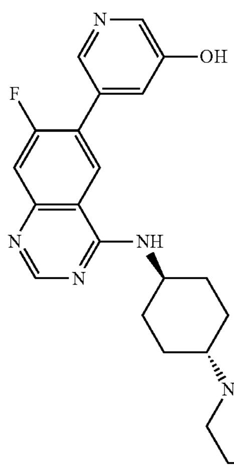 | 5-{7-fluoro-4-[(trans-4-morpholin-4-ylcyclohexyl)amino]quinazolin-6-yl}pyridin-3-ol | Calc'd 424.0, found 424 |
| 1-85 | 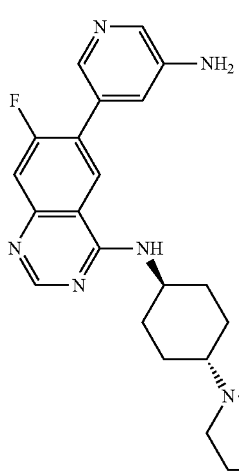 | 6-(5-aminopyridin-3-yl)-7-fluoro-N-(trans-4-morpholin-4-ylcyclohexyl)quinazolin-4-amine | Calc'd 423.0, found 423 |

TABLE 4-continued

| Example # | Structure | Chemical Name | MS (M + 1) |
|---|---|---|---|
| 1-86 | 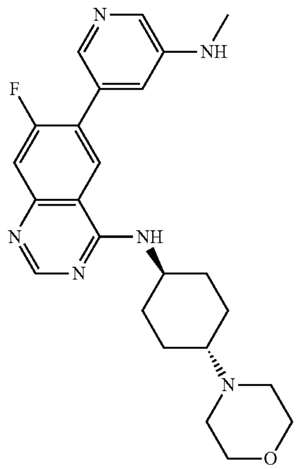 [SMILES: CNc1cncc(-c2cc3c(N[C@H]4CC[C@H](N5CCOCC5)CC4)ncnc3cc2F)c1] | 7-fluoro-6-[5-(methylamino)pyridin-3-yl]-N-(trans-4-morpholin-4-ylcyclohexyl)quinazolin-4-amine | Calc'd 437.0, found 437 |
| 1-87 | 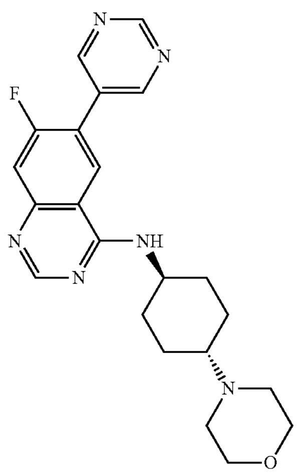 [SMILES: Fc1cc2ncnc(N[C@H]3CC[C@H](N4CCOCC4)CC3)c2cc1-c1cncnc1] | 7-fluoro-N-(trans-4-morpholin-4-ylcyclohexyl)-6-pyrimidin-5-ylquinazolin-4-amine | Calc'd 409.0, found 409 |
| 1-88 | 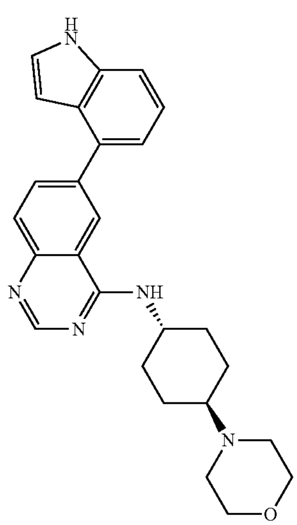 [SMILES: c1cc(-c2ccc3ncnc(N[C@H]4CC[C@H](N5CCOCC5)CC4)c3c2)c2cc[nH]c2c1] | 6-(1H-indol-4-yl)-N-[trans-4-(morpholin-4-yl)cyclohexyl]quinazolin-4-amine | Calc'd 428.0, found 428 |

TABLE 4-continued

| Example # | Structure | Chemical Name | MS (M + 1) |
|---|---|---|---|
| 1-89 | 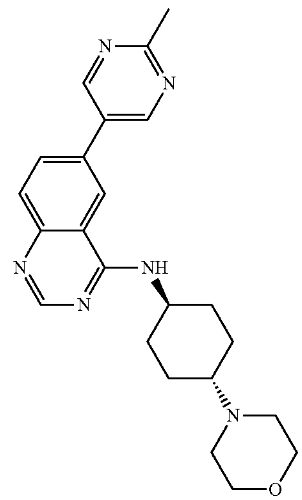 [SMILES: Cc1ncc(-c2ccc3ncnc(N[C@H]4CC[C@H](N5CCOCC5)CC4)c3c2)cn1] | 6-(2-methylpyrimidin-5-yl)-N-[trans-4-(morpholin-4-yl)cyclohexyl]quinazolin-4-amine | Calc'd 405.0, found 405 |
| 1-90 | 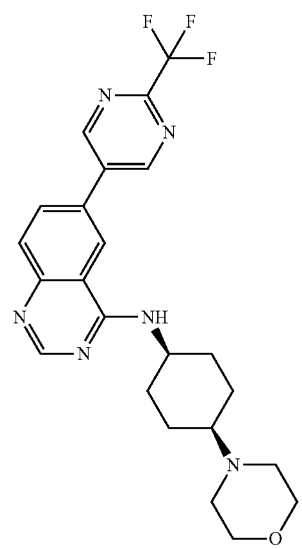 [SMILES: FC(F)(F)c1ncc(-c2ccc3ncnc(N[C@H]4CC[C@@H](N5CCOCC5)CC4)c3c2)cn1] | N-[cis-4-(morpholin-4-yl)cyclohexyl]-6-[2-(trifluoromethyl)pyrimidin-5-yl]quinazolin-4-amine | Calc'd 459.0, found 459 |
| 1-91 | 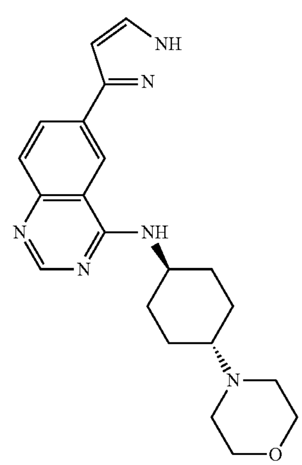 [SMILES: N=C(/C=C\N)c1ccc2ncnc(N[C@H]3CC[C@H](N4CCOCC4)CC3)c2c1] | N-[trans-4-(morpholin-4-yl)cyclohexyl]-6-(1H-pyrazol-3-yl)quinazolin-4-amine | Calc'd 379.0, found 379 |

TABLE 4-continued
| Example # | Structure | Chemical Name | MS (M + 1) |
|---|---|---|---|
| 1-92 | 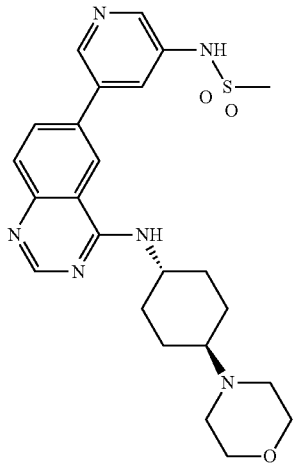 | N-[5-(4-{[trans-4-(morpholin-4-yl)cyclohexyl]amino}quinazolin-6-yl)pyridin-3-yl]methanesulfonamide | Calc'd 483.0, found 483 |
| 1-93 | 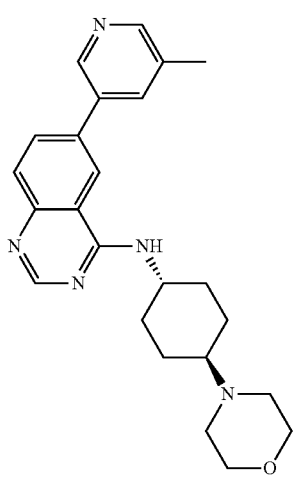 [SMILES: Cc1cncc(-c2ccc3ncnc(N[C@H]4CC[C@H](N5CCOCC5)CC4)c3c2)c1] | 6-(5-methylpyridin-3-yl)-N-[trans-4-(morpholin-4-yl)cyclohexyl]quinazolin-4-amine | Calc'd 404.0, found 404 |
| 1-94 | 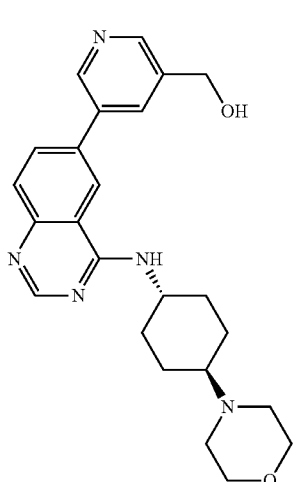 | [5-(4-{[trans-4-(morpholin-4-yl)cyclohexyl]amino}quinazolin-6-yl)pyridin-3-yl]methanol | Calc'd 420.0, found 420 |

TABLE 4-continued
| Example # | Structure | Chemical Name | MS (M + 1) |
|---|---|---|---|
| 1-95 | 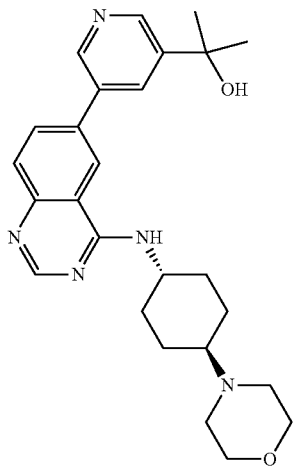 | 2-[5-(4-{[trans-4-(morpholin-4-yl)cyclohexyl]amino}quinazolin-6-yl)pyridin-3-yl]propan-2-ol | Calc'd 448.0, found 448 |
| 1-96 | 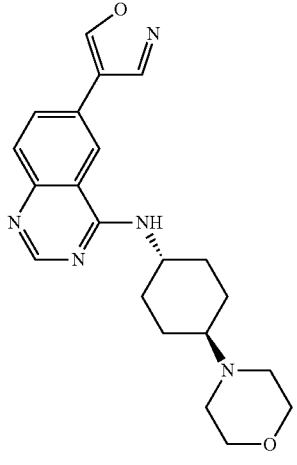 | 6-(isoxazol-4-yl)-N-[trans-4-(morpholin-4-yl)cyclohexyl]quinazolin-4-amine | Calc'd 380.0, found 380 |
| 1-97 | 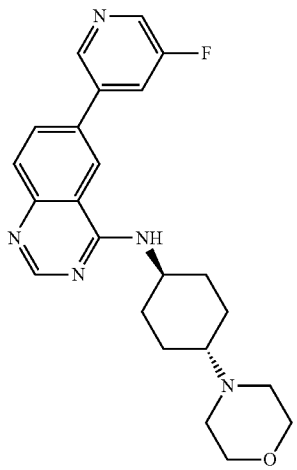 [SMILES: Fc1cncc(-c2ccc3ncnc(N[C@H]4CC[C@H](N5CCOCC5)CC4)c3c2)c1] | 6-(5-fluoropyridin-3-yl)-N-[trans-4-(morpholin-4-yl)cyclohexyl]quinazolin-4-amine | Calc'd 408.0, found 408 |

TABLE 4-continued
| Example # | Structure | Chemical Name | MS (M + 1) |
|---|---|---|---|
| 1-98 | 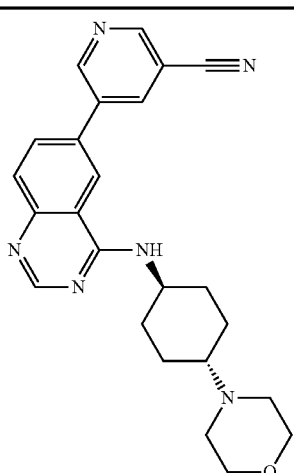 | 5-(4-{[trans-4-(morpholin-4-yl)cyclohexyl]amino}quinazolin-6-yl)pyridine-3-carbonitrile | Calc'd 415.0, found 415 |
| 1-99 | 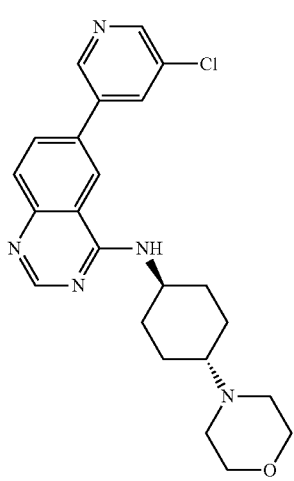 [SMILES: Clc1cncc(-c2ccc3ncnc(N[C@H]4CC[C@H](N5CCOCC5)CC4)c3c2)c1] | 6-(5-chloropyridin-3-yl)-N-[trans-4-(morpholin-4-yl)cyclohexyl]quinazolin-4-amine | Calc'd 424.0, found 424 |
| 1-100 | 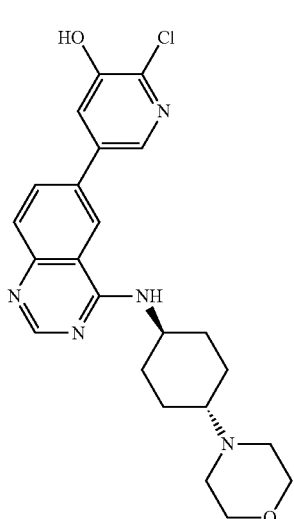 | 2-chloro-5-(4-{[trans-4-(morpholin-4-yl)cyclohexyl]amino}quinazolin-6-yl)pyridin-3- | Calc'd 440.0, found 440 |

EXAMPLE 2-1

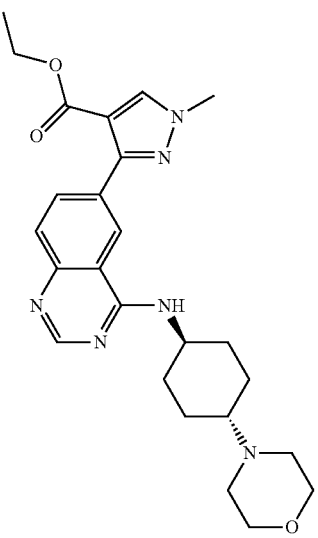 [SMILES: CCOC(=O)c1cn(C)nc1-c1ccc2ncnc(N[C@H]3CC[C@H](N4CCOCC4)CC3)c2c1]

Ethyl 1-methyl-3-(4-(((trans)-4-morpholinocyclohexyl)amino)quinazolin-6-yl)-1H-pyrazole-4-carboxylate (Scheme 1)

(4-(((Trans)-4-morpholinocyclohexyl)amino)quinazolin-6-yl)boronic acid (30 mg, 0.084 mmol) was dissolved in EtOH (1 mL) and added to a vial containing ethyl 3-bromo-1-methyl-1H-pyrazole-4-carboxylate (29.0 mg, 0.126 mmol) and Si-DPP-Pd (64.8 mg, 0.017 mmol). Potassium carbonate (1M in water, 0.084 ml, 0.168 mmol) was added, the vial was sealed and the resulting mixture was then heated to 125° C. for 10 minutes under microwave irradiation. The mixture was filtered and purified by mass triggered reverse phase HPLC (ACN/water with 0.1% TFA modifier) to afford the title product as a TFA salt. MS: 465 (M+1). $^1$H NMR (DMSO-$d_6$, 600 MHz) δ 9.79 (s, 1H), 8.89 (s, 1H), 8.75 (s, 1H), 8.48 (s, 1H), 8.25 (d, J=8.69 Hz, 1H), 7.81 (d, J=8.67 Hz, 1H), 4.39 (br s, 1H), 4.14 (q, J=7.10 Hz, 2H), 4.02-4.00 (m, 2H), 3.95 (s, 3H), 3.71-3.69 (m, 2H), 3.44-3.39 (br s, 1H), 2.52-2.50 (m, 4H), 2.20-2.18 (m, 2H), 2.10-2.08 (m, 2H), 1.64-1.58 (m, 4H), 1.16 (t, J=7.10 Hz, 3H).

The following examples in Table 5 were prepared in an analogous manner of those described in Example 2-1 and general scheme 1.

TABLE 5

| Example # | Structure | Chemical Name | MS (M + 1) |
|---|---|---|---|
| 2-2 | 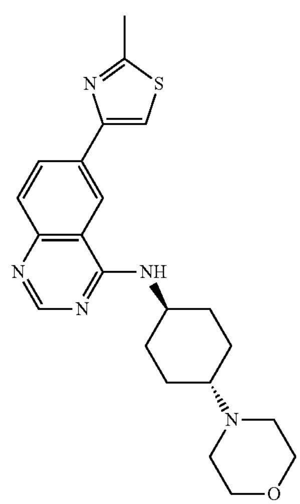 [SMILES: Cc1nc(-c2ccc3ncnc(N[C@H]4CC[C@H](N5CCOCC5)CC4)c3c2)cs1] | 6-(2-methyl-1,3-thiazol-4-yl)-N-(trans-4-morpholin-4-ylcyclohexyl)quinazolin-4-amine | Calc'd 410.0, found 410 |

TABLE 5-continued

| Example # | Structure | Chemical Name | MS (M + 1) |
|---|---|---|---|
| 2-3 | 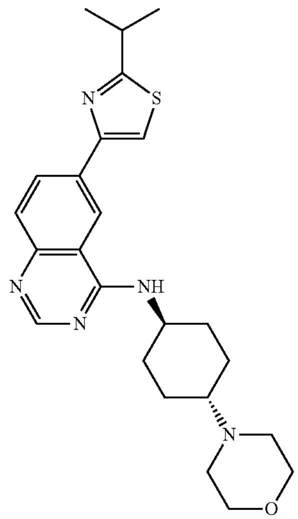 [SMILES: CC(C)c1nc(-c2ccc3ncnc(N[C@H]4CC[C@H](N5CCOCC5)CC4)c3c2)cs1] | 6-[2-(1-methylethyl)-1,3-thiazol-4-yl]-N-(trans-4-morpholin-4-ylcyclohexyl)quinazolin-4-amine | Calc'd 438.0, found 438 |
| 2-4 | 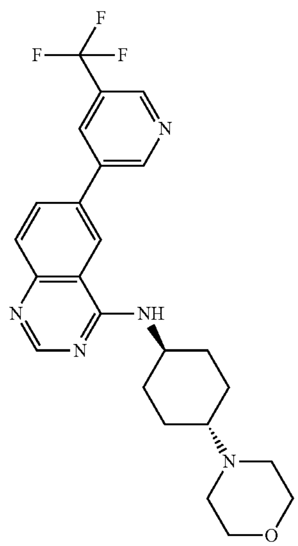 [SMILES: FC(F)(F)c1cncc(-c2ccc3ncnc(N[C@H]4CC[C@H](N5CCOCC5)CC4)c3c2)c1] | N-(trans-4-morpholin-4-ylcyclohexyl)-6-[5-(trifluoromethyl)pyridin-3-yl]quinazolin-4-amine | Calc'd 458.0, found 458 |
| 2-5 | 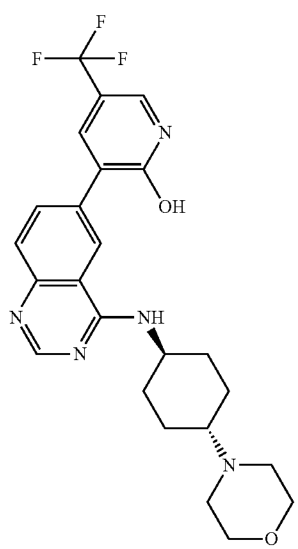 [SMILES: Oc1ncc(C(F)(F)F)cc1-c1ccc2ncnc(N[C@H]3CC[C@H](N4CCOCC4)CC3)c2c1] | 3-{4-[(trans-4-morpholin-4-ylcyclohexyl)amino]quinazolin-6-yl}-5-(trifluoromethyl)pyridin-2-ol | Calc'd 474.0, found 474 |

TABLE 5-continued
| Example # | Structure | Chemical Name | MS (M + 1) |
|---|---|---|---|
| 2-6 | 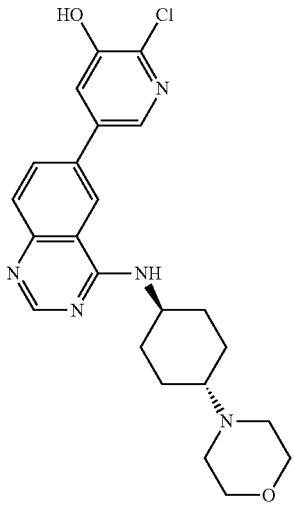 [SMILES: Oc1cc(-c2ccc3ncnc(N[C@H]4CC[C@H](N5CCOCC5)CC4)c3c2)cnc1Cl] | 2-chloro-5-{4-[(trans-4-morpholin-4-ylcyclohexyl)amino]quinazolin-6-yl}pyridin-3-ol | Calc'd 440.0, found 440 |
| 2-7 | 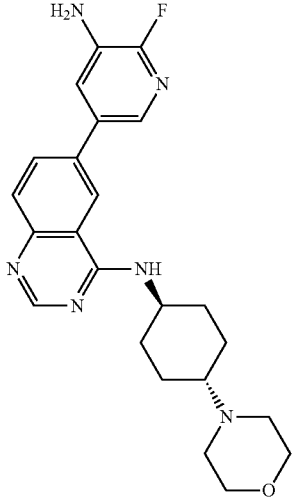 [SMILES: Nc1cc(-c2ccc3ncnc(N[C@H]4CC[C@H](N5CCOCC5)CC4)c3c2)cnc1F] | 6-(5-amino-6-fluoropyridin-3-yl)-N-(trans-4-morpholin-4-ylcyclohexyl)quinazolin-4-amine | Calc'd 423.0, found 423 |
| 2-8 | 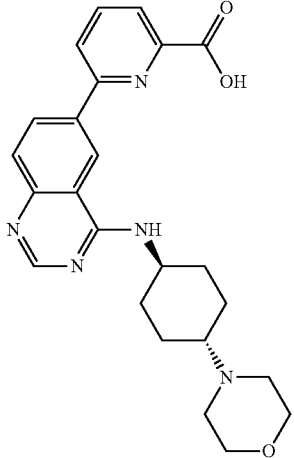 [SMILES: O=C(O)c1cccc(-c2ccc3ncnc(N[C@H]4CC[C@H](N5CCOCC5)CC4)c3c2)n1] | 6-{4-[(trans-4-morpholin-4-ylcyclohexyl)amino]quinazolin-6-yl}pyridine-2-carboxylic acid | Calc'd 434.0, found 434 |

TABLE 5-continued

| Example # | Structure | Chemical Name | MS (M + 1) |
|---|---|---|---|
| 2-9 | 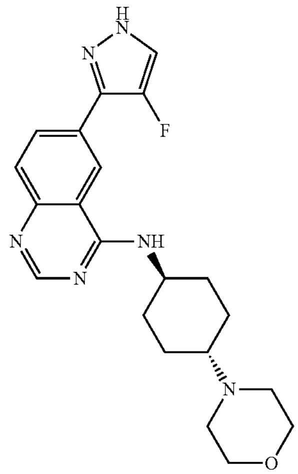 [SMILES: Fc1c[nH]nc1-c1ccc2ncnc(N[C@H]3CC[C@H](N4CCOCC4)CC3)c2c1] | 6-(4-fluoro-1H-pyrazol-3-yl)-N-(trans-4-morpholin-4-ylcyclohexyl)quinazolin-4-amine | Calc'd 397.0, found 397 |
| 2-10 | 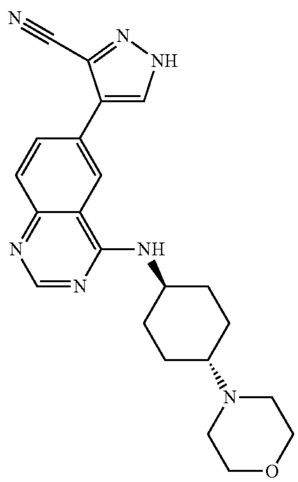 [SMILES: N#Cc1n[nH]cc1-c1ccc2ncnc(N[C@H]3CC[C@H](N4CCOCC4)CC3)c2c1] | 4-{4-[(trans-4-morpholin-4-ylcyclohexyl)amino]quinazolin-6-yl}-1H-pyrazole-3-carbonitrile | Calc'd 404.0, found 404 |
| 2-11 | 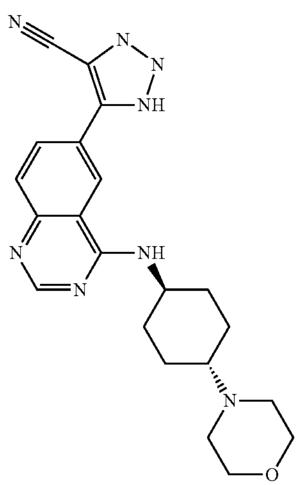 [SMILES: N#CC1=C(c2ccc3ncnc(N[C@H]4CC[C@H](N5CCOCC5)CC4)c3c2)NNN1] | 5-{4-[(trans-4-morpholin-4-ylcyclohexyl)amino]quinazolin-6-yl}-1H-1,2,3-triazole-4-carbonitrile | Calc'd 405.0, found 405 |

TABLE 5-continued

| Example # | Structure | Chemical Name | MS (M + 1) |
|---|---|---|---|
| 2-12 | 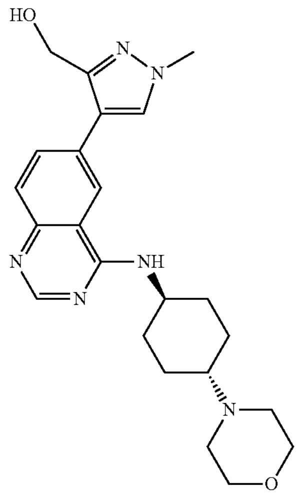 [SMILES: Cn1cc(-c2ccc3ncnc(N[C@H]4CC[C@H](N5CCOCC5)CC4)c3c2)c(CO)n1] | (1-methyl-4-{4-[(trans-4-morpholin-4-ylcyclohexyl)amino]quinazolin-6-yl}-1H-pyrazol-3-yl)methanol | Calc'd 423.0, found 423 |
| 2-13 | 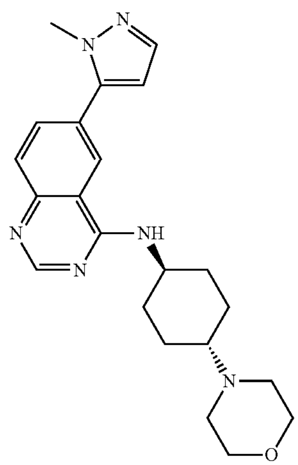 [SMILES: Cn1nccc1-c1ccc2ncnc(N[C@H]3CC[C@H](N4CCOCC4)CC3)c2c1] | 6-(1-methyl-1H-pyrazol-5-yl)-N-(trans-4-morpholin-4-ylcyclohexyl)quinazolin-4-amine | Calc'd 393.0, found 393 |
| 2-14 | 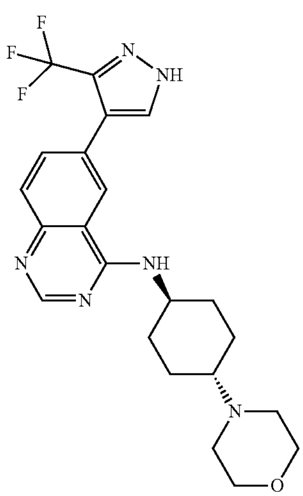 [SMILES: FC(F)(F)c1n[nH]cc1-c1ccc2ncnc(N[C@H]3CC[C@H](N4CCOCC4)CC3)c2c1] | N-(trans-4-morpholin-4-ylcyclohexyl)-6-[3-(trifluoromethyl)-1H-pyrazol-4-yl]quinazolin-4-amine | Calc'd 447.0, found 447 |

TABLE 5-continued

| Example # | Structure | Chemical Name | MS (M + 1) |
|---|---|---|---|
| 2-15 | 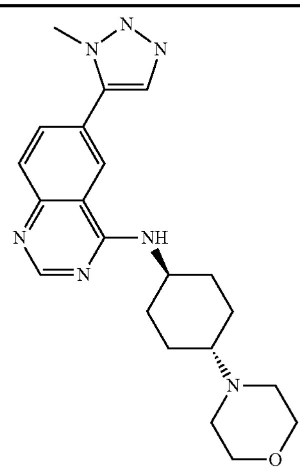 | 6-(1-methyl-1H-1,2,3-triazol-5-yl)-N-(trans-4-morpholin-4-ylcyclohexyl)quinazolin-4-amine | Calc'd 394.0, found 394 |
| 2-16 | 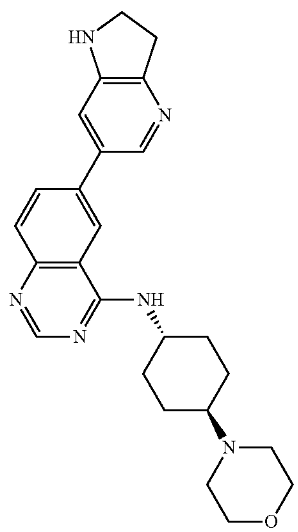 [SMILES: c1nc(N[C@H]2CC[C@H](N3CCOCC3)CC2)c2cc(-c3cnc4c(c3)NCC4)ccc2n1] | 6-(2,3-dihydro-1H-pyrrolo[3,2-b]pyridin-6-yl)-N-[trans-4-(morpholin-4-yl)cyclohexyl]quinazolin-4-amine | Calc'd 431.0, found 431 |
| 2-17 | 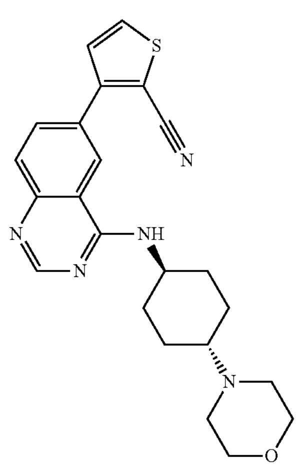 [SMILES: N#Cc1sccc1-c1ccc2ncnc(N[C@H]3CC[C@H](N4CCOCC4)CC3)c2c1] | 3-(4-{[trans-4-(morpholin-4-yl)cyclohexyl]amino}quinazolin-6-yl)thiophene-2-carbonitrile | Calc'd 420.0, found 420 |

TABLE 5-continued

| Example # | Structure | Chemical Name | MS (M + 1) |
|---|---|---|---|
| 2-18 | 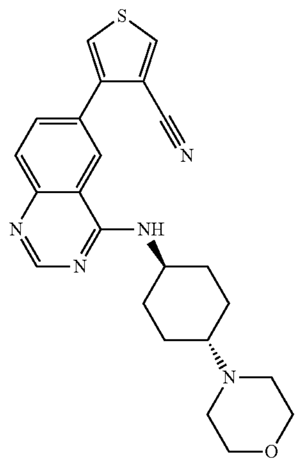 [SMILES: N#Cc1cscc1-c1ccc2ncnc(N[C@H]3CC[C@H](N4CCOCC4)CC3)c2c1] | 4-(4-{[trans-4-(morpholin-4-yl)cyclohexyl]amino}quinazolin-6-yl)thiophene-3-carbonitrile | Calc'd 420.0, found 420 |
| 2-19 | 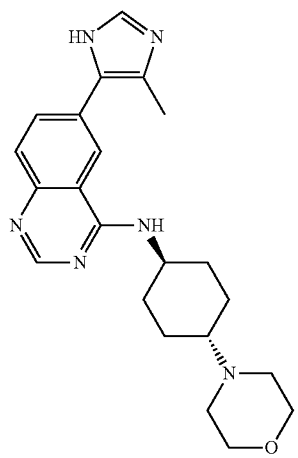 [SMILES: Cc1nc[nH]c1-c1ccc2ncnc(N[C@H]3CC[C@H](N4CCOCC4)CC3)c2c1] | 6-(4-methyl-1H-imidazol-5-yl)-N-[trans-4-(morpholin-4-yl)cyclohexyl]quinazolin-4-amine | Calc'd 393.0, found 393 |
| 2-20 | 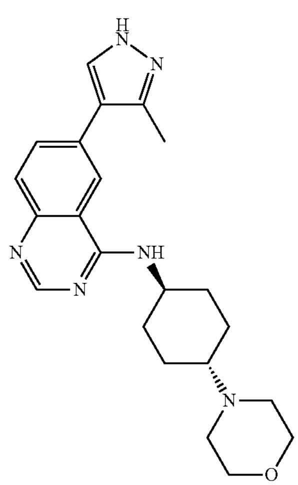 [SMILES: Cc1n[nH]cc1-c1ccc2ncnc(N[C@H]3CC[C@H](N4CCOCC4)CC3)c2c1] | 6-(3-methyl-1H-pyrazol-4-yl)-N-[trans-4-(morpholin-4-yl)cyclohexyl]quinazolin-4-amine | Calc'd 393.0, found 393 |

TABLE 5-continued

| Example # | Chemical Name | MS (M + 1) |
|---|---|---|
| 2-21 | 6-(1,5-dimethyl-1H-pyrazol-4-yl)-N-[trans-4-(morpholin-4-yl)cyclohexyl]quinazolin-4-amine | Calc'd 407.0, found 407 |
| 2-22 | 6-(4-methyl-1H-imidazol-2-yl)-N-[trans-4-(morpholin-4-yl)cyclohexyl]quinazolin-4-amine | Calc'd 393.0, found 393 |
| 2-23 | 6-(1,4-dimethyl-1H-imidazol-2-yl)-N-[trans-4-(morpholin-4-yl)cyclohexyl]quinazolin-4-amine | Calc'd 407.0, found 407 |

TABLE 5-continued

| Example # | Structure | Chemical Name | MS (M + 1) |
|---|---|---|---|
| 2-24 | 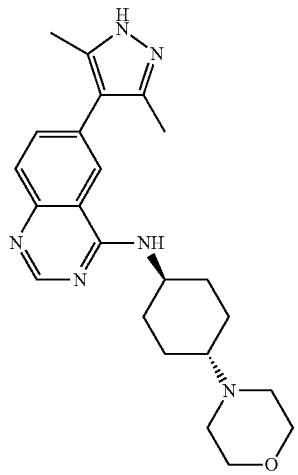 [SMILES: Cc1n[nH]c(C)c1-c1ccc2ncnc(N[C@H]3CC[C@H](N4CCOCC4)CC3)c2c1] | 6-(3,5-dimethyl-1H-pyrazol-4-yl)-N-[trans-4-(morpholin-4-yl)cyclohexyl]quinazolin-4-amine | Calc'd 407.0, found 407 |
| 2-25 | 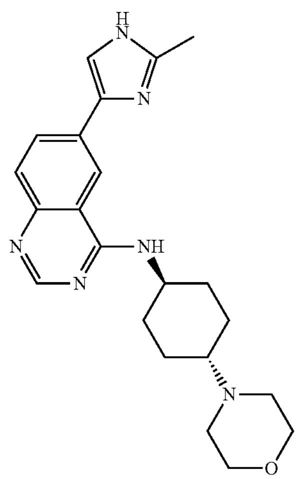 [SMILES: Cc1nc(-c2ccc3ncnc(N[C@H]4CC[C@H](N5CCOCC5)CC4)c3c2)c[nH]1] | 6-(2-methyl-1H-imidazol-4-yl)-N-[trans-4-(morpholin-4-yl)cyclohexyl]quinazolin-4-amine | Calc'd 393.0, found 393 |
| 2-26 | 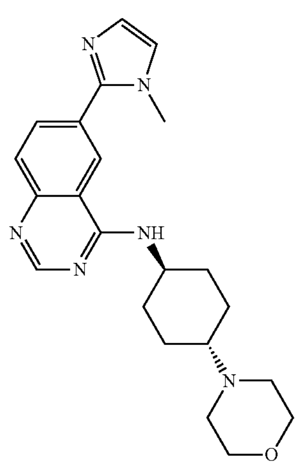 [SMILES: Cn1ccnc1-c1ccc2ncnc(N[C@H]3CC[C@H](N4CCOCC4)CC3)c2c1] | 6-(1-methyl-1H-imidazol-2-yl)-N-[trans-4-(morpholin-4-yl)cyclohexyl]quinazolin-4-amine | Calc'd 393.0, found 393 |

TABLE 5-continued

| Example # | Structure | Chemical Name | MS (M + 1) |
|---|---|---|---|
| 2-27 | 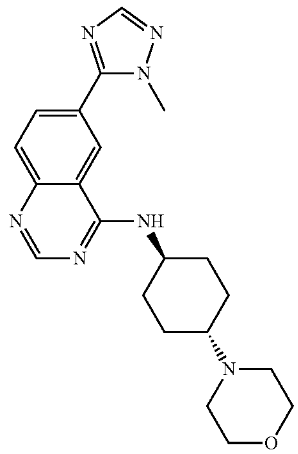 [SMILES: Cn1ncnc1-c1ccc2ncnc(N[C@H]3CC[C@H](N4CCOCC4)CC3)c2c1] | 6-(1-methyl-1H-1,2,4-triazol-5-yl)-N-[trans-4-(morpholin-4-yl)cyclohexyl]quinazolin-4-amine | Calc'd 394.0, found 394 |
| 2-28 | 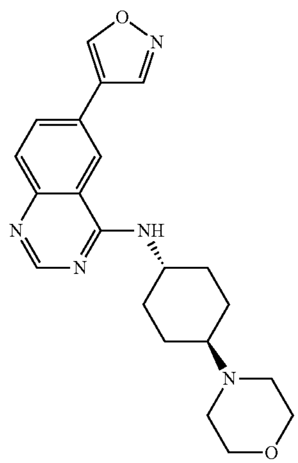 [SMILES: c1nc(N[C@H]2CC[C@H](N3CCOCC3)CC2)c2cc(-c3cnoc3)ccc2n1] | 6-(isoxazol-4-yl)-N-[trans-4-(morpholin-4-yl)cyclohexyl]quinazolin-4-amine | Calc'd 380.0, found 380 |
| 2-29 | 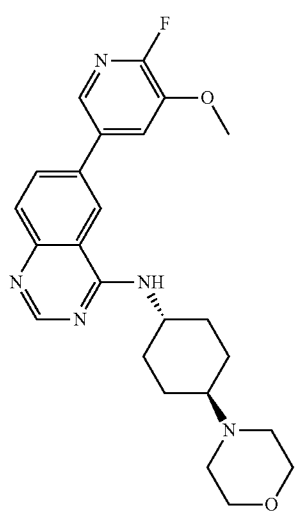 [SMILES: COc1cc(-c2ccc3ncnc(N[C@H]4CC[C@H](N5CCOCC5)CC4)c3c2)cnc1F] | 6-(6-fluoro-5-methoxypyridin-3-yl)-N-[trans-4-(morpholin-4-yl)cyclohexyl]quinazolin-4-amine | Calc'd 438.0, found 438 |

TABLE 5-continued
| Example # | Structure | Chemical Name | MS (M + 1) |
|---|---|---|---|
| 2-30 | 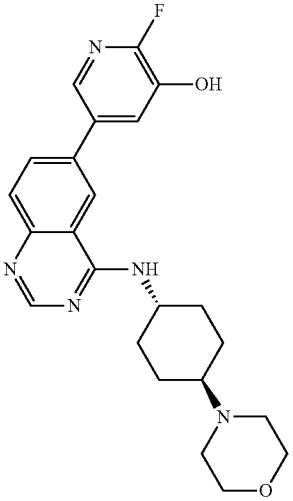 [SMILES: Oc1cc(-c2ccc3ncnc(N[C@H]4CC[C@H](N5CCOCC5)CC4)c3c2)cnc1F] | 2-fluoro-5-(4-{[trans-4-(morpholin-4-yl)cyclohexyl]amino}quinazolin-6-yl)pyridin-3-ol | Calc'd 424.0, found 424 |
| 2-31 | 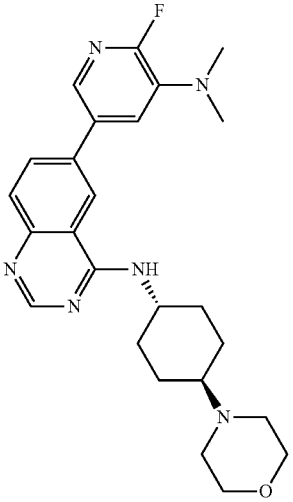 [SMILES: CN(C)c1cc(-c2ccc3ncnc(N[C@H]4CC[C@H](N5CCOCC5)CC4)c3c2)cnc1F] | 6-[5-(dimethylamino)-6-fluoropyridin-3-yl]-N-[trans-4-(morpholin-4-yl)cyclohexyl]quinazolin-4-amine | Calc'd 451.0, found 451 |
| 2-32 | 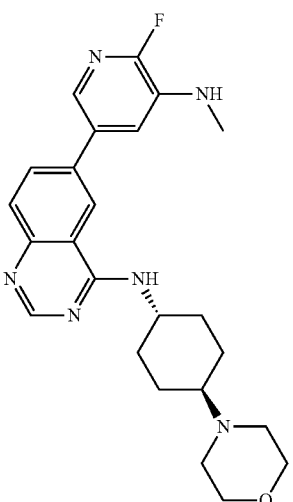 | 6-[6-fluoro-5-(methylamino)pyridin-3-yl]-N-[trans-4-(morpholin-4-yl)cyclohexyl]quinazolin-4-amine | Calc'd 437.0, found 437 |

TABLE 5-continued

| Example # | Structure | Chemical Name | MS (M + 1) |
|---|---|---|---|
| 2-33 | 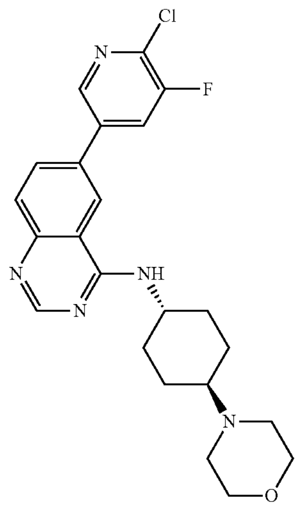 [SMILES: Fc1cc(-c2ccc3ncnc(N[C@H]4CC[C@H](N5CCOCC5)CC4)c3c2)cnc1Cl] | 6-(6-chloro-5-fluoropyridin-3-yl)-N-[trans-4-(morpholin-4-yl)cyclohexyl]quinazolin-4-amine | Calc'd 442.0, found 442 |
| 2-34 | 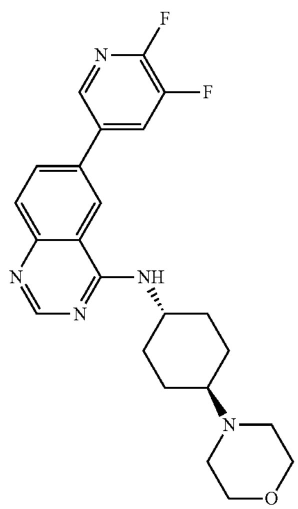 [SMILES: Fc1cc(-c2ccc3ncnc(N[C@H]4CC[C@H](N5CCOCC5)CC4)c3c2)cnc1F] | 6-(5,6-difluoropyridin-3-yl)-N-[trans-4-(morpholin-4-yl)cyclohexyl]quinazolin-4-amine | Calc'd 426.0, found 426 |
| 2-35 | 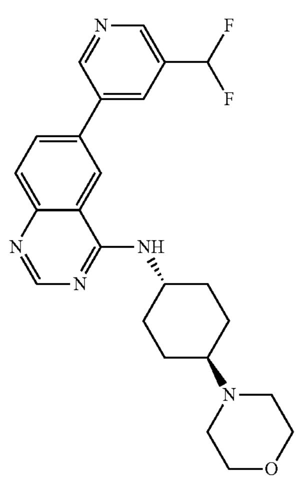 [SMILES: FC(F)c1cncc(-c2ccc3ncnc(N[C@H]4CC[C@H](N5CCOCC5)CC4)c3c2)c1] | 6-[5-(difluoromethyl)pyridin-3-yl]-N-[trans-4-(morpholin-4-yl)cyclohexyl]quinazolin-4-amine | Calc'd 440.0, found 440 |

TABLE 5-continued

| Example # | Structure | Chemical Name | MS (M + 1) |
|---|---|---|---|
| 2-36 | 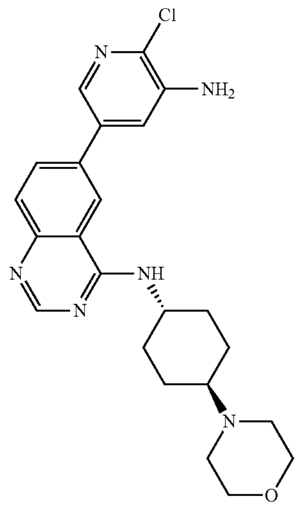 [SMILES: Nc1cc(-c2ccc3ncnc(N[C@H]4CC[C@H](N5CCOCC5)CC4)c3c2)cnc1Cl] | 6-(5-amino-6-chloropyridin-3-yl)-N-[trans-4-(morpholin-4-yl)cyclohexyl]quinazolin-4-amine | Calc'd 439.0, found 439 |

EXAMPLE 3-1

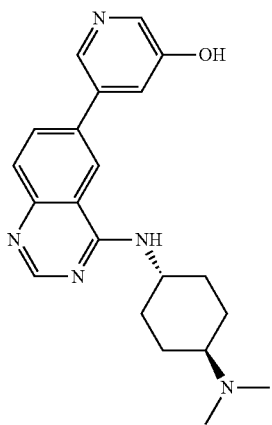 [SMILES: CN(C)[C@H]1CC[C@H](Nc2ncnc3ccc(-c4cncc(O)c4)cc23)CC1]

5-(4-(((Trans)-4-(dimethylamino)cyclohexyl)amino)quinazolin-6-yl)pyridin-3-ol (Scheme 2)

Step 1: Trans-N-(6-{5-[(4-methoxybenzyl)oxy]pyridin-3-yl}quinazolin-4-yl)-N,N-dimethylcyclohexane-1,4-diamine Into a 10-mL microwave vial containing a solution of (trans)-N1-(6-bromoquinazolin-4-yl)N4,N4-dimethylcyclohexane-1,4-diamine (50 mg, 0.14 mmol) in dioxane (4 mL) and water (1 mL) was added (5-((4-methoxybenzyl)oxy)pyridin-3-yl)boronic acid (54 mg, 0.21 mmol) and cesium carbonate (97 mg, 0.3 mmol) and the reaction was degassed with nitrogen for 30 min. Then was added 1,1'-bis(diphenylphosphino)ferrocene]dichloropalladium(II) (10 mg, 0.01 mmol) and the reaction was subjected to microwave irradiation at 130° C. for 1 h. The reaction mixture was diluted with ethyl acetate, washed with water and then brine, and then dried over anhydrous $Na_2SO_4$ and filtered. The solution was concentrated under reduced pressure and the residue thus obtained was purified by reverse phase preparative HPLC (MeOH/water with 0.1% formic acid modifier) to furnish (trans)-N1-(6-(5-((4-methoxybenzyl)oxy)pyridin-3-yl)quinazolin-4-yl)-N4,N4-dimethylcyclohexane-1,4-diamine. MS: 484 (M+1).

Step 2: 5-(4-(((Trans)-4-(dimethylamino)cyclohexyl)amino)quinazolin-6-yl)pyridin-3-ol Into a 10-mL round bottom flask containing a solution of (trans)-N1-(6-(5-((4-methoxybenzyl)oxy)pyridin-3-yl)quinazolin-4-yl)-N4,N4-dimethylcyclohexane-1,4-diamine (20 mg, 0.04 mmol) in dichloromethane (2 mL) was added trifluoroacetic acid (1 mL) at 0° C. and the mixture was allowed to stir at rt for 3 h. The reaction mixture was concentrated under reduce pressure and purified by reverse phase preparative HPLC (MeOH/water with 0.1% TFA modifier) to furnish the title compound. MS: 364 (M+1). $^1$H NMR (400 MHz, dmso) δ 8.65 (d, J=1.6 Hz, 1H), 8.53 (d, J=1.6 Hz, 1H), 8.46 (s, 1H), 8.18 (d, J=2.5 Hz, 1H), 8.13-8.11 (m, 1H), 8.07 (dd, J=8.6 Hz, 1.8 Hz, 1H), 7.74 (d, J=8.6 Hz, 1H), 7.58 (brs, 1H), 4.19-4.12 (m, 1H), 3.81-3.8 (m, 1H), 2.25 (s, 6H), 2.08-2.05 (m, 2H), 1.92-1.89 (m, 2H), 1.5-1.43 (m, 4H).

EXAMPLE 4-1

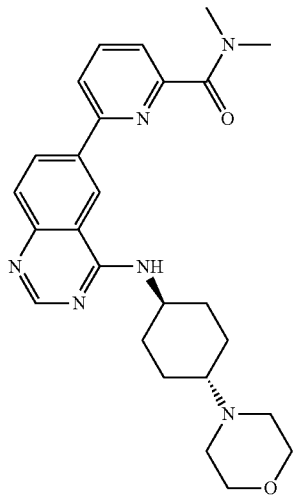 [SMILES: CN(C)C(=O)c1cccc(-c2ccc3ncnc(N[C@H]4CC[C@H](N5CCOCC5)CC4)c3c2)n1]

N,N-Dimethyl-6-(4-(((trans)-4-morpholinocyclo-hexyl)amino)quinazolin-6-yl)picolinamide (Scheme 3)

6-(4-(((trans)-4-morpholinocyclohexyl)amino)quinazolin-6-yl)picolinic acid (25 mg, 0.058 mmol), dimethylamine (2M in THF, 100 µl, 0.200 mmol), DIEA (30.2 µl, 0.173 mmol), and DMF (500 µl) were added to a 2-dram vial. The vial was chilled to 0° C. before T3P (86 µl, 0.144 mmol) was added. The reaction mixture was allowed to warm to rt and then stirred for 16 h, after which time the mixture was filtered and purified by mass triggered reverse phase HPLC (ACN/water with 0.1% NH$_4$OH modifier) to afford the title compound. MS: 461 (M+1). $^1$H NMR (600 MHz, dmso): δ 8.88 (s, 1H), 8.47-8.45 (m, 2H), 8.19-8.18 (m, 1H), 8.14 (d, J=7.6 Hz, 1H), 8.06 (t, J=7.8 Hz, 1H), 7.73 (d, J=8.7 Hz, 1H), 7.52 (d, J=7.6 Hz, 1H), 4.16 (br s, 1H), 3.55 (br s, 4H), 3.03 (s, 3H), 3.00 (s, 3H), 2.46-2.45 (m, 4H), 2.24-2.21 (m, 1H), 2.06 (br s, 2H), 1.90 (br s, 2H), 1.46-1.44 (m, 2H), 1.35 (br s, 2H).

EXAMPLE 5-1

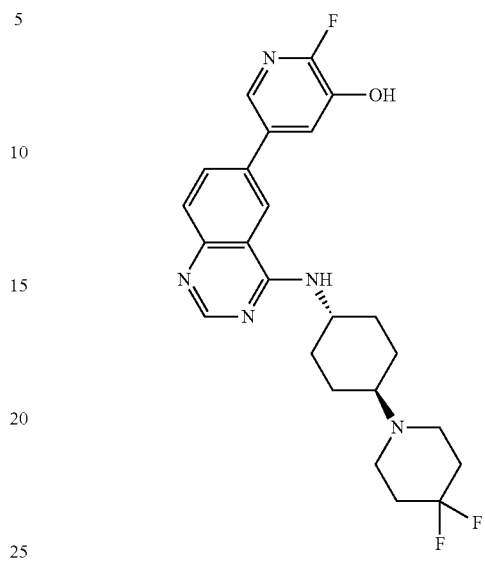

5-(4-{[Trans-4-(4,4-difluoropiperidin-1-yl)cyclo-hexyl]amino}quinazolin-6-yl)-2-fluoropyridin-3-ol (Scheme 4)

A 50 mL round bottom flask was charged with 4-{[6-(6-fluoro-5-hydroxypyridin-3-yl)quinazolin-4-yl]amino}cyclohexanone (0.045 g, 0.128 mmol), DMA (2.00 mL), acetic acid (0.015 mL, 0.255 mmol) and 4,4-difluoropiperidine hydrochloride (0.060 g, 0.383 mmol). The contents of the flask were allowed to stir at room temperature for 90 minutes. Sodium triacetoxyborohydride (0.081 g, 0.383 mmol) was added to the reaction mixture which was stirred an additional 16 hours. The reaction mixture was filtered and purified by mass triggered reverse phase HPLC (ACN/water with 0.1% TFA modifier) to afford a mixture of the title compound and its cis isomer. The mixture was further purified by chiral SFC (Chiralpak AD-H column, 30%/70% methanol+0.25% dimethyl ethyl amine/CO$_2$) to afford title compound (slower eluting). MS: 458 (M+1). $^1$H NMR (600 MHz, DMSO-d$_6$): δ 8.55 (s, 1H); 8.42 (s, 1H); 8.03 (d, J=7.6 Hz, 1H); 7.98 (d, J=9.8 Hz, 2H); 7.72-7.68 (m, 2H); 4.17-4.09 (m, 1H); 2.61-2.56 (m, 4H); 2.50-2.41 (m, 1H); 2.05-2.00 (m, 2H); 1.95-1.85 (m, 4H); 1.85-1.75 (m, 2H); 1.46-1.34 (m, 4H).

The following examples in Table 6 were prepared in an analogous manner of those described in Example 5-1 and general scheme 4.

TABLE 6

| Example # | Structure | Chemical Name | MS (M + 1) |
|---|---|---|---|
| 5-2 | 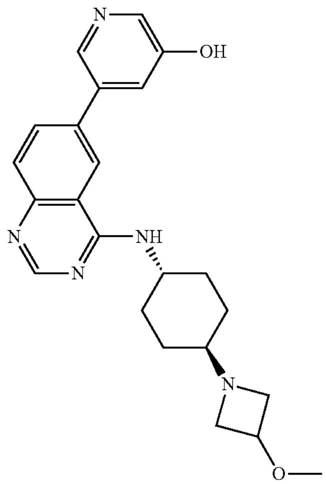 [SMILES: COC1CN([C@H]2CC[C@H](Nc3ncnc4ccc(-c5cncc(O)c5)cc34)CC2)C1] | 5-(4-{[trans-4-(3-methoxyazetidin-1-yl)cyclohexyl]amino}quinazolin-6-yl)pyridin-3-ol | Calc'd 406.0, found 406 |
| 5-3 | 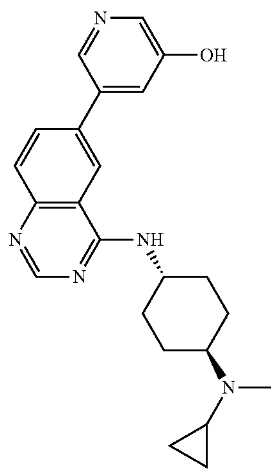 [SMILES: CN(C1CC1)[C@H]1CC[C@H](Nc2ncnc3ccc(-c4cncc(O)c4)cc23)CC1] | 5-[4-({trans-4-[cyclopropyl(methyl)amino]cyclohexyl}amino)quinazolin-6-yl]pyridin-3-ol | Calc'd 390.0, found 390 |
| 5-4 | 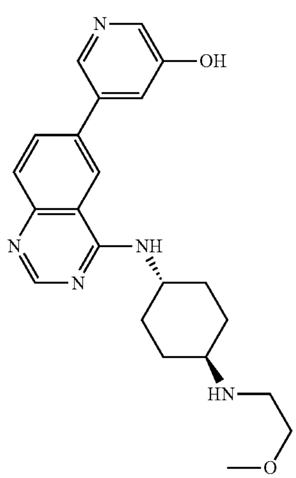 [SMILES: COCCN[C@H]1CC[C@H](Nc2ncnc3ccc(-c4cncc(O)c4)cc23)CC1] | 5-[4-({trans-4-[(2-methoxyethyl)amino]cyclohexyl}amino)quinazolin-6-yl]pyridin-3-ol | Calc'd 394.0, found 394 |

TABLE 6-continued

| Example # | Chemical Name | MS (M + 1) |
|---|---|---|
| 5-5 | 5-(4-{[trans-4-(4-methylpiperazin-1-yl)cyclohexyl]amino}quinazolin-6-yl)pyridin-3-ol | Calc'd 419.0, found 419 |
| 5-6 | 5-[4-({trans-4-[(2R,6S)-2,6-dimethylmorpholin-4-yl]cyclohexyl}amino)quinazolin-6-yl]pyridin-3-ol | Calc'd 434.0, found 434 |
| 5-7 | 6-[5-(methylamino)pyridin-3-yl]-N-{trans-4-[4-(methylsulfonyl)piperazin-1-yl]cyclohexyl}quinazolin-4-amine | Calc'd 496.0, found 496 |

TABLE 6-continued

| Example # | Structure | Chemical Name | MS (M + 1) |
|---|---|---|---|
| 5-8 | 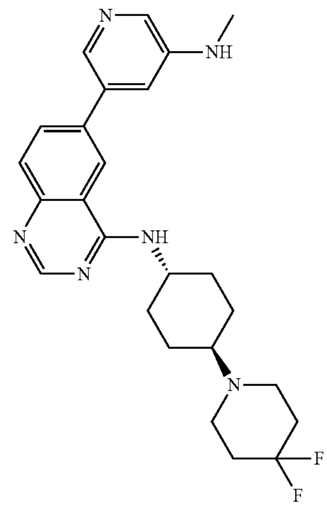 [SMILES: CNc1cncc(-c2ccc3ncnc(N[C@H]4CC[C@H](N5CCC(F)(F)CC5)CC4)c3c2)c1] | N-[trans-4-(4,4-difluoropiperidin-1-yl)cyclohexyl]-6-[5-(methylamino)pyridin-3-yl]quinazolin-4-amine | Calc'd 453.0, found 453 |
| 5-9 | 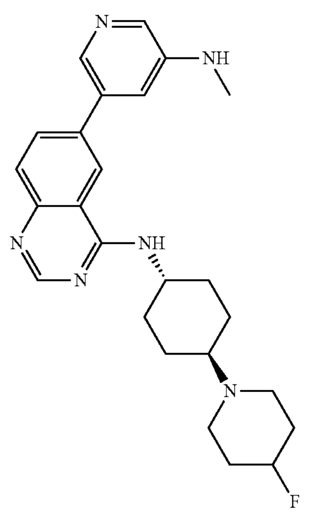 [SMILES: CNc1cncc(-c2ccc3ncnc(N[C@H]4CC[C@H](N5CCC(F)CC5)CC4)c3c2)c1] | N-[trans-4-(4-fluoropiperidin-1-yl)cyclohexyl]-6-[5-(methylamino)pyridin-3-yl]quinazolin-4-amine | Calc'd 435.0, found 435 |
| 5-10 | 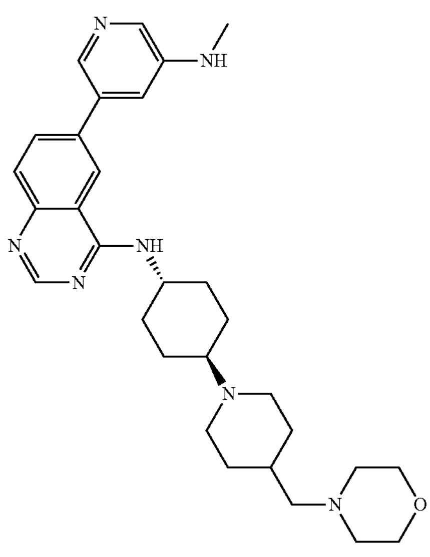 [SMILES: CNc1cncc(-c2ccc3ncnc(N[C@H]4CC[C@H](N5CCC(CN6CCOCC6)CC5)CC4)c3c2)c1] | 6-[5-(methylamino)pyridin-3-yl]-N-{trans-4-[4-(morpholin-4-ylmethyl)piperidin-1-yl]cyclohexyl}quinazolin-4-amine | Calc'd 516.0, found 516 |

TABLE 6-continued
| Example # | Structure | Chemical Name | MS (M + 1) |
|---|---|---|---|
| 5-11 | 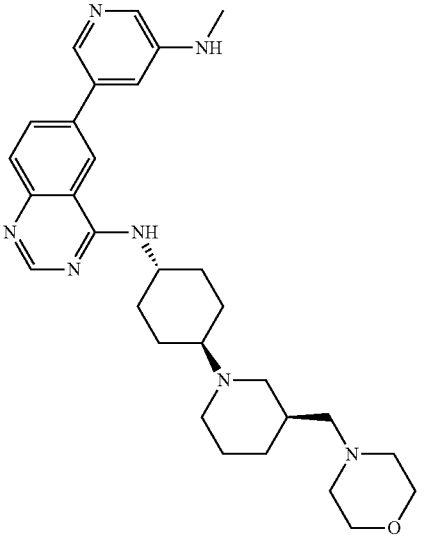 [SMILES: CNc1cncc(-c2ccc3ncnc(N[C@H]4CC[C@H](N5CCC[C@H](CN6CCOCC6)C5)CC4)c3c2)c1] | 6-[5-(methylamino)pyridin-3-yl]-N-{trans-4-[(3R)-3-(morpholin-4-ylmethyl)piperidin-1-yl]cyclohexyl}quinazolin-4-amine | Calc'd 516.0, found 516 |
| 5-12 | 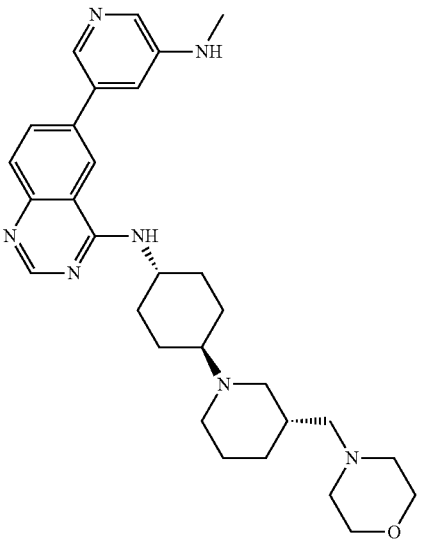 [SMILES: CNc1cncc(-c2ccc3ncnc(N[C@H]4CC[C@H](N5CCC[C@@H](CN6CCOCC6)C5)CC4)c3c2)c1] | 6-[5-(methylamino)pyridin-3-yl]-N-{trans-4-[(3S)-3-(morpholin-4-ylmethyl)piperidin-1-yl]cyclohexyl}quinazolin-4-amine | Calc'd 516.0, found 516 |

TABLE 6-continued
| Example # | Structure | Chemical Name | MS (M + 1) |
|---|---|---|---|
| 5-13 | 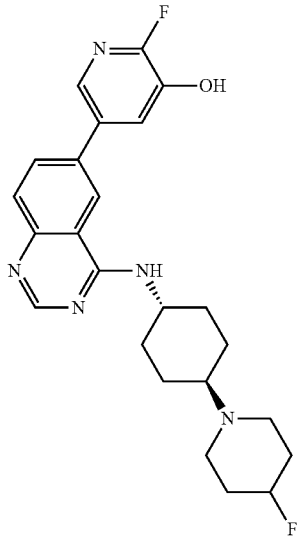 [SMILES: Oc1cc(-c2ccc3ncnc(N[C@H]4CC[C@H](N5CCC(F)CC5)CC4)c3c2)cnc1F] | 2-fluoro-5-(4-{[trans-4-(4-fluoropiperidin-1-yl)cyclohexyl]amino}quinazolin-6-yl)pyridin-3-ol | Calc'd 440.0, found 440 |
| 5-14 | 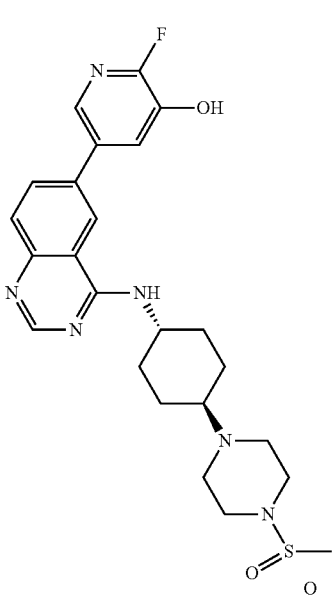 | 2-fluoro-5-[4-({trans-4-[4-(methylsulfonyl)piperazin-1-yl]cyclohexyl}amino)quinazolin-6-yl]pyridin-3-ol | Calc'd 501.0, found 501 |

TABLE 6-continued
| Example # | Structure | Chemical Name | MS (M + 1) |
|---|---|---|---|
| 5-15 | 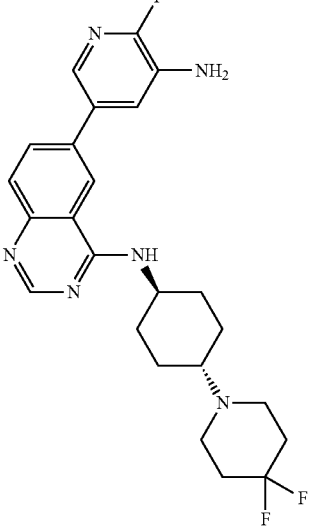 | 6-(5-amino-6-fluoropyridin-3-yl)-N-[trans-4-(4,4-difluoropiperidin-1-yl)cyclohexyl]quinazolin-4-amine | Calc'd 457.0, found 457 |
| 5-16 | 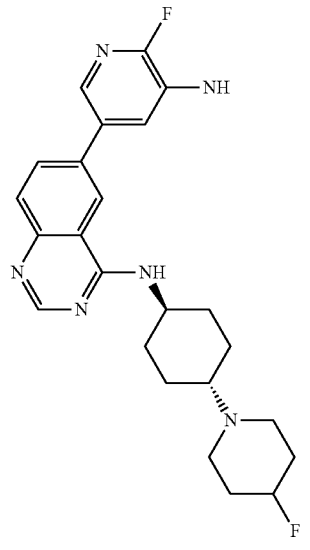 [SMILES: Nc1cc(-c2ccc3ncnc(N[C@H]4CC[C@H](N5CCC(F)CC5)CC4)c3c2)cnc1F] | 6-(5-amino-6-fluoropyridin-3-yl)-N-[trans-4-(4-fluoropiperidin-1-yl)cyclohexyl]quinazolin-4-amine | Calc'd 439.0, found 439 |
| 5-17 | 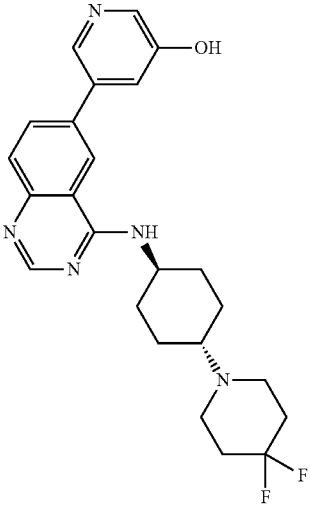 [SMILES: Oc1cncc(-c2ccc3ncnc(N[C@H]4CC[C@H](N5CCC(F)(F)CC5)CC4)c3c2)c1] | 5-(4-{[trans-4-(4,4-difluoropiperidin-1-yl)cyclohexyl]amino}quinazolin-6-yl)pyridin-3-ol | Calc'd 440.0, found 440 |

TABLE 6-continued
| Example # | Structure | Chemical Name | MS (M + 1) |
|---|---|---|---|
| 5-18 | 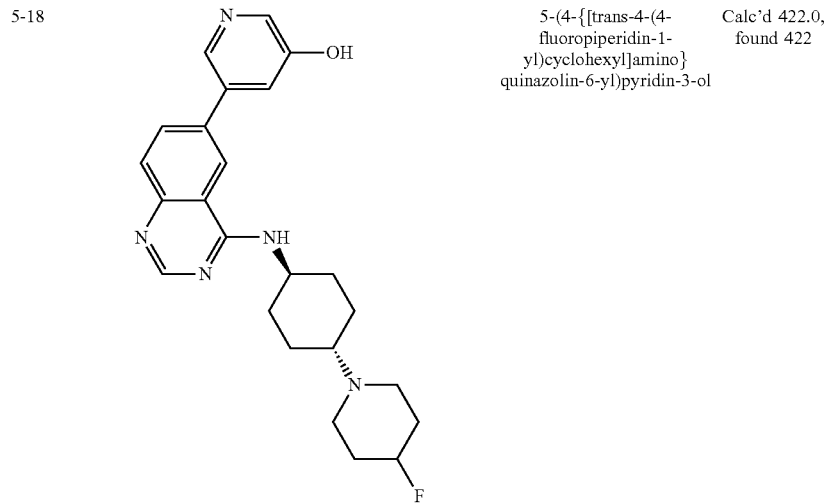 | 5-(4-{[trans-4-(4-fluoropiperidin-1-yl)cyclohexyl]amino}quinazolin-6-yl)pyridin-3-ol | Calc'd 422.0, found 422 |
| 5-19 | 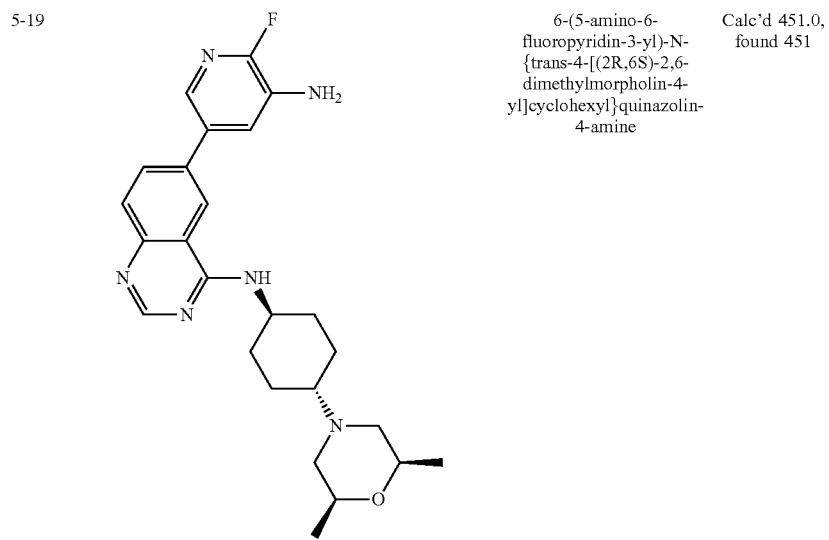 | 6-(5-amino-6-fluoropyridin-3-yl)-N-{trans-4-[(2R,6S)-2,6-dimethylmorpholin-4-yl]cyclohexyl}quinazolin-4-amine | Calc'd 451.0, found 451 |

TABLE 6-continued
| Example # | Structure | Chemical Name | MS (M + 1) |
|---|---|---|---|
| 5-20 | 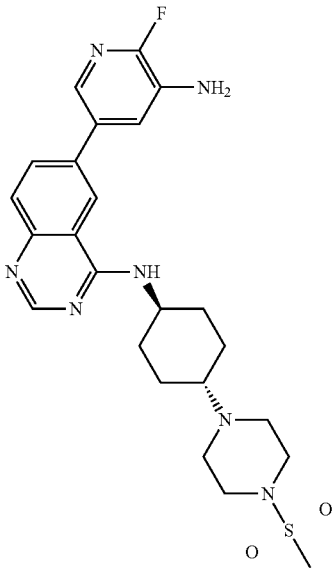 | 6-(5-amino-6-fluoropyridin-3-yl)-N-{trans-4-[4-(methylsulfonyl)piperazin-1-yl]cyclohexyl}quinazolin-4-amine | Calc'd 500.0, found 500 |
| 5-21 | 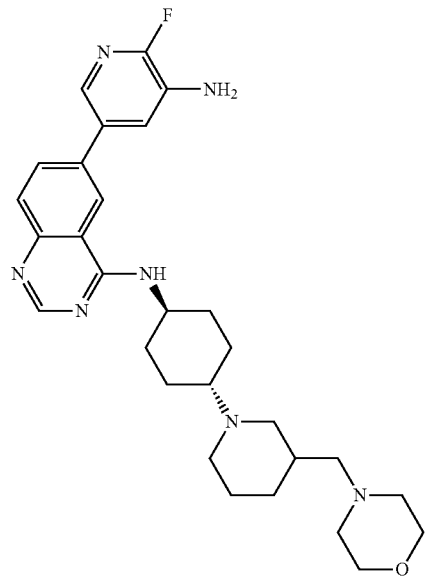 [SMILES: Nc1cc(-c2ccc3ncnc(N[C@H]4CC[C@H](N5CCCC(CN6CCOCC6)C5)CC4)c3c2)cnc1F] | 6-(5-amino-6-fluoropyridin-3-yl)-N-{trans-4-[3-(morpholin-4-ylmethyl)piperidin-1-yl]cyclohexyl}quinazolin-4-amine | Calc'd 520.0, found 520 |

TABLE 6-continued
| Example # | Structure | Chemical Name | MS (M + 1) |
|---|---|---|---|
| 5-22 | 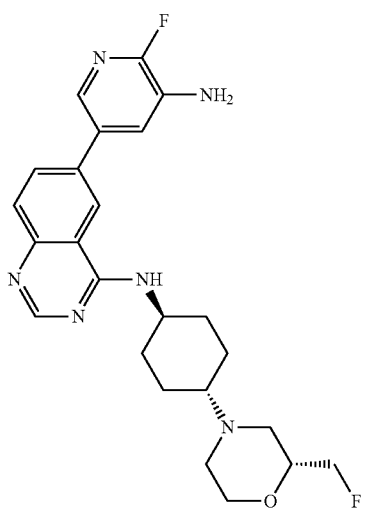 | 6-(5-amino-6-fluoropyridin-3-yl)-N-{trans-4-[(2R)-2-(fluoromethyl)morpholin-4-yl]cyclohexyl}quinazolin-4-amine | Calc'd 455.0, found 455 |
| 5-23 | 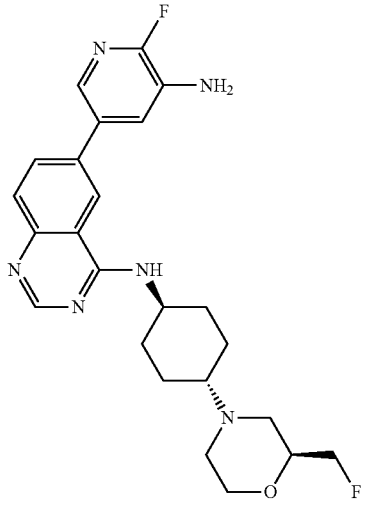 [SMILES: Nc1cc(-c2ccc3ncnc(N[C@H]4CC[C@H](N5CCO[C@H](CF)C5)CC4)c3c2)cnc1F] | 6-(5-amino-6-fluoropyridin-3-yl)-N-{trans-4-[(2S)-2-(fluoromethyl)morpholin-4-yl]cyclohexyl}quinazolin-4-amine | Calc'd 455.0, found 455 |
| 5-24 | 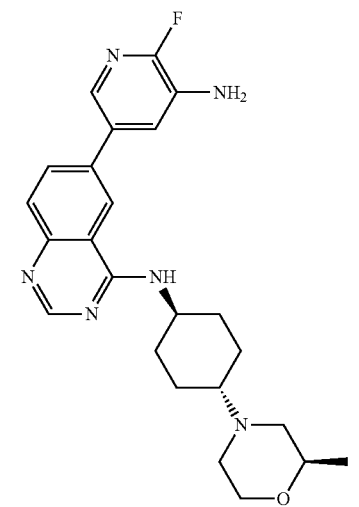 [SMILES: C[C@@H]1CN([C@H]2CC[C@H](Nc3ncnc4ccc(-c5cnc(F)c(N)c5)cc34)CC2)CCO1] | 6-(5-amino-6-fluoropyridin-3-yl)-N-{trans-4-[(2R)-2-methylmorpholin-4-yl]cyclohexyl}quinazolin-4-amine | Calc'd 437.0, found 437 |

TABLE 6-continued

| Example # | Structure | Chemical Name | MS (M + 1) |
|---|---|---|---|
| 5-25 | 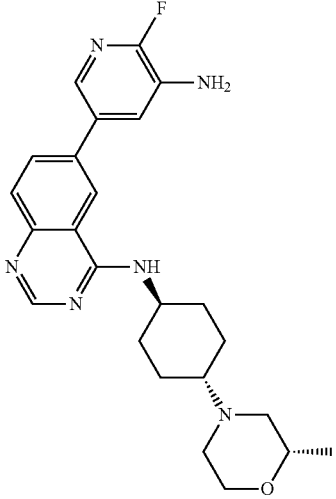 [SMILES: C[C@H]1CN([C@H]2CC[C@H](Nc3ncnc4ccc(-c5cnc(F)c(N)c5)cc34)CC2)CCO1] | 6-(5-amino-6-fluoropyridin-3-yl)-N-{trans-4-[(2S)-2-methylmorpholin-4-yl]cyclohexyl}quinazolin-4-amine | Calc'd 437.0, found 437 |
| 5-26 | 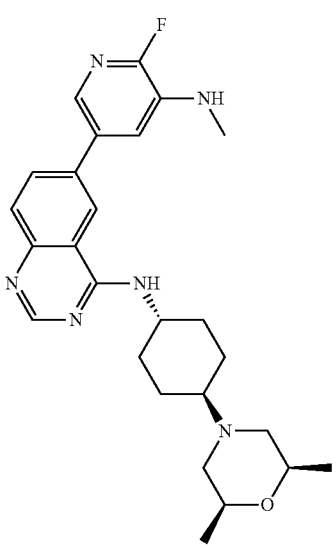 [SMILES: CNc1cc(-c2ccc3ncnc(N[C@H]4CC[C@H](N5C[C@@H](C)O[C@@H](C)C5)CC4)c3c2)cnc1F] | N-{trans-4-[(2R,6S)-2,6-dimethylmorpholin-4-yl]cyclohexyl}-6-[6-fluoro-5-(methylamino)pyridin-3-yl]quinazolin-4-amine | Calc'd 465.0, found 465 |
| 5-27 | 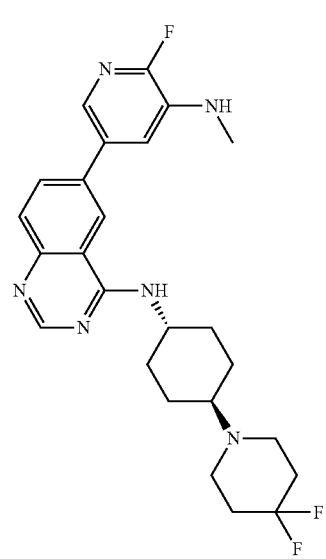 [SMILES: CNc1cc(-c2ccc3ncnc(N[C@H]4CC[C@H](N5CCC(F)(F)CC5)CC4)c3c2)cnc1F] | N-[trans-4-(4,4-difluoropiperidin-1-yl)cyclohexyl]-6-[6-fluoro-5-(methylamino)pyridin-3-yl]quinazolin-4-amine | Calc'd 471.0, found 471 |

TABLE 6-continued
| Example # | Structure | Chemical Name | MS (M + 1) |
|---|---|---|---|
| 5-28 | 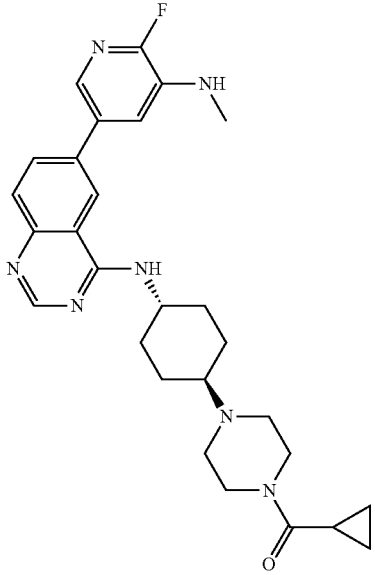 [SMILES: CNc1cc(-c2ccc3ncnc(N[C@H]4CC[C@H](N5CCN(C(=O)C6CC6)CC5)CC4)c3c2)cnc1F] | cyclopropyl{4-[trans-4-({6-[6-fluoro-5-(methylamino)pyridin-3-yl]quinazolin-4-yl}amino)cyclohexyl]piperazin-1-yl}methanone | Calc'd 504.0, found 504 |
| 5-29 | 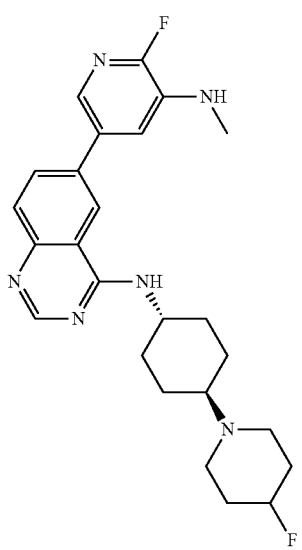 [SMILES: CNc1cc(-c2ccc3ncnc(N[C@H]4CC[C@H](N5CCC(F)CC5)CC4)c3c2)cnc1F] | 6-[6-fluoro-5-(methylamino)pyridin-3-yl]-N-[trans-4-(4-fluoropiperidin-1-yl)cyclohexyl]quinazolin-4-amine | Calc'd 453.0, found 453 |

TABLE 6-continued

| Example # | Structure | Chemical Name | MS (M + 1) |
|---|---|---|---|
| 5-30 | 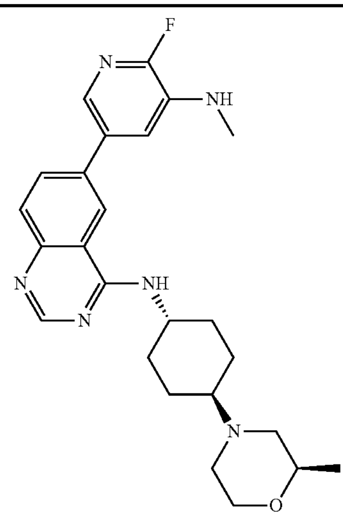 | 6-[6-fluoro-5-(methylamino)pyridin-3-yl]-N-{trans-4-[(2R)-2-methylmorpholin-4-yl]cyclohexyl}quinazolin-4-amine | Calc'd 451.0, found 451 |
| 5-31 | 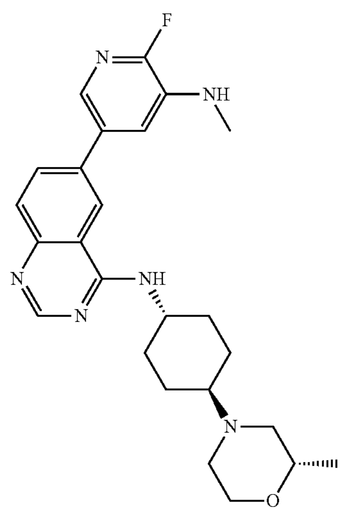 [SMILES: CNc1cc(-c2ccc3ncnc(N[C@H]4CC[C@H](N5CCO[C@@H](C)C5)CC4)c3c2)cnc1F] | 6-[6-fluoro-5-(methylamino)pyridin-3-yl]-N-{trans-4-[(2S)-2-methylmorpholin-4-yl]cyclohexyl}quinazolin-4-amine | Calc'd 451.0, found 451 |

Biological Data

Examples of the instant invention were tested by the assay described below and were found to have IRAK4 inhibitory activity. Other assays are known in the literature and could be readily performed by those of skill in the art.

IRAK4 Kinase Assay

The kinase activity of IRAK4 is determined by its ability to catalyze the phosphorylation of a fluorescent polypeptide substrate. The extent of phosphorylation is measured using the IMAP technology (Molecular Devices) where the phosphorylated fluorescent substrate binds to the large M(III)-based nanoparticles which reduces the rotational speed of the substrate and thus increases its fluorescent polarization (FP).

20 μL reaction mixture contains 10 mM TriHCl, pH 7.2, 0.5 nM GST tagged IRAK4 (SignalChem), 100 nM fluorescent peptide substrate (RP7030, Molecular Devices), 100 μM ATP, 1 mM DDT, 1 mM $MgCl_2$, and 0.01% Tween 20. The reaction is initiated by the addition of ATP. After incubation for 30 minutes at 25° C., 60 μL of Progressive IMAP Reagent (Molecular Devices) is added to stop the reaction. Change in RP7030's FP is determined by a FP reader (Analyst HT, LJL BioSystems).

The following table shows the activity data for compounds of the instant invention.

TABLE 7

| Example # | IRAK4 IC50 (nM) |
|---|---|
| 1-1 | 27 |
| 1-2 | 3158 |
| 1-3 | 2293 |
| 1-4 | 1613 |
| 1-5 | 19 |
| 1-6 | 11 |
| 1-7 | 13 |
| 1-8 | 25 |
| 1-9 | 5 |
| 1-10 | 1 |
| 1-11 | 36 |
| 1-12 | 17 |
| 1-13 | 28 |
| 1-14 | 1362 |
| 1-15 | 1325 |

TABLE 7-continued

| Example # | IRAK4 IC50 (nM) |
|---|---|
| 1-16 | 217 |
| 1-17 | 372 |
| 1-18 | 92 |
| 1-19 | 358 |
| 1-20 | 85 |
| 1-21 | 155 |
| 1-22 | 54 |
| 1-23 | 498 |
| 1-24 | 333 |
| 1-25 | 3 |
| 1-26 | 698 |
| 1-27 | 43 |
| 1-28 | 7 |
| 1-29 | 19 |
| 1-30 | 42 |
| 1-31 | 45 |
| 1-32 | 9 |
| 1-33 | 9 |
| 1-34 | 11 |
| 1-35 | 394 |
| 1-36 | 19 |
| 1-37 | 504 |
| 1-38 | 71 |
| 1-39 | 43 |
| 1-40 | 83 |
| 1-41 | 2346 |
| 1-42 | 11 |
| 1-43 | 25 |
| 1-44 | 32 |
| 1-45 | 81 |
| 1-46 | 19 |
| 1-47 | 3 |
| 1-48 | 9 |
| 1-49 | 161 |
| 1-50 | 11 |
| 1-51 | 25 |
| 1-52 | 200 |
| 1-53 | 24 |
| 1-54 | 46 |
| 1-55 | 46 |
| 1-56 | 129 |
| 1-57 | 6734 |
| 1-58 | 21 |
| 1-59 | 124 |
| 1-60 | 1691 |
| 1-61 | 109 |
| 1-62 | 23 |
| 1-63 | 3 |
| 1-64 | 4 |
| 1-65 | <0.5 |
| 1-66 | 5 |
| 1-67 | 15 |
| 1-68 | 25 |
| 1-69 | 18 |
| 1-70 | 5 |
| 1-71 | 17 |
| 1-72 | 6 |
| 1-73 | 1 |
| 1-74 | 3 |
| 1-75 | 39 |
| 1-76 | 223 |
| 1-77 | 1312 |
| 1-78 | 433 |
| 1-79 | 38 |
| 1-80 | 2 |
| 1-81 | 2 |
| 1-82 | 2 |
| 1-83 | 9 |
| 1-84 | 1 |
| 1-85 | 10 |
| 1-86 | 23 |
| 1-87 | 15 |
| 1-88 | 100 |
| 1-89 | 18 |
| 1-90 | 169 |
| 1-91 | 20 |
| 1-92 | 24 |
| 1-93 | 26 |
| 1-94 | 10 |
| 1-95 | 330 |
| 1-96 | 9 |
| 1-97 | 22 |
| 1-98 | 21 |
| 1-99 | 11 |
| 1-100 | 1 |
| 2-1 | 6027 |
| 2-2 | 92 |
| 2-3 | 390 |
| 2-4 | 119 |
| 2-5 | 928 |
| 2-6 | 1 |
| 2-7 | 1 |
| 2-8 | 122 |
| 2-9 | 12 |
| 2-10 | 8 |
| 2-11 | 62 |
| 2-12 | 261 |
| 2-13 | 324 |
| 2-14 | 80 |
| 2-15 | 152 |
| 2-16 | 48 |
| 2-17 | 41 |
| 2-18 | 52 |
| 2-19 | 184 |
| 2-20 | 22 |
| 2-21 | 126 |
| 2-22 | 492 |
| 2-23 | 1193 |
| 2-24 | 104 |
| 2-25 | 88 |
| 2-26 | 562 |
| 2-27 | 159 |
| 2-28 | 2 |
| 2-29 | 20 |
| 2-30 | <0.5 |
| 2-31 | 73 |
| 2-32 | 1 |
| 2-33 | 28 |
| 2-34 | 13 |
| 2-35 | 37 |
| 2-36 | 10 |
| 3-1 | 1 |
| 4-1 | 32 |
| 5-1 | <0.5 |
| 5-2 | 1 |
| 5-3 | 1 |
| 5-4 | <0.5 |
| 5-5 | 1 |
| 5-6 | <0.5 |
| 5-7 | 8 |
| 5-8 | 3 |
| 5-9 | 3 |
| 5-10 | 8 |
| 5-11 | 2 |
| 5-12 | 5 |
| 5-13 | <0.5 |
| 5-14 | 1 |
| 5-15 | 2 |
| 5-16 | 1 |
| 5-17 | <0.5 |
| 5-18 | <0.5 |
| 5-19 | 1 |
| 5-20 | 4 |
| 5-21 | 2 |
| 5-22 | 4 |
| 5-23 | 6 |
| 5-24 | 1 |
| 5-25 | 1 |
| 5-26 | 1 |
| 5-27 | 2 |
| 5-28 | 1 |
| 5-29 | 2 |
| 5-30 | 1 |
| 5-31 | 1 |

What is claimed is:

1. A compound according to Formula I:

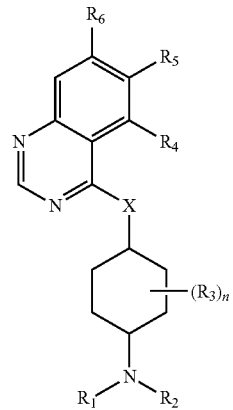

I wherein:

X is NH or O;

b is 0 or 1;

n is 0, 1, 2, 3 or 4;

$R_1$ and $R_2$ are independently H and $(C_1-C_4)$alkyl, or $R_1$ and $R_2$ can be taken together with the nitrogen to which they are attached to form a heterocycle optionally containing, in addition to the nitrogen, one or two additional heteroatoms selected from N, O and S, said alkyl and heterocycle are optionally substituted with one or more substituents selected from $R_a$;

$R_3$ is $(C_1-C_4)$alkyl wherein two adjacent alkyl groups can join together and form a bridged moiety of 3-6 carbon atoms;

$R_4$ is absent, halo or $O_b(C_1-C_4)$alkyl;

$R_5$ is aryl or heteroaryl each optionally substituted with one or more substituents selected from $R_b$;

$R_6$ is absent, halo, or $O(C_1-C_4)$alkyl;

$R_a$ is independently selected from: halo, $O_b(C_1-C_4)$alkyl, $SO_2(C_1-C_4)$alkyl, $C(O)C_1-C_4$ alkyl, said alkyl optionally substituted with halo or heterocyclyl; and $R_b$ is independently selected from OH, halo, $CHF_2$, $CF_3$, COOH, $SO_2(C_1-C_4)$alkyl, $C=O(O)C_1-C_4$ alkyl, $O_b(C_1-C_4)$alkyl, aryl, heterocyclyl, CN, $C(O)N(R_c)_2$, $N(R_c)_2$; said $R_c$ and alkyl are optionally substituted with OH, $O(C_1-C_4)$alkyl and heterocyclyl; and $R_c$ is independently H, $SO_2(C_1-C_4)$alkyl, or $C_1-C_4$ alkyl;

or a pharmaceutically acceptable salt or a stereoisomer thereof.

2. A compound according to claim 1 of Formula II:

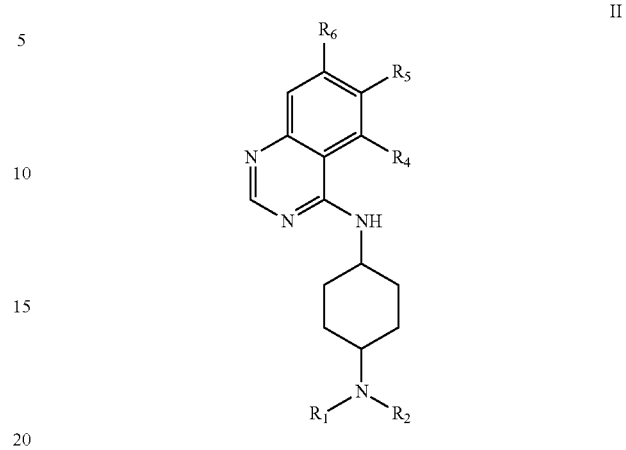

II wherein:

b is 0 or 1;

$R_1$ and $R_2$ are independently H and $(C_1-C_4)$alkyl, or $R_1$ and $R_2$ can be taken together with the nitrogen to which they are attached to form: morpholinyl, piperidinyl, azetidinyl and piperazinyl, said alkyl, morpholinyl, piperidinyl, azetidinyl and piperaziyle are optionally substituted with one or more substituents selected from $R_a$;

$R_4$ is absent or methyl;

$R_5$ is aryl or heteroaryl each optionally substituted with one or more substituents selected from $R_b$;

$R_6$ is absent or F;

$R_a$ is independently selected from: F, $O_b(C_1-C_4)$alkyl, $SO_2(C_1-C_4)$alkyl, $C(O)C_1-C_4$ alkyl, said alkyl optionally substituted with F or morpholinyl;

$R_b$ is independently selected from OH, halo, $CHF_2$, $CF_3$, COOH, $SO_2(C_1-C_4)$alkyl, $C=O(O)C_1-C_4$ alkyl, $O_b(C_1-C_4)$alkyl, aryl, heterocyclyl, CN, $C(O)N(R_c)_2$, $N(R_c)_2$; said $R_c$ and alkyl are optionally substituted with OH, $O(C_1-C_4)$alkyl and heterocyclyl; and $R_c$ is independently H, $SO_2(C_1-C_4)$alkyl, or $C_1-C_4$ alkyl;

or a pharmaceutically acceptable salt or a stereoisomer thereof.

3. A compound which is selected from:

trans-N,N-dimethyl-N'-[6(6-methylpyridazin-4-yl)quinazolin-4-yl]cyclohexane-1,4-diamine;

cis or trans-N,N-dimethyl-N'-(6-phenylquinazolin-4-yl)cyclohexane-1,4-diamine;

cis or trans-N,N-dimethyl-N'-[6-(pyridin-4-yl)quinazolin-4-yl]cyclohexane-1,4-diamine;

cis or trans-N,N-dimethyl-N'-[6-(pyridin-3-yl)quinazolin-4-yl]cyclohexane-1,4-diamine;

cis or trans-N,N-dimethyl-N'-(6-phenylquinazolin-4-yl)cyclohexane-1,4-diamine;

cis or trans-N,N-dimethyl-N'-[6-(pyridin-4-yl)quinazolin-4-yl]cyclohexane-1,4-diamine;

cis or trans-N,N-dimethyl-N'-[6-(pyridin-3-yl)quinazolin-4-yl]cyclohexane-1,4-diamine;

trans-N'-[6-(2-methoxypyridin-4-yl)quinazolin-4-yl]-N,N-dimethylcyclohexane-1,4-diamine;

trans-N,N-dimethyl-N'-[6-(1-methyl-1H-pyrazol-4-yl)quinazolin-4-yl]cyclohexane-1,4-diamine;

cis or trans-N,N-dimethyl-N'-[6-(1H-pyrazol-4-yl)quinazolin-4-yl]cyclohexane-1,4-diamine;

cis or trans-N'-[6-(6-aminopyridin-3-yl)quinazolin-4-yl]-N,N-dimethylcyclohexane-1,4-diamine;
trans-N,N-dimethyl-N'-[6-(1H-pyrazol-3-yl)quinazolin-4-yl]cyclohexane-1,4-diamine;
trans-N,N-dimethyl-N'-{6-[2-(methylamino)pyrimidin-5-yl]quinazolin-4-yl}cyclohexane-1,4-diamine;
trans-N'-{6-[1-(1-ethoxyethyl)-1H-pyrazol-4-yl]quinazolin-4-yl}-N,N-dimethylcyclohexane-1,4-diamine;
trans-N,N-dimethyl-N'-(6-{1-[2-(morpholin-4-yl)ethyl]-1H-pyrazol-4-yl}quinazolin-4-yl)cyclohexane-1,4-diamine;
trans-N,N-dimethyl-N'-{6-[1-(tetrahydro-2H-pyran-2-yl)-1H-pyrazol-4-yl]quinazolin-4-yl}cyclohexane-1,4-diamine;
trans-N,N-dimethyl-N'-{6-[1-(pyridin-2-ylmethyl)-1H-pyrazol-4-yl]quinazolin-4-yl}cyclohexane-1,4-diamine;
trans-N'-[6-(1-ethyl-1H-pyrazol-4-yl)quinazolin-4-yl]-N,N-dimethylcyclohexane-1,4-diamine;
trans-N,N-dimethyl-N'-{6-[1-(pyridin-4-ylmethyl)-1H-pyrazol-4-yl]quinazolin-4-yl}cyclohexane-1,4-diamine;
4-(4-{[trans-4-(dimethylamino)cyclohexyl]amino}quinazolin-6-yl)pyridine-3-carbonitrile;
trans-N,N-dimethyl-N'-[6-(3-methylpyridin-4-yl)quinazolin-4-yl]cyclohexane-1,4-diamine;
3-(4-{[trans-4-(dimethylamino)cyclohexyl]amino}quinazolin-6-yl)pyridine-4-carbonitrile;
trans-N,N-dimethyl-N'-{6-[5-(morpholin-4-yl)pyridin-3-yl]quinazolin-4-yl}cyclohexane-1,4-diamine;
trans-N'-[6-(3,5-dimethylisoxazol-4-yl)quinazolin-4-yl]-N,N-dimethylcyclohexane-1,4-diamine;
trans-N,N-dimethyl-N'-[6-(pyrimidin-5-yl)quinazolin-4-yl]cyclohexane-1,4-diamine;
trans-N,N-dimethyl-N'-[6-(5-methyl-3-phenylisoxazol-4-yl)quinazolin-4-yl]cyclohexane-1,4-diamine;
5-(4-{[trans-4-(dimethylamino)cyclohexyl]amino}quinazolin-6-yl)pyridine-2-carbonitrile;
5-(4-{[trans-4-(dimethylamino)cyclohexyl]amino}quinazolin-6-yl)pyridin-2-ol;
trans-N'-[6-(2-aminopyrimidin-5-yl)quinazolin-4-yl]-N,N-dimethylcyclohexane-1,4-diamine;
trans-N,N-dimethyl-N'-[6-(6-methylpyridin-3-yl)quinazolin-4-yl]cyclohexane-1,4-diamine;
methyl 5-(4-{[trans-4-(dimethylamino)cyclohexyl]amino}quinazolin-6-yl)pyridine-3-carboxylate;
trans-N'-[6-(isoxazol-4-yl)quinazolin-4-yl]-N,N-dimethylcyclohexane-1,4-diamine;
5-(4-{[trans-4-(dimethylamino)cyclohexyl]amino}quinazolin-6-yl)pyrimidin-2-ol;
trans-N'-[6-(3-fluoropyridin-4-yl)quinazolin-4-yl]-N,N-dimethylcyclohexane-1,4-diamine;
trans-N'-[6-(4-methoxypyridin-3-yl)quinazolin-4-yl]-N,N-dimethylcyclohexane-1,4-diamine;
trans-N,N-dimethyl-N'-{6-[4-(trifluoromethyl)pyridin-3-yl]quinazolin-4-yl}cyclohexane-1,4-diamine;
5-(4-{[trans-4-(dimethylamino)cyclohexyl]amino}quinazolin-6-yl)pyridine-3-carboxylic acid;
trans-N'-[6-(3-methoxypyridin-4-yl)quinazolin-4-yl]-N,N-dimethylcyclohexane-1,4-diamine;
3-(4-{[trans-4-(dimethylamino)cyclohexyl]amino}quinazolin-6-yl)pyridine-2-carbonitrile;
trans-N'-{6-[5-(2-methoxyethoxy)pyridin-3-yl]quinazolin-4-yl}-N,N-dimethylcyclohexane-1,4-diamine;
trans-N,N-dimethyl-N'-{6-[5-(methylsulfonyl)pyridin-3-yl]quinazolin-4-yl}cyclohexane-1,4-diamine;
trans-N'-{6-[2-(cyclopropylamino)pyrimidin-5-yl]quinazolin-4-yl}-N,N-dimethylcyclohexane-1,4-diamine;
2-{[5-(4-{[trans-4-(dimethylamino)cyclohexyl]amino}quinazolin-6-yl)pyrimidin-2-yl]amino}ethanol;
3-(4-{[trans-4-(dimethylamino)cyclohexyl]amino}quinazolin-6-yl)benzonitrile;
trans-N'-[6-(1H-indol-5-yl)quinazolin-4-yl]-N,N-dimethylcyclohexane-1,4-diamine;
N-[trans-4-(morpholin-4-yl)cyclohexyl]-6-(pyridin-3-yl)quinazolin-4-amine;
N-[trans-4-(morpholin-4-yl)cyclohexyl]-6-(pyrimidin-5-yl)quinazolin-4-amine;
N-[trans-4-(morpholin-4-yl)cyclohexyl]-6-(pyridin-4-yl)quinazolin-4-amine;
trans-N'-[6-(2,3-dihydro-1,4-benzodioxin-6-yl)quinazolin-4-yl]-N,N-dimethylcyclohexane-1,4-diamine;
trans-N,N-dimethyl-N'-[6-(pyridazin-4-yl)quinazolin-4-yl]cyclohexane-1,4-diamine;
trans-N'-[6-(5-methoxypyridin-3-yl)quinazolin-4-yl]-N,N-dimethylcyclohexane-1,4-diamine;
trans-N'-[6-(5-fluoro-6-methoxypyridin-3-yl)quinazolin-4-yl]-N,N-dimethylcyclohexane-1,4-diamine;
trans-N'-[6-(5-fluoropyridin-3-yl)quinazolin-4-yl]-N,N-dimethylcyclohexane-1,4-diamine;
5-(4-{[trans-4-(dimethylamino)cyclohexyl]amino}quinazolin-6-yl)pyridine-3-carbonitrile;
trans-N,N-dimethyl-N'-[6-(1H-pyrrolo[2,3-b]pyridin-5-yl)quinazolin-4-yl]cyclohexane-1,4-diamine;
N-tert-butyl-5-(4-{[trans-4-(dimethylamino)cyclohexyl]amino}quinazolin-6-yl)pyridine-3-carboxamide;
trans-N,N-dimethyl-N'-[6-(4-methyl-3,4-dihydro-2H-pyrido[3,2-b][1,4]oxazin-7-yl)quinazolin-4-yl]cyclohexane-1,4-diamine;
trans-N,N-dimethyl-N'-[6-(1H-pyrazolo[3,4-b]pyridin-5-yl)quinazolin-4-yl]cyclohexane-1,4-diamine;
trans-N,N-dimethyl-N'-[6-(1H-pyrrolo[3,2-b]pyridin-6-yl)quinazolin-4-yl]cyclohexane-1,4-diamine;
trans-N,N-dimethyl-N'-[6-(3-methyl-3H-imidazo[4,5-b]pyridin-6-yl)quinazolin-4-yl]cyclohexane-1,4-diamine;
trans-N'-[6-(furo[3,2-b]pyridin-6-yl)quinazolin-4-yl]-N,N-dimethylcyclohexane-1,4-diamine;
trans-N'-[6-(3,5-difluorophenyl)quinazolin-4-yl]-N,N-dimethylcyclohexane-1,4-diamine;
3-(4-{[trans-4-(dimethylamino)cyclohexyl]amino}quinazolin-6-yl)-5-fluorophenol;
5-(4-{[trans-4-(dimethylamino)cyclohexyl]amino}quinazolin-6-yl)-2,3-difluorophenol;
5-(4-{[trans-4-(morpholin-4-yl)cyclohexyl]amino}quinazolin-6-yl)pyridin-3-ol;
3-fluoro-5-{4-[(trans-4-morpholin-4-ylcyclohexyl)amino]quinazolin-6-yl}phenol;
4-{4-[(trans-4-morpholin-4-ylcyclohexyl)amino]quinazolin-6-yl}pyridin-2-ol ;
6-(3,5-difluorophenyl)-N-(trans-4-morpholin-4-ylcyclohexyl)quinazolin-4-amine;
6-(5-methoxypyridin-3-yl)-N'-[trans-4-(morpholin-4-yl)cyclohexyl]quinazolin-4-amine;
2,3-difluoro-5-{4-[(trans-4-morpholin-4-ylcyclohexyl)amino]quinazolin-6-yl}phenol;
6-(5-amino-6-methoxypyridin-3-yl)-N-(trans-4-morpholin-4-ylcyclohexyl)quinazolin-4-amine;
3-{4-[(trans-4-morpholin-4-ylcyclohexyl)amino]quinazolin-6-yl}phenol;
6-(5-aminopyridin-3-yl)-N-(trans-4-morpholin-4-ylcyclohexyl)quinazolin-4-amine;

6-(2-aminopyridin-4-yl)-N-(trans-4-morpholin-4-ylcyclohexyl)quinazolin-4-amine;
6-(1-methyl-1H-pyrazol-4-yl)-N-(trans-4-morpholin-4-ylcyclohexyl)quinazolin-4-amine;
5-methyl-N-(trans-4-morpholin-4-ylcyclohexyl)-6-pyrimidin-5-ylquinazolin-4-amine;
5-methyl-6-(1-methyl-1H-pyrazol-4-yl)-N-(trans-4-morpholin-4-ylcyclohexyl)quinazolin-4-amine;
5-methyl-N-(trans-4-morpholin-4-ylcyclohexyl)-6-pyridin-4-ylquinazolin-4-amine;
5-{5-methyl-4-[(trans-4-morpholin-4-ylcyclohexyl)amino]quinazolin-6-yl}pyridin-3-ol;
7-fluoro-N-(trans-4-morpholin-4-ylcyclohexyl)-6-(1H-pyrazol-4-yl)quinazolin-4-amine;
6-[5-(methylamino)pyridin-3-yl]-N-(trans-4-morpholin-4-ylcyclohexyl)quinazolin-4-amine;
N-(trans-4-morpholin-4-ylcyclohexyl)-6-(1H-pyrazol-4-yl)quinazolin-4-amine;
6-(3-aminophenyl)-N-(trans-4-morpholin-4-ylcyclohexyl)quinazolin-4-amine;
5-{7-fluoro-4-[(trans-4-morpholin-4-ylcyclohexyl)amino]quinazolin-6-yl}pyridin-3-ol;
6-(5-aminopyridin-3-yl)-7-fluoro-N-(trans-4-morpholin-4-ylcyclohexyl)quinazolin-4-amine;
7-fluoro-6-[5-(methylamino)pyridin-3-yl]-N-(trans-4-morpholin-4-ylcyclohexyl)quinazolin-4-amine;
7-fluoro-N-(trans-4-morpholin-4-ylcyclohexyl)-6-pyrimidin-5-ylquinazolin-4-amine;
6-(1H-indol-4-yl)-N-[trans-4-(morpholin-4-yl)cyclohexyl]quinazolin-4-amine;
6-(2-methylpyrimidin-5-yl)-N-[trans-4-(morpholin-4-yl)cyclohexyl]quinazolin-4-amine;
N-[cis-4-(morpholin-4-yl)cyclohexyl]-6-[2-(trifluoromethyl)pyrimidin-5-yl]quinazolin-4-amine;
N-[trans-4-(morpholin-4-yl)cyclohexyl]-6-(1H-pyrazol-3-yl)quinazolin-4-amine;
N-[5-(4-{[trans-4-(morpholin-4-yl)cyclohexyl]amino}quinazolin-6-yl)pyridin-3-yl]methanesulfonamide;
6-(5-methylpyridin-3-yl)-N-[trans-4-(morpholin-4-yl)cyclohexyl]quinazolin-4-amine;
[5-(4-{[trans-4-(morpholin-4-yl)cyclohexyl]amino}quinazolin-6-yl)pyridin-3-yl]methanol;
2-[5-(4-{[trans-4-(morpholin-4-yl)cyclohexyl]amino}quinazolin-6-yl)pyridin-3-yl]propan-2-ol;
6-(isoxazol-4-yl)-N-[trans-4-(morpholin-4-yl)cyclohexyl]quinazolin-4-amine;
6-(5-fluoropyridin-3-yl)-N-[trans-4-(morpholin-4-yl)cyclohexyl]quinazolin-4-amine;
5-(4-{[trans-4-(morpholin-4-yl)cyclohexyl]amino}quinazolin-6-yl)pyridine-3-carbonitrile;
6-(5-chloropyridin-3-yl)-N-[trans-4-(morpholin-4-yl)cyclohexyl]quinazolin-4-amine;
2-chloro-5-(4-{[trans-4-(morpholin-4-yl)cyclohexyl]amino}quinazolin-6-yl)pyridin-3-ol;
ethyl 1-methyl-3-(4-(((trans)-4-morpholinocyclohexyl)amino)quinazolin-6-yl)-1H-pyrazole-4-carboxylate;
6-(2-methyl-1,3-thiazol-4-yl)-N-(trans-4-morpholin-4-ylcyclohexyl)quinazolin-4-amine;
6-[2-(1-methylethyl)-1,3-thiazol-4-yl]-N-(trans-4-morpholin-4-ylcyclohexyl)quinazolin-4-amine;
N-(trans-4-morpholin-4-ylcyclohexyl)-6-[5-(trifluoromethyl)pyridin-3-yl]quinazolin-4-amine;
3-{4-[(trans-4-morpholin-4-ylcyclohexyl)amino]quinazolin-6-yl}-5-(trifluoromethyl)pyridin-2-ol ;
2-chloro-5-{4-[(trans-4-morpholin-4-ylcyclohexyl)amino]quinazolin-6-yl}pyridin-3-ol;
6-(5-amino-6-fluoropyridin-3-yl)-N-(trans-4-morpholin-4-ylcyclohexyl)quinazolin-4-amine;
6-{4-[(trans-4-morpholin-4-ylcyclohexyl)amino]quinazolin-6-yl}pyridine-2-carboxylic acid;
6-(4-fluoro-1H-pyrazol-3-yl)-N-(trans-4-morpholin-4-ylcyclohexyl)quinazolin-4-amine;
4-{4-[(trans-4-morpholin-4-ylcyclohexyl)amino]quinazolin-6-yl}-1H-pyrazole-3-carbonitrile;
5-{4-[(trans-4-morpholin-4-ylcyclohexyl)amino]quinazolin-6-yl}-1H-1,2,3-triazole-4-carbonitrile;
(1-methyl-4-{4-[(trans-4-morpholin-4-ylcyclohexyl)amino]quinazolin-6-yl}-1H-pyrazol-3-yl)methanol;
6-(1-methyl-1H-pyrazol-5-yl)-N-(trans-4-morpholin-4-ylcyclohexyl)quinazolin-4-amine;
N-(trans-4-morpholin-4-ylcyclohexyl)-6-[3-(trifluoromethyl)-1H-pyrazol-4-yl]quinazolin-4-amine;
6-(1-methyl-1H-1,2,3-triazol-5-yl)-N-(trans-4-morpholin-4-ylcyclohexyl)quinazolin-4-amine;
6-(2,3-dihydro-1H-pyrrolo[3,2-b]pyridin-6-yl)-N-[trans-4-(morpholin-4-yl)cyclohexyl]quinazolin-4-amine;
3-(4-{[trans-4-(morpholin-4-yl)cyclohexyl]amino}quinazolin-6-yl)thiophene-2-carbonitrile;
4-(4-{[trans-4-(morpholin-4-yl)cyclohexyl]amino}quinazolin-6-yl)thiophene-3-carbonitrile;
6-(4-methyl-1H-imidazol-5-yl)-N-[trans-4-(morpholin-4-yl)cyclohexyl]quinazolin-4-amine;
6-(3-methyl-1H-pyrazol-4-yl)-N-[trans-4-(morpholin-4-yl)cyclohexyl]quinazolin-4-amine;
6-(1,5-dimethyl-1H-pyrazol-4-yl)-N-[trans-4-(morpholin-4-yl)cyclohexyl]quinazolin-4-amine;
6-(4-methyl-1H-imidazol-2-yl)-N-[trans-4-(morpholin-4-yl)cyclohexyl]quinazolin-4-amine;
6-(1,4-dimethyl-1H-imidazol-2-yl)-N-[trans-4-(morpholin-4-yl)cyclohexyl]quinazolin-4-amine;
6-(3,5-dimethyl-1H-pyrazol-4-yl)-N-[trans-4-(morpholin-4-yl)cyclohexyl]quinazolin-4-amine;
6-(2-methyl-1H-imidazol-4-yl)-N-[trans-4-(morpholin-4-yl)cyclohexyl]quinazolin-4-amine;
6-(2-cyclopropyl-1-methyl-1H-imidazol-5-yl)-N-[trans-4-(morpholin-4-yl)cyclohexyl]quinazolin-4-amine;
6-(1-methyl-1H-imidazol-2-yl)-N-[trans-4-(morpholin-4-yl)cyclohexyl]quinazolin-4-amine;
6-(1-methyl-1H-1,2,4-triazol-5-yl)-N-[trans-4-(morpholin-4-yl)cyclohexyl]quinazolin-4-amine;
6-(isoxazol-4-yl)-N-[trans-4-(morpholin-4-yl)cyclohexyl]quinazolin-4-amine;
6-(6-fluoro-5-methoxypyridin-3-yl)-N-[trans-4-(morpholin-4-yl)cyclohexyl]quinazolin-4-amine;
2-fluoro-5-(4-{[trans-4-(morpholin-4-yl)cyclohexyl]amino}quinazolin-6-yl)pyridin-3-ol;
6-[5-(dimethylamino)-6-fluoropyridin-3-yl]-N-[trans-4-(morpholin-4-yl)cyclohexyl]quinazolin-4-amine;
6-[6-fluoro-5-(methylamino)pyridin-3-yl]-N-[trans-4-(morpholin-4-yl)cyclohexyl]quinazolin-4-amine;
6-(6-chloro-5-fluoropyridin-3-yl)-N-[trans-4-(morpholin-4-yl)cyclohexyl]quinazolin-4-amine;
6-(5,6-difluoropyridin-3-yl)-N-[trans-4-(morpholin-4-yl)cyclohexyl]quinazolin-4-amine;
6-(5-(difluoromethyl)pyridin-3-yl)-N-[trans-4-(morpholin-4-yl)cyclohexyl]quinazolin-4-amine;
6-(5-amino-6-chloropyridin-3-yl)-N-[trans-4-(morpholin-4-yl)cyclohexyl]quinazolin-4-amine;
5-(4-(((trans)-4-(dimethylamino)cyclohexyl)amino)quinazolin-6-yl)pyridin-3-ol;
N,N-dimethyl-6-(4-(((trans)-4-morpholinocyclohexyl)amino)quinazolin-6-yl)picolinamide;

5-(4-{[trans-4-(4,4-difluoropiperidin-1-yl)cyclohexyl]amino}quinazolin-6-yl)-2-fluoropyridin-3-ol;
5-(4-{[trans-4-(3-methoxyazetidin-1-yl)cyclohexyl]amino}quinazolin-6-yl)pyridin-3-ol;
5-[4-({trans-4-[cyclopropyl(methyl)amino]cyclohexyl}amino)quinazolin-6-yl]pyridin-3-ol;
5-[4-({trans-4-[(2-methoxyethyl)amino]cyclohexyl}amino)quinazolin-6-yl]pyridin-3-ol;
5-(4-{[trans-4-(4-methylpiperazin-1-yl)cyclohexyl]amino}quinazolin-6-yl)pyridin-3-ol;
5-[4-({trans-4-[(2R,6S)-2,6-dimethylmorpholin-4-yl]cyclohexyl}amino)quinazolin-6-yl]pyridin-3-ol;
6-[5-(methylamino)pyridin-3-yl]-N-{trans-4-[4-(methylsulfonyl)piperazin-1-yl]cyclohexyl}quinazolin-4-amine;
N-[trans-4-(4,4-difluoropiperidin-1-yl)cyclohexyl]-6-[5-(methylamino)pyridin-3-yl]quinazolin-4-amine;
N-[trans-4-(4-fluoropiperidin-1-yl)cyclohexyl]-6-[5-(methylamino)pyridin-3-yl]quinazolin-4-amine;
6-(5-(methylamino)pyridin-3-yl)-N-{trans-4-[4-(morpholin-4-ylmethyl)piperidin-1-yl]cyclohexyl}quinazolin-4-amine;
6-(5-(methylamino)pyridin-3-yl)-N-{trans-4-[(3R)-3-(morpholin-4-ylmethyl)piperidin-1-yl]cyclohexyl}quinazolin-4-amine;
6-[5-(methylamino)pyridin-3-yl]-N-{trans-4-[(3S)-3-(morpholin-4-ylmethyl)piperidin-1-yl]cyclohexyl}quinazolin-4-amine;
2-fluoro-5-(4-{[trans-4-(4-fluoropiperidin-1-yl)cyclohexyl]amino}quinazolin-6-yl)pyridin-3-ol;
2-fluoro-5-[4-({trans-4-[4-(methylsulfonyl)piperazin-1-yl]cyclohexyl}amino)quinazolin-6-yl]pyridin-3-ol;
6-(5-amino-6-fluoropyridin-3-yl)-N-[trans-4-(4,4-difluoropiperidin-1-yl)cyclohexyl]quinazolin-4-amine;
6-(5-amino-6-fluoropyridin-3-yl)-N-[trans-4-(4-fluoropiperidin-1-yl)cyclohexyl]quinazolin-4-amine;
5-(4-{[trans-4-(4,4-difluoropiperidin-1-yl)cyclohexyl]amino}quinazolin-6-yl)pyridin-3-ol;
5-(4-{[trans-4-(4-fluoropiperidin-1-yl)cyclohexyl]amino}quinazolin-6-yl)pyridin-3-ol;
6-(5-amino-6-fluoropyridin-3-yl)-N-{trans-4-[(2R,6S)-2,6-dimethylmorpholin-4-yl]cyclohexyl}quinazolin-4-amine;
6-(5-amino-6-fluoropyridin-3-yl)-N-{trans-4-[4-(methylsulfonyl)piperazin-1-yl]cyclohexyl}quinazolin-4-amine;
6-(5-amino-6-fluoropyridin-3-yl)-N-{trans-4-[3-(morpholin-4-ylmethyl)piperidin-1-yl]cyclohexyl}quinazolin-4-amine;
6-(5-amino-6-fluoropyridin-3-yl)-N-{trans-4-[(2R)-2-(fluoromethyl)morpholin-4-yl]cyclohexyl}quinazolin-4-amine;
6-(5-amino-6-fluoropyridin-3-yl)-N-{trans-4-[(2S)-2-(fluoromethyl)morpholin-4-yl]cyclohexyl}quinazolin-4-amine;
6-(5-amino-6-fluoropyridin-3-yl)-N-{trans-4-[(2R)-2-methylmorpholin-4-yl]cyclohexyl}quinazolin-4-amine;
6-(5-amino-6-fluoropyridin-3-yl)-N-{trans-4-[(2S)-2-methylmorpholin-4-yl]cyclohexyl}quinazolin-4-amine;
N-{trans-4-[(2R,6S)-2,6-dimethylmorpholin-4-yl]cyclohexyl}-6-[6-fluoro-5-(methylamino)pyridin-3-yl]quinazolin-4-amine;
N-[trans-4-(4,4-difluoropiperidin-1-yl)cyclohexyl]-6-[6-fluoro-5-(methylamino)pyridin-3-yl]quinazolin-4-amine;
cyclopropyl {4-[trans-4-({6-[6-fluoro-5-(methylamino)pyridin-3-yl]quinazolin-4-yl}amino)cyclohexyl]piperazin-1-yl}methanone;
6-[6-fluoro-5-(methylamino)pyridin-3-yl]-N-[trans-4-(4-fluoropiperidin-1-yl)cyclohexyl]quinazolin-4-amine;
6-[6-fluoro-5-(methylamino)pyridin-3-yl]-N-{trans-4-[(2R)-2-methylmorpholin-4-yl]cyclohexyl}quinazolin-4-amine; and
6-[6-fluoro-5-(methylamino)pyridin-3-yl]-N-{trans-4-[(2S)-2-methylmorpholin-4-yl]cyclohexyl}quinazolin-4-amine;

or a pharmaceutically acceptable salt or stereoisomer thereof.

4. A pharmaceutical composition comprising a pharmaceutical carrier, and dispersed therein, a therapeutically effective amount of a compound of claim 1.

* * * * *